United States Patent
Endou et al.

(10) Patent No.: US 10,172,835 B2
(45) Date of Patent: Jan. 8, 2019

(54) ANTICANCER AGENT COMPOSITION

(71) Applicant: J-Pharma Co., Ltd., Kanagawa (JP)

(72) Inventors: Hitoshi Endou, Kanagawa (JP);
Michael F. Wempe, Aurora, CO (US);
Jean-Francois Peyron, Cantaron (FR);
Naohiko Anzai, Tokyo (JP); Promsuk Jutabha, Tochigi (JP)

(73) Assignee: J-Pharma Co., Ltd., Kanagawa (JP)

( * ) Notice: Subject to any disclaimer, the term of this patent is extended or adjusted under 35 U.S.C. 154(b) by 328 days.

(21) Appl. No.: 14/409,371

(22) PCT Filed: Jun. 7, 2014

(86) PCT No.: PCT/JP2014/065163
§ 371 (c)(1),
(2) Date: Dec. 18, 2014

(87) PCT Pub. No.: WO2015/173970
PCT Pub. Date: Nov. 19, 2015

(65) Prior Publication Data
US 2016/0279103 A1    Sep. 29, 2016

(30) Foreign Application Priority Data

May 15, 2014 (FR) ..................... 14 54362

(51) Int. Cl.
| | | |
|---|---|---|
| *A61K 31/423* | (2006.01) | |
| *A61K 45/06* | (2006.01) | |
| *A61K 31/436* | (2006.01) | |
| *A61K 31/24* | (2006.01) | |
| *A61K 31/513* | (2006.01) | |
| *A61K 31/5377* | (2006.01) | |
| *A61K 31/573* | (2006.01) | |
| *A61K 31/69* | (2006.01) | |
| *A61K 31/704* | (2006.01) | |
| *A61K 31/337* | (2006.01) | |
| *A61K 31/496* | (2006.01) | |
| *A61K 31/7068* | (2006.01) | |
| *A61K 33/24* | (2006.01) | |
| *A61K 38/50* | (2006.01) | |

(52) U.S. Cl.
CPC ............ *A61K 31/423* (2013.01); *A61K 31/24* (2013.01); *A61K 31/337* (2013.01); *A61K 31/436* (2013.01); *A61K 31/496* (2013.01); *A61K 31/513* (2013.01); *A61K 31/5377* (2013.01); *A61K 31/573* (2013.01); *A61K 31/69* (2013.01); *A61K 31/704* (2013.01); *A61K 31/7068* (2013.01); *A61K 33/24* (2013.01); *A61K 38/50* (2013.01); *A61K 45/06* (2013.01); *C12Y 305/01001* (2013.01)

(58) Field of Classification Search
None
See application file for complete search history.

(56) References Cited

FOREIGN PATENT DOCUMENTS

WO   2008/081537 A1   7/2008
WO   2013/183786 A1   12/2013

OTHER PUBLICATIONS

Wempe et al., Drug Metab. Pharamcokinet., 2012, vol. 27, No. 1, p. 155-161.*
Oda et al., Cancer Science, 2010, published online Nov. 2009, vol. 101, p. 173-179.*
Avellino et al., Blood, 2005, vol. 106, p. 1400-1406.*
Yanagida et al., Biochemica et Biophysica Acta, 2001, vol. 1514, p. 291-302.*
I Aifantis et al. "Molecular pathogenesis of T-cell leukaemia and lymphoma", Nature Reviews Immunology, May 2008, vol. 8, pp. 380-390 (12 pages).
C-H. Pui et al. "Acute Lymphoblastic Leukemia", The New England Journal of Medicine, Apr. 8, 2004, vol. 350, No. 15, pp. 1535-1548, (14 pages).
B. D. Cheson. "Novel therapies for peripheral T-cell non Hodgkin's lymphomas", Current Opinion in Hematology, vol. 16, Jul. 2009, pp. 299-305 (7 pages).
D. Hanahan et al. "Hallmarks of Cancer: The Next Generation", Cell, Mar. 4, 2011, vol. 144, pp. 646-674 (29 pages).
A. J. Levine et al. "The Control of the Metabolic Switch in Cancers by Oncogenes and Tumor Suppressor Genes", Science, Dec. 3, 2010, vol. 330, pp. 1340-1344 (7 pages).
W-L. Zhao. "Targeted therapy in T-cell malignancies: dysregulation of the cellular signaling pathways", Leukemia, Jan. 2010, vol. 24, No. 13, pp. 13-21 (10 pages).
P. A. Steck et al. "Identification of a candidate tumour suppressor gene, MMAC1, at chromosome 10q23.3 that is mutated in multiple advanced cancers", Nature Genetics, Apr. 1997, vol. 15, pp. 356-362 (7 pages).
I. Sansal et al. The Biology and Clinical Relevance of the PTEN Tumor Suppressor Pathway, Journal of Clinical Oncology, Jul. 15, 2004, vol. 22, No. 14, pp. 2954-2963 (10 pages).
L. Salmena et al. "Tenets of PTEN Tumor Suppression", Cell, May 2, 2008, vol. 133, pp. 403-414 (12 pages).
TJ. Hagenbeek et al. "T-cell lymphomas in T-cell-specific Pten-deficient mice originate in the thymus", Leukemia, 2008, vol. 22, pp. 608-619 (13 pages).
H. Ohkame et al. "Expression of L-type Amino Acid Transporter 1 (LAT1) and 4F2 Heavy Chain (4F2hc) in Liver Tumor Lesions of Rat Models", Journal of Surgical Oncology, 2001, vol. 78, pp. 265-272 (8 pages).

(Continued)

*Primary Examiner* — Kade Ariani
(74) *Attorney, Agent, or Firm* — Osha Liang LLP

(57) ABSTRACT

A method for treating cancer includes administering to a subject in need of the treatment an anticancer agent composition that includes the following agents as active ingredients; a LAT1 inhibitor, and one or more agents selected from the group consisting of an alkylating agent, a platinum-based antineoplastic agent, an anti-metabolite, a topoisomerase inhibitor, an anti-microtubule polymerizing agent, a hormonal agent, an anti-microtubule depolymerizing agent, an anticancer antibiotic, and a molecular targeted agent.

1 Claim, 36 Drawing Sheets

(56) References Cited

OTHER PUBLICATIONS

H. Kobayashi et al. "Expression of L-type Amino Acid Transporter 1 (LAT1) in Esophageal Carcinoma", Journal of Surgical Oncology, 2005, vol. 90, pp. 233-238 (6 pages).
K. Nakanishi et al. "LAT1 expression in normal lung and in atypical adenomatous hyperplasia and adenocarcinoma of the lung" Virchows Arch, 2006, vol. 448, pp. 142-150 (10 pages).
K. Kaira et al. "Fluorine-18-alpha-Methyltyrosine Positron Emission Tomography for Diagnosis and Staging of Lung Cancer: A Clinicopathologic Study", Clinical Cancer Research: an official journal of the American Association for Cancer Research, Nov. 1, 2007, vol. 13, No. 21, pp. 6369-6378 (11 pages).
T. Sakata et al. "L-type amino-acid transporter 1 as a novel biomarker for high-grade malignancy in prostate cancer", Pathology International 2009, vol. 59, pp. 7-18 (12 pages).
C. C. Feral et al. "CD98hc (SLC3A2) mediates integrin signaling", PNAS, Jan. 11, 2005, vol. 102, No. 2, pp. 355-360 (6 pages).
J. Toyoshima et al. "Investigation of the Role of Transporters on the Hepatic Elimination of an LAT1 Selective Inhibitor JPH203", Journal of Pharmaceutical Sciences, Sep. 2013, vol. 102, No. 9, pp. 3228-3238 (11 pages).
K. Yamauchi et al. "System L amino acid transporter inhibitor enhances anti-tumor activity of cisplatin in a head and neck squamous cell carcinoma cell line", Cancer Letters, 2009, vol. 276, No. 1, pp. 95-101 (7 pages).
S. Fukumoto et al. "A new treatment for human malignant melanoma targeting L-type amino acid transporter 1 (LAT1): A pilot study in a canine model", Biochemical and Biophysical Research Communications, 2013, vol. 439, No. 1, pp. 103-108 (6 pages).
S. Fukumoto et al. "L-type amino acid transporter 1 (LAT1): A new therapeutic target for canine mammary gland tumour", The Veterinary Journal, 2013, vol. 198, No. 1, pp. 164-169 (6 pages).
L Shi et al. "Downregulation of L-type amino acid transporter 1 expression inhibits the growth, migration and invasion of gastric cancer cells", Oncology Letters, 2013, vol. 6, No. 1, pp. 106-112 (7 pages).
K. Hayashi et al. "Role of c-Myc for regulation of LAT1 in cancer cells", Journal of Pharmacological Sciences, 2012, vol. 118, No. Suppl1.1, p. 120P, 03C1-1-2 (1 page).
S. Hayase at al. "Igaku Yogo Kaisetsu, LAT1", G. I. Research, 2009, vol. 17, No. 3, pp. 268-270 (5 pages).
D-W. Yun at al. "JPH2O3, an L-Type Amino Acid Transporter 1-Selective Compound, Induces Apoptosis of YD-38 Human Oral Cancer Cells", Journal of Pharmacological Sciences, 2014, vol. 124, No. 2, pp. 208-217 (10 pages).
Y. Kanai "Cancer drug delivery targeting amino acid transporters", Drug Delivery System, 2012, vol. 27, No. 5, pp. 342-349, with English translation of abstract (8 pages).
J. Vaage et al. "Therapy of a Xenografted Human Colonic Carcinoma Using Cisplatin or Doxorubicin Encapsulated in Long-Circulating Pegylated Stealth Liposomes", International Journal of Cancer, 1999, vol. 80, No. 1, pp. 134-137 (4 pages).
S. Ayral-Kaloustian et al. "Hybrid Inhibitors of Phosphatidylinositol 3-Kinase (PI3K) and the Mammalian Target of Rapamycin (mTOR): Design, Synthesis, and Superior Antitumor Activity of Novel Wortmannin -Rapamycin Conjugates", Journal of Medicinal Chemistry, 2010, vol. 53, No. 1, pp. 452-459 (8 pages).
H-Z Huo et al. "Dramatic suppression of colorectal cancer cell growth by the dual mTORC1 and mTORC2 inhibitor AZD-2014", Biochemical and Biophysical Research Communications, Jan. 2014, vol. 443, No. 2, pp. 406-412 (7 pages).
H. Imai et al. "Antitumor effect of L-type amino acid transporter (LAT1) inhibition in non-small cell lung cancer cell line", Japanese Journal of Lung Cancer, Oct. 2011, vol. 51, No. 5, p. 551, P-384 (3 pages).
A. Chairoungdua et al. "Amino acid transporters in malignant tumors as a candidate target for anti-cancer therapy", Journal of Japanese Biochemical Society, 2003, vol. 75, No. 8, p. 744, 3S58-2 (1 page).
D. Bressanin et al. "Harnessing the PI3K/Akt/mTOR pathway in T-cell acute lymphoblastic leukemia: Eliminating activity by targeting at different levels", Oncotarget, Aug. 2012, vol. 3, No. 8, pp. 811-823 (13 pages).
M. G. Kharas et al. "Ablation of PI3K blocks BCR-ABL leukemogenesis in mice, and a dual PI3K/mTOR inhibitor prevents expansion of human BCR-ABL+leukemia cells", The Journal of Clinical Investigation, Sep. 2008, vol. 118, No. 9, pp. 3038-3050 (13 pages).
P. Baumann et al. "The novel orally bioavailable inhibitor of phosphoinositol-3-kinase and mammalian target of rapamycin, NVP-BEZ235, inhibits growth and proliferation in multiple myeloma", Experimental cell Research, 2009, vol. 315, pp. 485-497 (13 pages).
M. Fujita et al. "Antitumor Activity of LY 188011, A New Deoxycytidine Analog, Against Human Cancers Xenografted Into Nude Mice", Cancer and chemotherapy, 1994, vol. 21, No. 4, pp. 517-523, with English translation of abstract 7 pages).
D. D. Von Hoff et al. "Increased Survival in Pancreatic Cancer with nab-Paclitaxel plus Gemcitabine", The New England Journal of Medicine, Oct. 31, 2013, vol. 369, No. 18, pp. 1691-1703 (13 pages).
C. Fotopoulou et al. "Additive Growth Inhibition after Combined Treatment of 2-Methoxyestradiol and Conventional chemotherapeutic Agents in Human Pancreatic Cancer Cells", Anticancer Research, 2010, vol. 30, No. 11, pp. 4619-4624 (6 pages).
H. Imai et al. "Inhibition of L-type Amino Acid Transporter 1 Has Antitumor Activity in Non-small Cell Lung Cancer", Anticancer Research, Dec. 2010, vol. 30, No. 12, pp. 4819-4828 (10 pages).
P. J. J Houghton et al. "Stage 2 Combination Testing of Rapamycin with Cytotoxic Agents by the Pediatric Preclinical Testing Program", Molecular Cancer Therapeutics, Jan. 12, 2010, vol. 9, No. 1, pp. 101-112 (13 pages).
X. Fan et al. "Impact of system L amino acid transporter 1 (LAT1) on proliferation of human ovarian cancer cells: A possible target for combination therapy with anti-proliferative aminopeptidase inhibitors", Biochemical Pharmacology, Sep. 15, 2010, vol. 80, No. 6, pp. 811-818 (8 pages).
International Search Report issued in International Application No. PCT/JP20141065163, dated Sep. 2, 2014 (4 pages).
Office Action issued in Japanese Application No. 2014-557910; dated Mar. 20, 2018 (17 pages).
Office Action issued in Japanese Application No. 2014-557910; dated Jun. 5, 2018 (12 pages).
Extended European Search Report issued in European Application No. 14809268.7, dated Feb. 8, 2016 (8 pages).
Communication pursuant to Article 94(3) EPC issued in European Application No. 14809268.7, dated Aug. 3, 2017 (6 pages).

* cited by examiner

*T-ALL patients*

FIG. 3B1
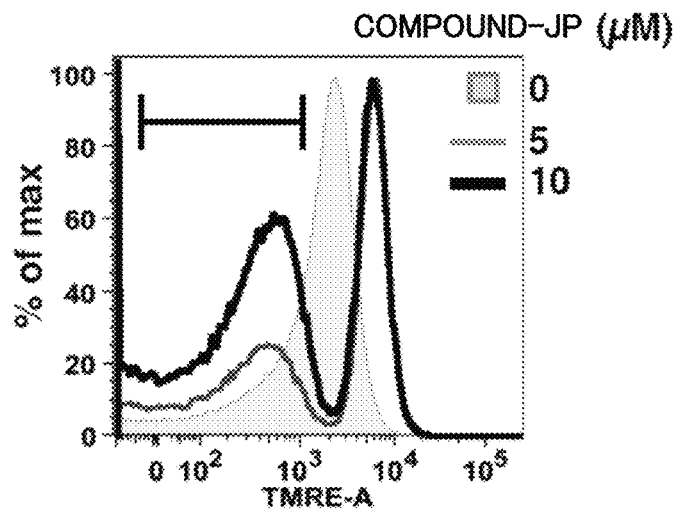
FIG. 3B2
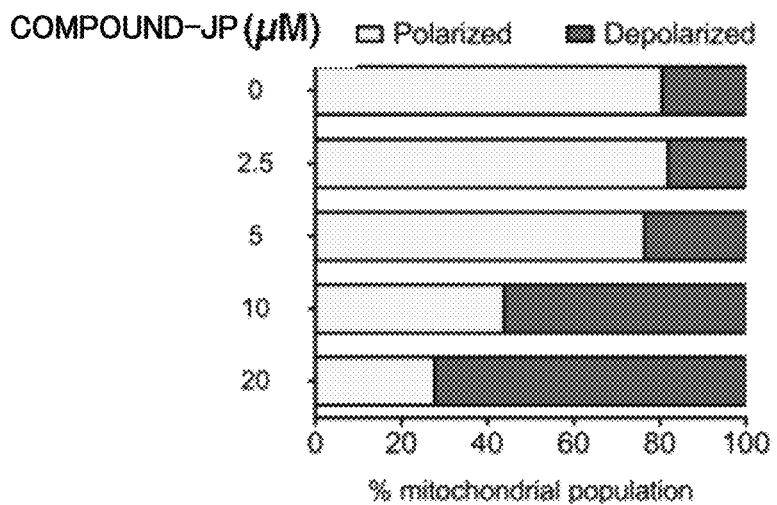
FIG. 3C
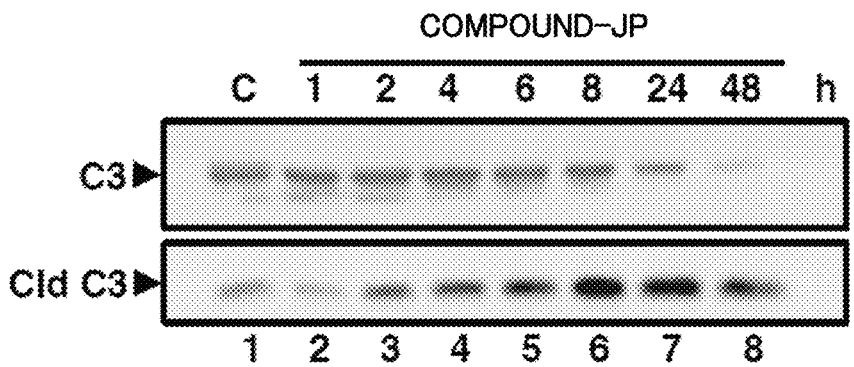

FIG. 3D1
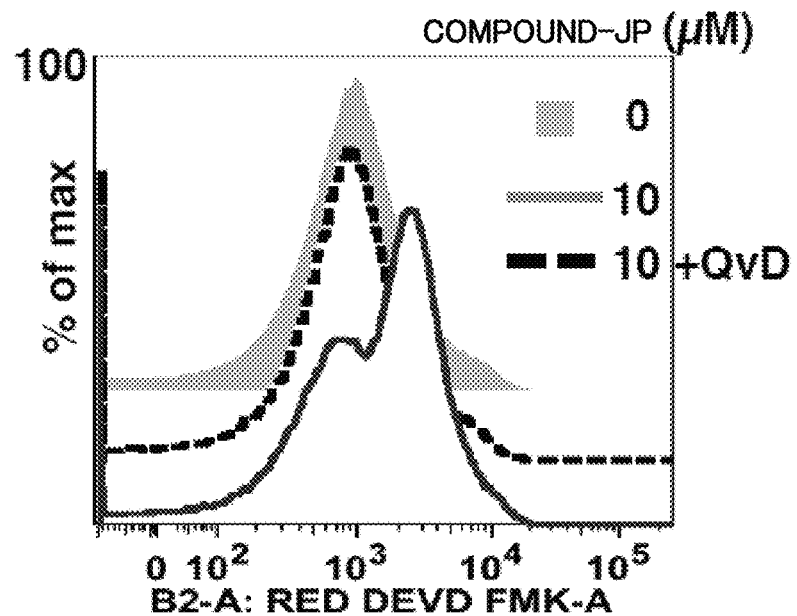
FIG. 3D2
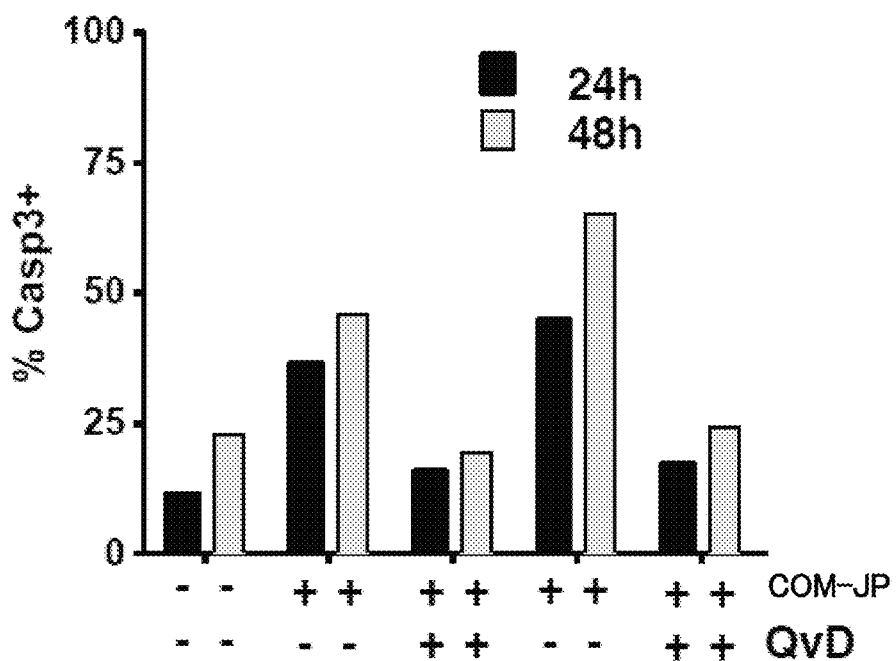

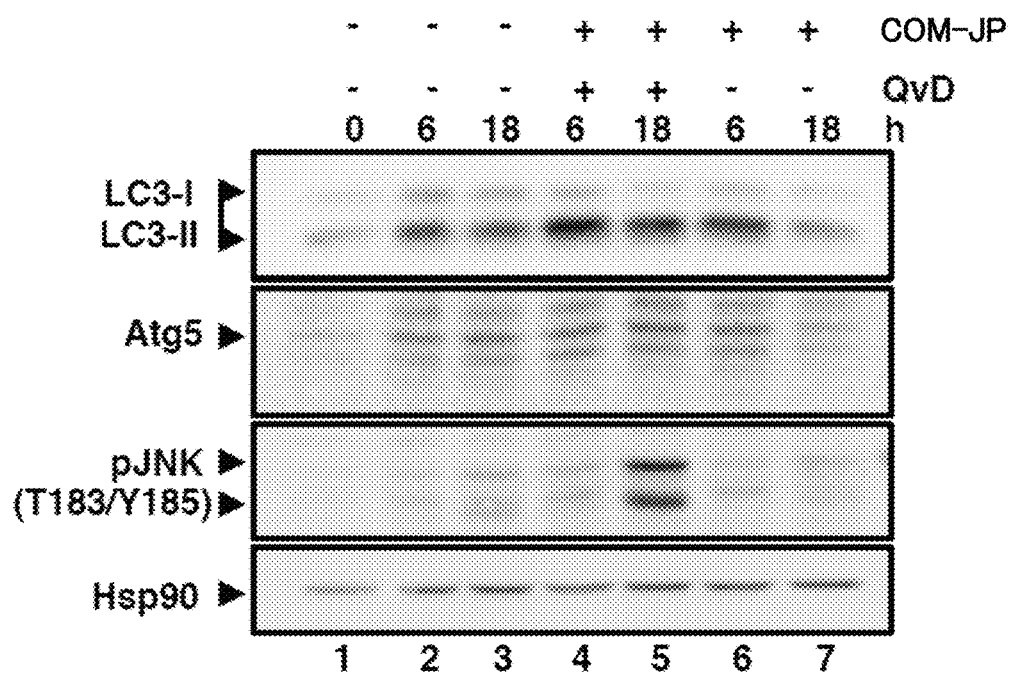

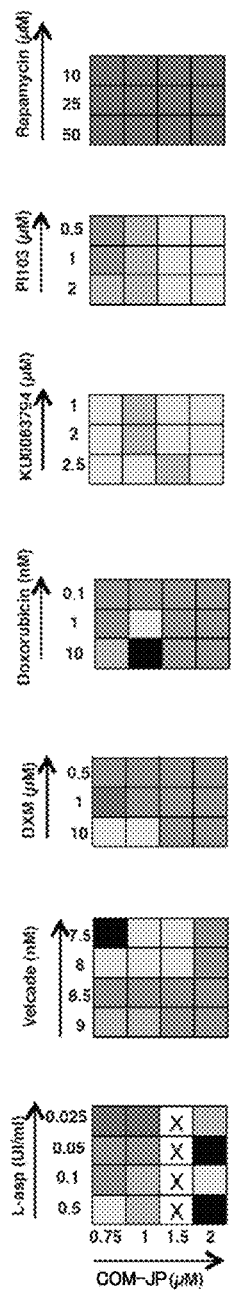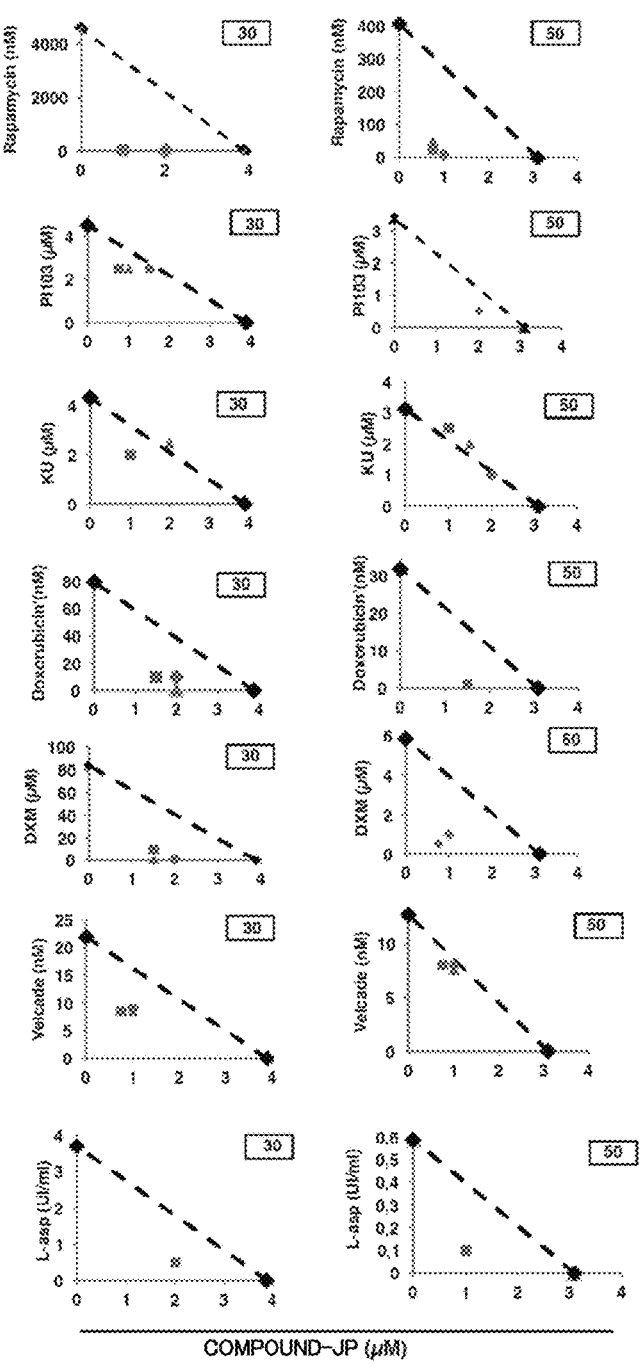
FIG. 8A
FIG. 8B

*Healthy donors*

*Activated PBLs*

Combination studies
KO90L (PTEN-/-) cells were incubated with COM-JP associated with other drugs for 48h at indicated concentrations before viability measurement using a WST1 assay
CI : combination index Molecular events of LAT1 Targeting by COMPOUND-JP Data are mean ± SE, n=4

*P<0.05, P<0.01, *P<0.001 vs. control

Data are mean ± SE, n=3
***P<0.001 vs. control

ANTICANCER AGENT COMPOSITION

CROSS REFERENCE TO RELATED APPLICATIONS

This is a national stage application based on PCT/JP2014/065163, filed on Jun. 7, 2014, which claims priority to French Patent Application No. 1454362, filed on May 15, 2014. This application claims the benefits and priority of these prior applications and incorporates their disclosures by reference in their entireties.

TECHNICAL FIELD

The present invention relates to a novel anticancer agent composition, for example a novel pharmaceutical composition for the treatment of T-cell acute lymphoblastic leukemia/lymphoma, pharmaceutical composition for the treatment of gastric cancer, pharmaceutical composition for the treatment of pancreatic cancer or pharmaceutical composition for the treatment of colon cancer.

BACKGROUND ART

It has not yet been found a satisfactory composition or method of treatment suppressing the growth of cancer (malignant tumor) reliably and hardly causing side effects, so development thereof is strongly desired.

In general, cancer cells repeat rapid proliferation, so uptake of essential amino acids, unable to be produced in intracellular metabolism, is abnormally increased. The present inventors have succeeded in molecular cloning of a cancer-specific L-type amino acid transporter which is a membrane protein required for cellular uptake of neutral branched chain amino acids and aromatic amino acids including a number of essential amino acids. The present inventors named this as a system L amino acid transporter 1 (LAT1) (Kanai Y. et al., Journal of Biological Chemistry, 273, 23629(1998)). After that, the present inventors have been searching for the agent composition selectively inhibiting LAT1 and LAT1 genes.

The types of cancer, for example, can be cited lung cancer, stomach cancer, pancreatic cancer, esophageal cancer, breast cancer, colon cancer, bladder cancer, prostate cancer and blood cancer, etc. In the following, blood cancer, stomach cancer, pancreatic cancer and colon cancer is described as an example.

As blood cancer (hematopoietic organ tumor), leukemia, lymphoma, myeloma, etc. are mentioned.

Leukemia is divided into 4 types (acute myeloid leukemia, chronic myelogenous leukemia, acute lymphocytic leukemia: all, chronic lymphatic leukemia). Acute Leukemia is a disease in which tumor genesis occurs in the hematopoietic stem cells or hematopoietic progenitor and only specific cells grow as leukemia cells.

Lymphoma is a tumor derived from the cells constituting lymphatic tissues, and is hematopoietic cell tumors caused mainly by canceration of lymphocytes. Malignant lymphoma is divided into Hodgkin's disease and non-Hodgkin's lymphoma.

Lymphocytic leukemia and lymphoma which are canceration of major constituent cells of lymphocytes are divided into B lymphocytic tumors and T lymphocytic tumors. T lymphocytic tumors include acute T lymphocytic leukemia (T-ALL), T Lymphoblastic Lymphoma (T-LL), chronis T lymphocytic leukemia (T-CLL), adult T cell leukemia (ATL) and the like.

Lymphoblastic Lymphoma (LL) is canceration lymphocytes at more immature stages of differentiation compared to the general lymphoma, and the nature of the cancer cells thereof is considered to be the same as acute lymphocytic leukemia. Therefore, they are classified to a group of diseases as "Precursor T- or B-Lymphoblastic Leukemia/Lymphoma" In the WHO classification.

T-cell lymphoblastic lymphomas (T-LL) and T-cell acute lymphoblastic leukemia (T-ALL) are highly aggressive diseases which originate from the transformation of thymocytes blocked at different stages of differentiation (Non-Patent Literature 1). T-ALL represents approximately 15 and 30% of all adult and childhood non-Hodgkin lymphomas, respectively. In recent years, aggressive chemotherapy treatments in T-ALL patients have improved cure rates to greater than 40% in adult and 80% in pediatric patients (Non-Patent Literature 2); however, refractory relapses are well-known to occur in all available drug treatments (Non-Patent Literature 3). Consequently, the present inventors deem that more knowledge regarding the molecular mechanisms involved in the pathogenesis of T cell malignancies is absolutely vital in order to identify novel and/or combinational treatments to enhance these cure rates.

Tumorigenic cells (cancer cells) are well-known to display hallmark properties (Non-Patent Literature 4) which allow them to continuously proliferate, escape elimination by apoptosis, disseminate and resist treatments. Cancer cells have reprogrammed their metabolism (Non-Patent Literature 5); a property which has enhanced their ability to sequester nutrients required to produce new proteins, lipids and DNA in order for the cancer cells to quickly grow and actively divide. Because they harbor different genetic lesions, such as chromosomal translocations that promote oncogenic proliferation and perturb differentiation, T-ALL/T-LL cells are highly heterogeneous at the molecular level (Non-Patent Literature 1). Nevertheless, it has been shown that they have a common and essential activation of the Phosphatidylinositide 3-Kinase/Protein Kinase B; PKB (PI3K/Akt) pathway (Non-Patent Literature 6). PI3K/Akt is repressed by the tumor suppressor gene PTEN (phosphatase and tensin homolog deleted on chromosome 10) which is frequently inactivated in human cancers (Non-Patent Literature 7). The PTEN lipid phosphatase activity counteracts the action of PI3K-explicitly involved in cell survival (i.e. growth, proliferation, intracellular trafficking)—by reversing phosphatidylinositol (3,4,5)-triphosphate (PIP3) to phosphatidylinositol 4,5-bisphosphate (PIP2) which prevents Akt activation and downstream proliferative events. In the absence of PTEN, Akt is fully active and stimulates cells toward cancerous transformation (Non-Patent Literature 8, 9).

In order to investigate PTEN's participation at the molecular level in the pathogenesis of T-ALL/T-LL, the present inventors utilized a murine model exhibiting a conditional, T-cell specific, PTEN deletion (PTENf/fxlck-Cre) (Non-Patent Literature 10). The resulting progeny (tPTEN−/− mice) quickly develop aggressive and invasive T cell lymphomas and die within 6 to 20 weeks. In order to highlight the deregulated genes that support tPTEN−/− lymphomagenesis, a transcriptomic (expression profiling) analysis was performed which identified SLC7A5 gene up-regulation. SLC7A5 encodes System L Amino Acid Transporter 1 (LAT1). In recent years, significant findings have demonstrated that many cancerous and/or proliferating cells are strongly linked to LAT1 expression (Non-Patent Literature 11); (Non-Patent Literature 12); (Non-Patent Literature 13); (Non-Patent Literature 14); (Non-Patent Literature 15); (Non-Patent Literature 16) and efforts to develop LAT1 potent and selective inhibitors are proceeding (Non-Patent Literature 17). Thus far, four LAT proteins (i.e. LAT1-4) have been identified with LAT1 and LAT3 being the two isoforms which are most frequently overexpressed in tumor cells (Non-Patent Literature 18). LAT proteins import large neutral essential amino-acids (LNEAA) such as leucine, valine, isoleucine, phenylalanine and tyrosine in exchange with glutamine. In order to be transport functional, LAT1 requires a disulfide-linkage bound to a single membrane spanning protein 4F2 cell surface antigen heavy chain (CD98hc/4F2hc; encoded by SLC3A2 gene) (Non-Patent Literature 11); it is also known to interact with β integrins (Non-Patent Literature 19). The observed LAT1 expression at the tPTEN−/− and T-ALL/T-LL cell surface presumable equates to higher essential amino acid uptake and thereby speculated to be a contributing factor to T-ALL/T-LL leukemia cell growth and survival.

Thus, the main aim of the research by the present inventors was to perform studies to probe the potential pharmacological role(s) of targeting LAT1 by utilizing COMPOUND-JP, a potent and selective LAT1 inhibitor (Non-Patent Literature 18); (Non-Patent Literature 17); (Non-Patent Literature 20).

CITATION LIST

Non-Patent Literature

Non-Patent Literature 1: I. Aifantis, E. Raetz, S. Buonamici, Molecular pathogenesis of T-cell leukeamia and lymphoma. Nature Reviews Immunology 8, 380 (2008).
Non-Patent Literature 2: C. Pui, M. Relling, D. Pharm, J. Downing, Acute lymphoblastic leukemia. N Engl J Med 350, 1535 (2004).
Non-Patent Literature 3: B. D. Cheson, Novel therapies for peripheral T-cell non-Hodgkin's lymphomas. Curr Opin Hematol 16, 299 (July, 2009).
Non-Patent Literature 4: D. Hanahan, R. Weinberg, Hallmarks of cancer: the next generation. Cell 144, 646 (2011).
Non-Patent Literature 5: A. Levine, A. Puzio-Kuter, The control of the metabolic switch in cancers by oncogenes and tumor suppressor genes. Science 330, 1340 (2010).
Non-Patent Literature 6: W. L. Zhao, Targeted therapy in T-cell malignancies: dysregulation of the cellular signaling pathways. Leukemia 24, 13 (January, 2010).
Non-Patent Literature 7: P. Steck et al., Identification of a candidate tumour suppressor gene, MMAC1, at chromosome 10q23.3 that is mutated in multiple advanced cancers. Nat Genet 15, 356 (1997).
Non-Patent Literature 8: I. Sansal, W. Sellers, The biology and clinical relevance of the PTEN tumor suppressor pathway. J Clin Oncol 22, 2954 (2004).
Non-Patent Literature 9: L. Salmena, A. Carracedo, P. Pandolfi, Tenets of PTEN tumor suppression. Cell 133, 403 (2008).
Non-Patent Literature 10: T. Hagenbeek, H. Spits, T-cell lymphomas in T-cell specific Pten-deficient mice originate in the thymus. Leukemia 22, 608 (2007).
Non-Patent Literature 11: O. Yanagida et al., Human L-type amino acid transporter 1 (LAT1): characterization of function and expression in tumor cell lines. Biochem Biophys Acta 1514, 291 (Oct. 1, 2001).
Non-Patent Literature 12: H. Ohkame, H. Masuda, Y. Ishii, Y. Kanai, Expression of L-type amino acid transporter 1 (LAT1) and 4F2 heavy chain (4F2hc) in liver tumor lesions of rat models. Journal of surgical oncology 78, 265 (December, 2001).
Non-Patent Literature 13: H. Kobayashi, Y. Ishii, T. Takayama, Expression of L-type amino acid transporter 1 (LAT1) in esophageal carcinoma. Journal of surgical oncology 90, 233 (Jun. 15, 2005).
Non-Patent Literature 14: K. Nakanishi et al., LAT1 expression in normal lung and in atypical adenomatous hyperplasia and adenocarcinoma of the lung. Virchows Archiv: an international journal of pathology 448, 142 (February, 2006).
Non-Patent Literature 15: K. Kaira et al., Fluorine-18-alpha-methyltyrosine positron emission tomography for diagnosis and staging of lung cancer: a clinicopathologic study. Clinical cancer research: an official journal of the American Association for Cancer Research 13, 6369 (Nov. 1, 2007).
Non-Patent Literature 16: T. Sakata et al., L-type amino-acid transporter 1 as a novel biomarker for high-grade malignancy in prostate cancer. Pathol Int 59, 7 (January, 2009).
Non-Patent Literature 17: M. F. Wempe et al., Metabolism and pharmacokinetic studies of JPH203, an L-amino acid transporter 1 (LAT1) selective compound. Drug metabolism and pharmacokinetics 27, 155 (2012).
Non-Patent Literature 18: K. Oda et al., L-type amino acid transporter 1 inhibitors inhibit tumor cell growth. Cancer Sci 101, 173 (January, 2010).
Non-Patent Literature 19: C. C. Feral et al., CD98hc (SLC3A2) mediates integrin signaling. Proceedings of the National Academy of Sciences of the United States of America 102, 355 (Jan. 11, 2005).
Non-Patent Literature 20: J. Toyoshima, H. Kusuhara, M. F. Wempe, H. Endou, Y. Sugiyama, Investigation of the role of transporters on the hepatic elimination of an LAT1 selective inhibitor JPH203. Journal of pharmaceutical sciences 102, 3228 (September, 2013).

SUMMARY OF INVENTION

Technical Problem

The present invention provides a satisfactory anticancer agent composition suppressing the growth of cancer (malignant tumor) reliably and hardly causing side effects, for example, a novel pharmaceutical composition increasing a cure rate of T-LL patient and T-AAL patient, a pharmaceutical composition for the treatment of gastric cancer, a pharmaceutical composition for the treatment of pancreatic cancer or a pharmaceutical composition for the treatment of colon cancer.

Solution to Problem

Reprogrammed cancer cells require high nutrient influx to support their pathological growth and proliferation rates. The gene (SLC7A5) encoding System L amino acid transporter 1 (LAT1) was shown to be over-expressed in murine lymphoma cells generated via T cell deletion of the pten tumor suppressor and also in human T-cell Acute lymphoblastic leukemia (T-ALL)/lymphoma (T-LL) cells, by intensive researches. Then, in the current studies, the present inventors utilized a certain LAT1 selective inhibitor (for instance, O-(5-amino-2-phenylbenzoxazole-7-yl)methyl-3, 5-dichloro-L-tyrosine or its pharmacologically acceptable salt, hereinafter referred to as "COMPOUND-JP"). COMPOUND-JP decreased leukemic cell viability and proliferation, induced transient autophagy which was followed by apoptosis; in addition, COMPOUND-JP was able to alter the in vivo growth of xenografted luciferase-expressing-tPTEN−/− cells administered into nude mice. In contrast, COMPOUND-JP was non-toxic to normal murine thymocytes and to human peripheral blood lymphocytes. At a molecular level, COMPOUND-JP inhibited the constitutive activation of mTORC1 and Akt. COMPOUND-JP triggered an Unfolded Protein Response (UPR) mediated by the CHOP transcription factor associated with cell death. Curiously, the present inventors also generated a COMPOUND-JP-resistant tPTEN−/− clone which was CHOP induction deficient. In addition, the present inventors observed that COMPOUND-JP could synergized with rapamycin, dexamethasone, doxorubicin, velcade and L-asparaginase to alter leukemic cell viability. The results demonstrate that targeting essential amino acid influx mediated via LAT1 may be an efficient broad spectrum adjuvant approach to treat deadly T-cell malignancies.

That is, the experimental results generated from the current studies support the notion that T-ALL and T-LL cells, and tPTEN−/− mice, rely on a high level of amino-acid influx mediated via LAT1 in order for the cancer cells to survive and proliferate. Inhibiting LAT1 using COMPOUND-JP affected the constitutive activation of the mTOR pathway which sustained the survival of tPTEN−/− tumor cells, triggered a CHOP-dependent—cell death response and displayed interesting in vitro adjuvant drug properties.

According to the Quantitative results of a neutral amino acid transporter, LAT1 gene and LAT2 gene expressed in an established culture cell derived from various cancers of a human being, the LAT2 was expressed in only 5 kinds of cells. However the LAT1 mRNA was expressed in all of the 46 kinds of cells, and it can be said to be a cancer-type transporter. On the other hand, the expression of the LAT2 is zero or extremely low level in a cancer cell, and it can be understand to be a normal type. And dose-dependent decrease of the proliferation activity of COM-JP was apparently recognized in both cells of a 44As3-1 cell derived from human scirrhous stomach cancer and a Panc-1 cell derived from human pancreatic cancer. An inhibitory effect on the proliferation of COM-JP depending on the LAT1 expression level can be expected also in many other LAT1-expressing cancer cells.

Next, the results of the effect about stomach cancer, pancreatic cancer and large intestine cancer when COM-JP and other agents were used in combination. First, according to the effect on the proliferation of a 44As3-11 cell derived from human scirrhous stomach cancer when COM-JP and other agents (Gemstabine and Paclitaxel) were used in combination, the proliferation of a 44As3-11 cell derived from human scirrhous stomach cancer when COM-JP and other agents were used in combination, the inhibitory effect due to the combination was resulted from the addition of each single effect, and showed a so-called additive effect. Next, according to the effect on the tumor growth in a nude mouse model inoculated with a HT-29 cell derived from human large intestine cancer when COM-JP and 5-FU were used in combination, with the combination of both, the increase of the residual tumor in each single group was further decreased. It was revealed that this combined effect is additive, and due to the difference of the action mechanism of both pharmaceuticals. The efficacy that can be further enhanced by such combination compared with each single effect of the effectiveness of treatment is fully expected at colon cancer treatment in the clinical. Medicinal such it is possible to further enhance each sole therapeutic effect of the combination is also fully expected in colon cancer treatment in the clinical. Finally, according to the synergistic effect on the tumor growth in a nude mouse model (SOI model) inoculated in the same site with a HT-29 cell derived from human large intestine cancer when COM-JP and CDDP were used in combination, each efficacy that was not recognized in the single administration of each of COM-JP and CDDP was apparently recognized in the combination of COM-JP and CDDP. It was concluded that the efficacy of due to the combination was a synergistic effect.

It is found out that an effective anticancer agent composition is obtained by a LAT1 inhibitor and the combination of a LAT1 inhibitor and other agents.

The present invention (1) relates to an anticancer agent composition including the following agents as active ingredient; a LAT1 inhibitor, and one or more agents selected from the group consisting of an alkylating agent, a platinum-based antineoplastic agent, an anti-metabolite, a topoisomerase inhibitor, an anti-microtubule polymerizing agent, a hormonal agent, an anti-microtubule depolymerizing agent, an anticancer antibiotic, and a molecular targeted agent.

The present invention (2) relates to the composition according to the preceding clause (1), wherein the anticancer agent composition is a pharmaceutical composition for treating T-cell acute lymphoblastic leukemia/lymphomas, a pharmaceutical composition for treating stomach cancer, a pharmaceutical composition for treating pancreatic cancer, or a pharmaceutical composition for treating colorectal cancer.

The present invention (3) relates to the composition according to the preceding clause (1) or (2), wherein the LAT1 inhibitor is O-(5-amino-2-phenylbenzoxazole-7-yl)methyl-3,5-dichloro-L-tyrosine and its analog or pharmacologically acceptable salts thereof.

The present invention (4) relates to the composition according to any one of claims 1 to 3, wherein the agent is one or more agents selected from cisplatin, 5-fluorouracil (5-FU), gemcitabine, L-asparaginase (leunase), paclitaxel, dexamethasone, an anthracycline antibiotic including doxorubicin, velcade (bortezomib), rapamycin, KU0063794 and PI-103.

The present invention (5) relates to an anticancer agent composition including a LAT1 inhibitor, and one or more agents selected from an mTOR inhibitor, a PI3K inhibitor, and an Akt inhibitor.

The present invention (6) relates to the composition according to the preceding clause (5), wherein the anticancer agent composition is a pharmaceutical composition for treating T-cell acute lymphoblastic leukemia/lymphomas, a pharmaceutical composition for treating stomach cancer, a pharmaceutical composition for treating pancreatic cancer, or a pharmaceutical composition for treating colorectal cancer.

The present invention (7) relates to the composition according to the preceding clause (5) or (6), wherein the LAT1 inhibitor is O-(5-amino-2-phenylbenzoxazole-7-yl)methyl-3,5-dichloro-L-tyrosine and its analog or pharmacologically acceptable salts thereof.

The present invention (8) relates to the composition according to the preceding clause (5) to (7), wherein the agent is one or more agents selected from rapamycin, KU0063794, and PI-103.

The terms in the present Specification mean as follows:
(LAT1 Inhibitor)

The "LAT1 inhibitor" includes, but not limited to as long as the agent can selectively inhibit system L amino acid transporter 1 (LAT1) and LAT1 gene, a compound and a salt thereof, anti-LAT1 antibody, aptamer, nucleic acid medicine. The LAT1 inhibitor includes alone or a combination of two or more.

(Alkylating Agent)

The "alkylating agent" includes, but not limited to as long as an agent can alkylate DNA, for example, any one or more existing alkylating agents whose manufacture and sales as a pharmaceutical agent have been approved by a governmental organization, or any one or more alkylating agents that are currently used in clinical or preclinical trials, or will be used in clinical trials in the future, whose manufacture and sales as a pharmaceutical agent may be approved by a governmental organization after the trials. The alkylating agent includes alone or a combination of two or more.

(Platinating Agent)

The "platinating agent" includes, but not limited to as long as an agent is an anticancer pharmaceutical including platinum, for example, any one or more existing platinating agents whose manufacture and sales as a pharmaceutical agent have been approved by a governmental organization, or any one or more platinating agents that are currently used in clinical or preclinical trials, or will be used in clinical trials in the future, whose manufacture and sales as a pharmaceutical agent may be approved by a governmental organization after the trials. The platinating agent includes alone or a combination of two or more.

(Antimetabolite)

The "antimetabolite" includes, but not limited to as long as an agent inhibits metabolism of cancer cells to suppress the proliferation, for example, any one or more existing antimetabolites whose manufacture and sales as a pharmaceutical agent have been approved by a governmental organization, or anyone or more antimetabolites that are currently used in clinical or preclinical trials, or will be used in clinical trials in the future, whose manufacture and sales as a pharmaceutical agent may be approved by a governmental organization after the trials. The antimetabolite includes alone or a combination of two or more.

(Topoisomerase Inhibitor)

The "topoisomerase inhibitor" includes, but not limited to as long as an agent is one which inhibits the function of an enzyme called as topoisomerase, for example, any one or more existing topoisomerase inhibitors whose manufacture and sales as a pharmaceutical agent have been approved by a governmental organization, or any one or more topoisomerase inhibitors that are currently used in clinical or preclinical trials, or will be used in clinical trials in the future, whose manufacture and sales as a pharmaceutical agent may be approved by a governmental organization after the trials. The topoisomerase inhibitor includes alone or a combination of two or more.

(Microtubule Inhibitor)

The "microtubule inhibitor" includes, but not limited to as long as an agent can interfere with formation of microtubule, for example, any one or more existing microtubule inhibitors whose manufacture and sales as a pharmaceutical agent have been approved by a governmental organization, or any one or more microtubule inhibitors that are currently used in clinical or preclinical trials, or will be used in clinical trials in the future, whose manufacture and sales as a pharmaceutical agent may be approved by a governmental organization after the trials. The microtubule inhibitor includes alone or a combination of two or more.

(Endocrine Therapy Agent)

The "endocrine therapy agent" includes, but not limited to as long as an agent can suppress the secretion or action of endocrine (hormone), for example, any one or more existing endocrine therapy agents whose manufacture and sales as a pharmaceutical agent have been approved by a governmental organization, or any one or more endocrine therapy agents that are currently used in clinical or preclinical trials, or will be used in clinical trials in the future, whose manufacture and sales as a pharmaceutical agent may be approved by a governmental organization after the trials. The endocrine therapy agent includes alone or a combination of two or more.

(Microtubule Depolymerizing Inhibitor)

The "microtubule depolymerizing inhibitor" includes, but not limited to as long as an agent can stabilize microtubule polymerizing, for example, any one or more existing microtubule depolymerizing inhibitors whose manufacture and sales as a pharmaceutical agent have been approved by a governmental organization, or any one or more microtubule depolymerizing inhibitors that are currently used in clinical or preclinical trials, or will be used in clinical trials in the future, whose manufacture and sales as a pharmaceutical agent may be approved by a governmental organization after the trials. The microtubule depolymerizing inhibitor includes alone or a combination of two or more.

(Antitumor Antibiotic)

The "antitumor antibiotic" includes, but not limited to as long as a substance functions as an antitumor agent and is derived from microbial produced substance, for example, any one or more existing antitumor antibiotics whose manufacture and sales as a pharmaceutical agent have been approved by a governmental organization, or any one or more antitumor antibiotics that are currently used in clinical or preclinical trials, or will be used in clinical trials in the future, whose manufacture and sales as a pharmaceutical agent may be approved by a governmental organization after the trials. The antitumor antibiotic includes alone or a combination of two or more.

(Molecular-Targeted Agent)

The "molecular-targeted agent" includes, but not limited to as long as an agent targets a molecule relating to proliferation, invasion, metastasis, etc., of tumor cell, for example, any one or more existing molecular-targeted agents whose manufacture and sales as a pharmaceutical agent have been approved by a governmental organization, or any one or more molecular-targeted agents that are currently used in clinical or preclinical trials, or will be used in clinical trials in the future, whose manufacture and sales as a pharmaceutical agent may be approved by a governmental organization after the trials. The molecular-targeted agent includes alone or a combination of two or more.

(Anticancer Agent)

The "anticancer agent" includes, for example, an alkylating agent, a platinating agent, an antimetabolite, vegetable alkaloid (a topoisomerase inhibitor, a microtubule inhibitor, microtubule a depolymerizing inhibitor, etc.), an endocrine therapy agent, an antitumor antibiotic, a molecular-targeted agent, a biological response modifier and other pharmaceuticals, for example, any one or more existing anticancer agents whose manufacture and sales as a pharmaceutical agent have been approved by a governmental organization, or any one or more anticancer agents that are currently used in clinical or preclinical trials, or will be used in clinical trials in the future, whose manufacture and sales as a pharmaceutical agent may be approved by a governmental organization after the trials. The anticancer agent includes alone or a combination of two or more.

The "analog" means a molecule which is substantially similar to O-(5-amino-2-phenyl-benzoxazol-7-yl)methyl-3,5-dichloro-L-tylosine in structure and function.

(Cisplatin)

The "cisplatin" means cisplatin (CDDP), which is a platinating agent, and includes cisplatin and any analog, derivative and homolog thereof which has the same pharmacological properties as cisplatin.

(5-fluorouracil (5-FU))

The "5-fluorouracil (5-FU)" means 5-fluorouracil (5-FU), which is an antimetabolite, and includes 5-fluorouracil (5-FU) and any analog, derivative and homolog thereof which has the same pharmacological properties as 5-fluorouracil (5-FU).

(Gemcitabine)

The "gemcitabine" means gemcitabine, which is an antimetabolite, and includes gemcitabine and any analog, derivative and homolog thereof which has the same pharmacological properties as gemcitabine.

(L-asparaginase (Leunase))

The "L-asparaginase (leunase)" means L-asparaginase (leunase), which is an anticancer agent, and includes L-asparaginase (leunase) and any analog, derivative and homolog thereof which has the same pharmacological properties as L-asparaginase (leunase).

(Paclitaxel)

The "paclitaxel" means paclitaxel (taxol), which is a microtubule depolymerizing inhibitor, and includes paclitaxel and any analog, derivative and homolog thereof which has the same pharmacological properties as paclitaxel.

(Dexamethasone)

The "dexamethasone" means dexamethasone, which is a pharmaceutical containing adrenocortical steroid as main component that has anti-inflammatory effect, immunodepressive effect and so on, and includes dexamethasone and any analog, derivative and homolog thereof which has the same pharmacological properties as dexamethasone.

(Anthracycline Antibiotic including Doxorubicin)

The "anthracycline antibiotic" includes, but not limited to as long as a group of an agent belongs to pharmaceuticals using as an antitumor antibiotic derived from Streptomyces microorganism, for example, any one or more existing anthracycline antibiotics whose manufacture and sales as a pharmaceutical agent have been approved by a governmental organization, or any one or more anthracycline antibiotics that are currently used in clinical or preclinical trials, or will be used in clinical trials in the future, whose manufacture and sales as a pharmaceutical agent may be approved by a governmental organization after the trials. The anthracycline antibiotic includes alone or a combination of two or more. The "doxorubicin" means doxorubicin, which is an anthracycline antibiotic, and includes doxorubicin and any analog, derivative and homolog thereof which has the same pharmacological properties as doxorubicin.

(Velcade(Bortezomib))

The "Velcade(bortezomib)" means Velcade(bortezomib), which is a molecular-targeted agent, and includes Velcade (bortezomib) and any analog, derivative and homolog thereof which has the same pharmacological properties as Velcade(bortezomib).

(Rapamycin)

The "rapamycin" means rapamycin, which is a molecular-targeted agent, and includes rapamycin and any analog, derivative and homolog thereof which has the same pharmacological properties as rapamycin.

(KU0063794)

The "KU0063794" means KU0063794, which is a molecular-targeted agent, and includes KU0063794 and any analog, derivative and homolog thereof which has the same pharmacological properties as KU0063794.

(PI-103)

The "PI-103" means PI-103, which is a molecular-targeted agent, and includes PI-103 and any analog, derivative and homolog thereof which has the same pharmacological properties as PI-103.

(mTOR Inhibitor)

The "mTOR inhibitor" includes, but not limited to as long as an agent which directly or indirectly targets mTOR (mammalian target of rapamycin) or decreases or inhibits an activity/function of mTOR, for example, any one or more existing mTOR inhibitor whose manufacture and sales as a pharmaceutical agent have been approved by a governmental organization, or any one or more mTOR inhibitor that are currently used in clinical or preclinical trials, or will be used in clinical trials in the future, whose manufacture and sales as a pharmaceutical agent may be approved by a governmental organization after the trials. The mTOR inhibitor includes alone or a combination of two or more.

(PI3K Inhibitor)

The "PI3K inhibitor" includes, but not limited to as long as an agent which directly or indirectly targets PI3K (PI3K kinase) or decreases or inhibits an activity/function of PI3K, for example, any one or more existing PI3K inhibitor whose manufacture and sales as a pharmaceutical agent have been approved by a governmental organization, or any one or more PI3K inhibitor that are currently used in clinical or preclinical trials, or will be used in clinical trials in the future, whose manufacture and sales as a pharmaceutical agent may be approved by a governmental organization after the trials. The PI3K inhibitor includes alone or a combination of two or more.

(Akt Inhibitor)

The "Akt inhibitor" includes, but not limited to as long as an agent which directly or indirectly targets Akt or decreases or inhibits an activity/function of Akt, for example, any one or more existing Akt inhibitor whose manufacture and sales as a pharmaceutical agent have been approved by a governmental organization, or any one or more Akt inhibitor that are currently used in clinical or preclinical trials, or will be used in clinical trials in the future, whose manufacture and sales as a pharmaceutical agent may be approved by a governmental organization after the trials. The Akt inhibitor includes alone or a combination of two or more.

BRIEF DESCRIPTION OF DRAWINGS

FIG. 1 shows the tPTEN−/− tumors, T-ALL/T-LL cell lines, and primary samples expressing elevated levels of CD98

FIG. 1B shows the primary tumor cells from tPTEN−/− mice (n=5) compared to thymocytes from a normal WT mouse. P-values were calculated using ANOVA followed by a Dunnett's multiple comparison test at the 95% confidence level.

FIG. 1C shows the CD98 expression levels between resting or PMA+ionomycin-activated (24 h) normal murine thymocytes and KO99L cells.

FIG. 1D shows the CD98 expression in primary T-ALL samples (n=3), T-ALL/T-LL human cell lines and normal resting or activated PBLs. P-values were calculated using ANOVA-Dunnett.

FIG. 1E shows the facs profiles of CD98 expression between resting or 24 h-activated human PBLs and T-ALL sample #1.

FIG. 2 shows the functional effects of LAT-1 inhibition in tPTEN−/− and T-ALL/T-LL cellular models

FIG. 2E shows the tumor volumes; Student's t test.

FIG. 2F shows the whole body mice imaging. A pseudocolor scale shows relative bioluminescence changes over time (ph/s/r:photons/second/radiance).

FIG. 2G shows the bioluminescence quantification of tumors; p-value calculated using the two-tailed Mann-Whitney test.

FIG. 3 shows shows the result that COMPOUND-JP induces caspase activation, apoptotic cell death and autophagy

FIG. 3B shows the result of the mitochondrial potential measured by Facs after TMRE staining, after stimulation of KO99L cells with COMPOUND-JP for 48 h. B1, Facs profiles; B2, quantification of the results. Representative of two independent experiments.

FIG. 3C shows the result of the time course Western blot analysis of caspase 3 activation in KO99L cells. Cld C3=cleaved (active) caspase 3. Representative of three independent experiments.

FIG. 3D shows the facs profiles of caspase 3 activation after 48 h, using the Red-DEVD-fmk fluorescent substrate (D1) and the quantification of the results that are representative of two independent experiments (D2).

FIG. 3I shows the time course effect of caspase inhibition on COMPOUND-JP-induced LC3 processing and JNK activation in KO99L cells. QVD-OH is used at 20.0 μM. All Western blot data are representative of at least three independent experiments.

FIG. 4 shows the result that targeting LAT1 function interferes in vitro and in vivo with mTORC1 activation

FIG. 5 shows the participation of the Induced Stress Response to the action of COMPOUND-JP

FIG. 6 shows the molecular characterization of the Induced Stress Response mobilized by COMPOUND-JP.

FIG. 7 shows the characterization of a COMPOUND-JP-resistant variant.

FIG. 7A shows the analysis of cell viability through a WST-1 assay after 48 h of culture with increasing concentrations of COMPOUND-JP (mean of five independent experiments performed in quaduplicates+/−SEM; Student's t test).

FIG. 7B shows the analysis of cell death through PI staining, after 48 h of culture with increasing concentrations of COMPOUND-JP (mean of at least three independent experiments performed in quadruplicates; mean+/−SEM, Student's t test).

FIG. 7C shows the Western blot analysis of CHOP induction and S6RP phosphorylation in the resistant variant, compared to parental cells. Data are representative of at least three independent experiments.

FIG. 8 shows the combination studies between COMPOUND-JP and chemotherapeutic drugs FIG. 8A-B shows the result that KO99L cells were incubated with sub-optimal concentrations of COMPOUND-JP in combination with rapamycin, PI-103, KU0063794, doxorubicin, dexamethasone (DXM), velcade, or L-Asparaginase (L-asp). Viability was measured after 48 h by a WST-1 assay. Results are the means+/−s.e.m of 3 independent experiments. P-values were calculated using ANOVA followed by Tukey's Multiple comparison test.

FIG. 8A shows the synergism between drugs was analysed using the Chou-Talalay method. Heat maps of expression of combination index (CI).

FIG. 8B shows the isobolograms of combination effects. Upper right boxed numbers indicate the % of viable cells.

FIGS. 9D and 9E show the result that human cord blood mononuclear cells were incubated with indicated doses of COMPOUND-JP for 48 h before DAPI staining and Facs quantification of living cells. The cell death analysis (B) and the proliferative response (C) of resting or anti-CD3 (48 h, 1.0 µg/ml)-activated human Peripheral Blood Lymphocytes' from healthy donors (n=3) are shown. STS=staurosporine (1.0 µM) is a positive inducer of cell death.

FIG. 9F shows the viability of normal human cord blood cells in the presence of COMPOUND-JP (48 h) analyzed after DAPI staining and facs quantification of living cells.

In FIG. 16, the size of tumor in each treatment group was shown with a bar graph. Group 1 is a control group, Groups 2 to 4 are a group in which COM-JP was intraperitoneally administered alone at 3.1, 12.5, and 50 mg/kg weight/day every day for 4 weeks, Group 5 is a group in which CDDP was intraperitoneally administered alone at 2.5 mg/kg/day three times on day 0, day 6, and day 13, Groups 6 to 8 are a group in which Groups 2 to 4 and Group 5 were combined to be administered in combination, and Group 9 is a group in which COM-JP was orally administered at 300 mg/kg/day every day for 4 weeks.

DESCRIPTION OF EMBODIMENTS

<<Active Ingredient>>

Figure 1A:
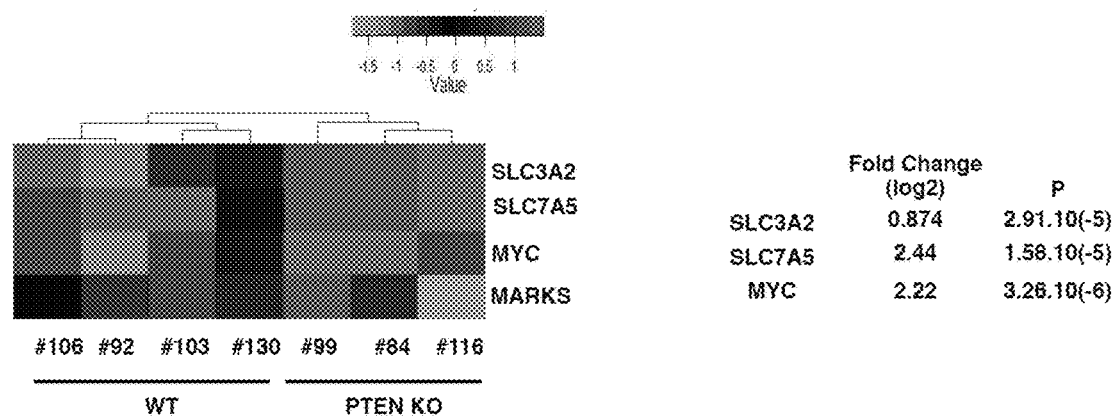
FIG. 1A shows the heatmap analysis of gene expression between PTEN-KO tumors (n=4) and normal murine thymocytes (n=3). The fold change expression values (log 2) are displayed together with the p values.

A LAT1 inhibitor according to the present invention including an aromatic amino acid derivative represented by the following compound 1 to 10 or its pharmacologically acceptable salt as an active ingredient.

A compound 1 is an aromatic amino acid derivative represented by formula (I) or its pharmacologically acceptable salt:

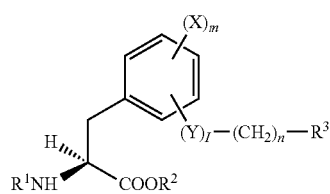

wherein, X is a halogen atom, an alkyl group or alkoxy group,
Y is O or NH,
l is 0 or 1,
m is 0, 1 or 2,
n is an integer of 0-5,
$R^1$ is a hydrogen atom or an amino-protecting group,
$R^2$ is a hydrogen atom or an alkyl, aralkyl or aryl group,
$R^3$ is {circle over (1)} a halogen atom, {circle over (2)} an aroylamino group in which the amino moiety may be optionally substituted with lower alkyl, {circle over (3)} a phenyl group substituted with phenyl, phenoxy, pyridyl, pyrimidinyl or quinolyl in which each substituent on the phenyl group may be further substituted with halogen atom, cyano, hydroxy, carboxy, lower alkoxy, lower alkoxycarbonyl, phenyl, di(lower)alkylamino or thiomorpholinyl, {circle over (4)} a naphthyl or tetrahydronaphthyl group, among which the naphthyl group is optionally substituted with hydroxy, lower alkoxy or di(lower)alkylamino, in which the di(lower)alkylamino may be further substituted with halogen atom or hydroxy, provided that when $R^3$ is unsubstituted naphthyl group, then n is 0 or 2, and that when $R^3$ is a hydroxy substituted naphthyl, then X is chlorine atom and m is not 0, {circle over (5)} an unsaturated mono-cyclic heterocyclic group containing N, O and/or S substituted with lower alkyl, phenyl, naphthyl or tetrahydroquinolyl, in which each substituent on the mono-cyclic heterocyclic group may be further substituted with halogen atom, hydroxy or phenyl, provided that m is 1 or 2 and l is 1 in this case, {circle over (6)} an unsaturated or partially saturated condensed heterocyclic group containing N, O and/or S, optionally substituted with oxo, carboxy, amino, lower alkyl, lower alkoxy, cycloalkyl, di(lower)alkylamino, lower alkoxycarbonyl, di(lower)alkylcarbamoyl, phenyl or saturated or unsaturated mono-cyclic heterocyclic group containing N, O and/or S, in which each substituent on the condensed heterocyclic group may be further substituted with halogen atom, hydroxy, lower alkyl, lower alkoxy, phenyl, di(lower)alkylamino, lower alkanoyloxy, bis[halo(lower)alkyl]amino or N-(lower)alkyl-N-hydroxy-(lower)alkylamino, provided that m is 1 or 2 in this case.

A compound 2 is an aromatic amino acid derivative represented by formula (I) or its pharmacologically acceptable salt:

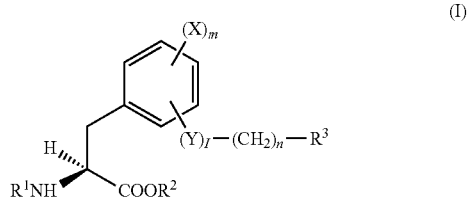

wherein, X is a halogen atom, an alkyl group or alkoxy group,
Y is O or NH,
l is 0 or 1,
m is 0, 1 or 2,
n is an integer of 0-5,
$R^1$ is a hydrogen atom or, t-butoxycarbonyl or trifluoroacetyl,
$R^2$ is a hydrogen atom or an alkyl group,
$R^3$ is {circle over (1)} a bromine atom, {circle over (2)} an aroylamino group in which the amino moiety may be optionally substituted with lower alkyl, {circle over (3)} a phenyl group substituted with phenyl, phenoxy, pyridyl, pyrimidinyl or quinolyl group in which each substituent on the phenyl group may be further substituted with halogen atom or, cyano, hydroxy, carboxy, lower alkoxy, lower alkoxycarbonyl, phenyl, di(lower) alkylamino or thiomorpholinyl, provided that X is chlorine atom, ④ a naphthyl or tetrahydronaphthyl group, among which the naphthyl group is optionally substituted with hydroxy, di(2-hydroxyethyl)amino or di(2-(2-chloroethyl)amino) group, provided that when $R^3$ is unsubstituted naphthyl group, then n is 0 or 2, and that when $R^3$ is a hydroxy substituted naphthyl, then X is chlorine atom and m is 2 in this case, ⑤ an unsaturated mono-cyclic heterocyclic group containing N, O and/or S substituted with phenyl, naphthyl or tetrahydroquinolyl, in which each substituent on the mono-cyclic heterocyclic group may be further substituted with halogen atom or, hydroxy or phenyl, provided that X is chlorine atom, m is 2 and l is 1 in this case.

A compound 3 is the aromatic amino acid derivative according to the preceding compound 2 or its pharmacologically acceptable salt, wherein the unsaturated mono-cyclic heterocyclic group in the class {circle over (5)} for $R^3$ is a 5- or 6-membered heterocyclic group containing N, or containing N and O or containing N and S.

A compound 4 is the aromatic amino acid derivative according to the preceding compound 2 or 3, or its pharmacologically acceptable salt, wherein the unsaturated mono-cyclic heterocyclic group in the class {circle over (5)} for $R^3$ is pyridyl, oxazolyl or thiazolyl.

A compound 5 is the aromatic amino acid derivative according to the preceding compound 2 to 4 or its pharmacologically acceptable salt, wherein $R^1$ is a hydrogen atom.

A compound 6 is the aromatic amino acid derivative according to the preceding compound 2 to 4 or its pharmacologically acceptable salt, wherein $R^1$ is trifluoroacetyl or t-butoxycarbonyl group.

A compound 7 is the aromatic amino acid derivative according to the preceding compound 2 or its pharmacologically acceptable salt, wherein, $R^3$ is ③ a phenyl group substituted with
  phenyl, phenoxy, pyridyl, pyrimidinyl or quinolyl group in which each substituent on the phenyl group may be further substituted with halogen atom or, hydroxyl or di(lower)alkylamino group, provided that X is chlorine atom, ④ a naphthyl group optionally substituted with hydroxy, provided that when $R^3$ is a hydroxy substituted naphthyl, then X is chlorine atom and m is 2, ⑤ an unsaturated mono-cyclic heterocyclic group containing N and O substituted with phenyl or naphthyl group, in which each substituent on the mono-cyclic heterocyclic group may be further substituted with hydroxyl group, provided that X is chlorine atom, m is 2 and l is 1 in this case.

A compound 8 is the aromatic amino acid derivative according to the preceding compound 2 or its pharmacologically acceptable salt, wherein, $R^3$ is ③ a phenyl group substituted with
  phenyl or pyridyl group in which each substituent on the phenyl group may be further substituted with halogen atom or di(lower)alkylamino group, provided that X is chlorine atom, ④ a naphthyl group optionally substituted with hydroxy group, provided that when $R^3$ is a hydroxy substituted naphthyl, then X is chlorine atom and m is 2.

A compound 9 is the aromatic amino acid derivative according to the preceding compound 2 or its pharmacologically acceptable salt, wherein, $R^3$ is ③ a phenyl group substituted with
  phenoxy substituted with di(lower)alkylamino, provided that X is chlorine atom, ④ a naphthyl group, provided that n is 0 or 2, ⑤ an unsaturated mono-cyclic heterocyclic group containing N and O substituted with naphthyl group.

A compound 10 is the aromatic amino acid derivative according to the preceding compound 2 to 9 or its pharmacologically acceptable salt, wherein X is a chlorine or iodine atom.

COMPOUND-JP that is a LAT1 inhibitor according to the present invention is O-(5-amino-2-phenylbenzoxazole-7-yl)methyl-3,5-dichloro-L-tyrosine represented by formula (II) or its pharmacologically acceptable salt. This compound 11 or its pharmacologically acceptable salt is particularly preferable for the anticancer agent composition of the present invention.

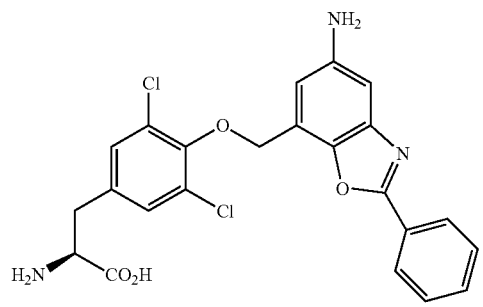

(II)

Now, as for the "pharmacologically acceptable salt", for example, alkali metal salt (sodium salt, potassium salt, etc.), alkaline earth metal salt (calcium salt, magnesium salt, etc.), ammonium salt, salt with an organic base (trimethylamine, triethylamine, pyridine, picoline, dicyclohexylamine, dibenzylethylenediamine, etc.), salt with an organic acid (acetic acid, benzoic acid, succinic acid, fumaric acid, maleic acid, lactic acid, citric acid, tartaric acid, gluconic acid, methanesulfonic acid, benzenesulfonic acid, formic acid, p-toluenesulfonic acid, trifluoroacetic acid etc.), salt with an inorganic acid (hydrochloric acid, hydrobromic acid, sulfuric acid, phosphoric acid, etc.), and salt with an amino acid (arginine, aspartic acid, glutamic acid, etc.) can be mentioned.

This compound and its salt may be in a form of a hydrate or a solvate such as ethanolate. In addition, in order to improve the water solubility, the compounds or its salt is preferably inclusion complex of cyclodextrin (for example, β-cyclodextrin). Here, the compound or its salt: cyclodextrin (mass ratio) is preferably 1:10 to 70, more preferably 1:20 to 50, particularly preferably 1:25 to 35.

LAT1 inhibitors in the present invention includes anti LAT1 antibodies. Such anti LAT1 antibodies are not particularly limited as long as they can specifically recognize LAT1; examples of which may include anti-h LAT1 monoclonal antibody, anti-mouse LAT1 monoclonal antibody, anti-h LAT1 polyclonal antibody and anti-mouse LAT1 polyclonal antibody.

Herein, anti-LAT1 antibodies are not particularly limited as along as they take LAT1 as antigens and bind to such antigens. Therefore, mouse antibodies, rat antibodies, rabbit antibodies, sheep antibodies and the like may appropriately be used.

Also, hybridomas producing monoclonal antibodies can be produced, basically using known techniques as follows. Specifically, monoclonal antibodies may be produced by using desired antigens and/or cells expressing such desired antigens as sensitized antigens, immunizing them according to conventional immunization methods, fusing the obtained immunocytes with known parent cells by means of conventional cell fusion methods and screening monoclonal antibody-producing cells (hybridomas) by means of conventional screening methods. Production of hybridomas may be carried out, for example, according to the method of Milstein et al. (Kohler, G. and Milstein, C., Methods Enzymol. (1981) 73: 3-46), and the like. In producing anti-LAT1 monoclonal antibodies, LAT1 or fragments of the protein may be used as antigens; thus, LAT1 or cells expressing fragments of the protein may also be used as antigens. LAT1 or fragments of the protein may be obtained, for example, according to the method described in Molecular Cloning: A Laboratory Manual, $2^{nd}$. Ed., Vols. 1-3, Sambrook, J. et al, Cold Spring Harbor Laboratory Press, New York, 1989. Also LAT1 or cells expressing fragments of the protein may be obtained according to the method described in Molecular Cloning: A Laboratory Manual, $2^{nd}$. Ed., Vols. 1-3, Sambrook, J. et al, Cold Spring Harbor Laboratory Press, New York, 1989.

The polyclonal antibody can be acquired by administering an antigen, along with a commercially available adjuvant (for example, Freund's complete or incomplete adjuvant), to an animal subcutaneously or intraperitoneally about 2 to 4 times at intervals of 2 to 3 weeks (the antibody titer of partially drawn serum has been determined by a known antigen-antibody reaction and its elevation has been confirmed in advance), collecting whole blood about 3 to about 10 days after final immunization, and purifying the antiserum. As the animal to receive the antigen, mammals such as rats, mice, rabbits, goat, guinea pigs, and hamsters can be mentioned.

<<Route of Administration>>

The anticancer agent composition of the present invention can be administered by an oral or transdermal route or by injection.

Tablets, granules and capsules for oral administration may contain conventional additives, for example, a binding agent (e.g. syrup, gum arabic, gelatin, sorbitol, traganth or polyvinylpyrrolidone); filling agent (e.g. lactose, sugar, corn starch, calcium phosphate, sorbitol or glycine); lubricant (e.g. magnesium stearate, talc, polyethyleneglycol or silica); disintegrant (e.g. potato starch) or wetting agent (e.g. sodium lauryl sulfate). The tablets, granules and capsules may be coated by a known method in the field of conventional formulation.

Liquid preparation for oral administration may be in a form of aqueous or oily suspension, solution, emulsion, syrup or elixyl, or freezed-dry preparation which is dissolved in water or in a suitable solvent before use. The liquid preparation may contain conventional additives, for example, suspending agent (e.g. sorbitol, syrup, methylcellulose, glucose syrup, gelatin hydrogenated edible fat; emulsifying agent (e.g. lecithin, sorbitan monooleate or gum arabic); hydrophobic excipient (e.g. almond oil, fractionated coconuts oil or glycerin, oily ester such as propyleneglycol or ethyl alcohol; preserving agent (e.g. methyl or propyl p-hydroxybenzoate or sorbic acid) and flavoring agent or coloring agent.

In the preparation for transdermal administration, the active ingredient may be in a form of cream, lotion or ointment. The cream or ointment preparation which can be used as a medicament can be prepared by a method well known in the art.

The preparation for injection can be prepared by suspending or dissolving the compound or its salt in a proper medium. Adjuvants such as topical anesthetics, preserving agents and buffers may be contained in the preparation for injection.

<<Dosage>>

Dosage of the anticancer agent composition of the present invention, which is not limited, may be properly controlled depending on various factors including age, body weight, systemic healthy condition and sexuality of a patient, time of administration, administration route and severity of a disease, but, for example, it is usually proper to administer about 10-5000 mg, preferably about 100-3000 mg per day for an adult, in 1-5 times.

A dose (mass ratio) of the LAT1 inhibitor according to the present invention, and one or more agents selected from the group consisting of an alkylating agent, a platinum-based antineoplastic agent, an anti-metabolite, a topoisomerase inhibitor, an anti-microtubule polymerizing agent, a hormonal agent, an anti-microtubule depolymerizing agent, an anticancer antibiotic, and a molecular targeted agent, which is not limited, may be properly controlled depending on various factors including age, body weight, systemic healthy condition and sexuality of a patient, time of administration, administration route and severity of a disease, but, for example, estimating the dose used by each singly per day for an adult at 1, it is usually proper that the mass ratio of the LAT1 inhibitor, and one or more agents selected from the group consisting of an alkylating agent, a platinum-based antineoplastic agent, an anti-metabolite, a topoisomerase inhibitor, an anti-microtubule polymerizing agent, a hormonal agent, an anti-microtubule depolymerizing agent, an anticancer antibiotic, and a molecular targeted agent is 0.1:1 to 1:0.1 per day for an adult.

EXAMPLE

The manufacturing method of the present compound will be explained in detail with the following manufacturing examples, and the action thereof as a pharmaceutical composition will be explained in detail with the following test examples, the results and the consideration thereof. A test example of preceding inclusion complex of cyclodextrin is explained at Preparation 32.

<<Preparation>>

(Preparation 1)

1) A solution of 2-naphthoyl chloride (5.70 g, 29.9 mmol) in tetrahydrofuran (60 ml) was added dropwise to a mixture of 28% aqueous ammonia (20 ml) and tetrahydrofuran (30 ml) with stirring under ice cooling, and the mixture was stirred at room temperature for 4 hrs. The solvent was distilled off under reduced pressure, and water was added to the residue. The precipitates were collected by filtration and dried to give 2-carbamoylnaphthalene (2.68 g, 52%) as a colorless solid.

IR (Nujol): 3378, 3194, 1685, 1655 $cm^{-1}$; APCI-MS m/z: 172 $[M+H]^+$.

2) A mixture of 2-carbamoylnaphthalene (2.64 g, 15.4 mmol) and ethyl 4-chloroacetoacetate (2.06 g, 12.5 mmol) was stirred at 160° C. for 1 hr. and then diluted with ethyl acetate (200 ml) at room temperature. The solution was washed with saturated sodium bicarbonate aqueous solution and brine in turn, and then dried. The solvent was distilled off under reduced pressure, and the residue was purified by column chromatography on silica gel (n-hexane/ethyl acetate=8-4) to give ethyl ester of [2-(2-naphthyl)oxazol-4-yl]acetic acid (459 mg, 13%) as yellow crystals.

m.p.: 61.5-64° C.; IR (Nujol): 1737, 1591 cm$^{-1}$; $^{1H\text{-}NMR}$ (CDCl$_3$): δ 1.31 (3H, t, J=7.1 Hz), 3.73 (2H, d, J=1.1 Hz), 4.24 (2H, q, J=7.1 Hz), 7.49-7.57 (2H, m), 7.76 (1H, t, J=1.1 Hz), 7.82-7.95 (3H, m), 8.11 (1H, J=1.7, 8.7 Hz), 8.58 (1H, br d, J=1.1 Hz); APCI-MS m/z: 282 [M+H]$^+$.

3) A solution of ethyl ester of [2-(2-naphthyl)-oxazol-4-yl]acetic acid (434 mg, 1.54 mmol) in tetrahydrofuran (20 ml) was added dropwise to a suspension of lithium aluminium hydride (66 mg, 1.74 mmol) in tetrahydrofuran (15 ml) with stirring under ice cooling and the mixture was stirred at the same temperature for 2.5 hrs. To the reaction mixture were added water (0.1 ml), 15% aqueous solution of sodium hydroxide (0.1 ml), water (0.3 ml) and sodium sulfate (3 g) in turn. Insoluble materials were filtered off, and the solvent was distilled off under reduced pressure. The residue was purified by column chromatography on silica gel (n-hexane/ethyl acetate=2-1) to give 2-[2-(2-naphthyl)-oxazol-4-yl]ethano-1 (323 mg, 88%) as pale yellow crystals.

m.p.: 96-98° C.; IR (Nujol): 3466, 1591, 1543 cm$^{-1}$; $^{1H\text{-}NMR}$ (CDCl$_3$): δ 2.85-2.90 (2H, m), 2.93 (1H, t, J=6.0 Hz), 3.99 (2H, q, J=6.0 Hz), 7.50-7.57 (2H, m), 7.58 (1H, t, J=1.0 Hz), 7.82-7.96 (3H, m), 8.10 (1H, dd, J=1.7, 8.6 Hz), 8.52 (1H, br); APCI-MS m/z: 240 [M+H]$^+$.

(Preparation 2)

1) A mixture of isonicotinic acid chloride hydrochloride (2.34 g, 13.2 mmol), triethylamine (1.83 ml, 13.2 mmol) and tetrahydrofuran (10 ml) was added dropwise to a mixture of methyl ester of 3-amino-2-hydroxybenzoic acid hydrochloride (2.0 g, 12.0 mmol), N,N'-dimethylaniline (3.04 ml, 24.0 mmol) and tetrahydrofuran (20 ml) with stirring under ice cooling, and the mixture was stirred at the same temperature for 2 hrs. The reaction mixture was diluted with methylene chloride (200 ml), washed with water and brine in turn and then dried. The solvent was distilled off under reduced pressure, and the residue was purified by column chromatography on amine silica gel (Chromatolex (trademark) NH) (n-hexane/ethyl acetate=4 and chloroform/ethyl acetate=1) to give methyl ester of 2-hydroxy-3-isonicotinoylaminobenzoic acid (2.37 g, 73%) as pale yellow crystals.

m.p.: 157-158° C.; IR (Nujol): 3423, 1669, 1555, 1542 cm$^{-1}$; APCI-MS m/z: 273 [M+H]$^+$.

2) A mixture of methyl ester of 2-hydroxy-3-isonicotinoylamino-benz-oic acid (500 mg, 1.84 mmol), p-toluenesulfonic acid mono-hydrate (349 mg, 1.84 mmol) and xylene (20 ml) was heated under reflux for 14 hrs. and then p-toluenesulfonic acid mono-hydrate (349 mg, 1.84 mmol) was further added and refluxed under heating for 2 hrs. The reaction mixture was cooled with ice, and ethyl acetate and 10% aqueous potassium carbonate solution were added thereto. The organic phase was separated, washed with water and brine in turn and then dried. The solvent was distilled off under reduced pressure, and the residue was triturated with a mixture of n-hexane/diisopropyl ether (4/1), filtered and dried to give methyl ester of [2-(4-pyridyl)-benzoxazol-7-yl]carboxylic acid (382 mg, 82%) as pale yellow crystals.

m.p.: 149-151° C.; IR (Nujol): 1725 cm$^{-1}$; APCI-MS m/z: 255 [M+H]$^+$.

3) Lithium aluminium hydride (53 mg, 1.42 mmol) was added to a solution of methyl ester of [2-(4-pyridyl)-benzoxazol-7-yl]carboxylic acid (360 mg, 1.42 mmol) in tetrahydrofuran (15 ml) with stirring under ice cooling in 10 min. and the mixture was stirred at the same temperature for 0.5 hrs. To the reaction mixture were added dropwise at the same temperature 10% aqueous tetrahydrofuran (2 ml) and 30% aqueous solution of sodium hydroxide (0.5 ml) in turn, and the mixture was stirred at room temperature for 2 hrs. The resultant insoluble materials were filtered off, and the solvent was distilled off from the filtrate under reduced pressure. The residue was diluted with ethyl acetate and washed with water and brine in turn and then dried. The solvent was distilled off under reduced pressure, and the resultant crystals were triturated with a mixture of n-hexane/diisopropyl ether (1/1), filtered and dried to give [2-(4-pyridyl)-benzoxazol-7-yl]methanol (216 mg, 67%) as colorless crystals.

m.p.: 146-147° C.; IR (Nujol):3221, 1595, 1541 cm$^{-1}$; $^{1H\text{-}NMR}$ (CDCl$_3$): δ 2.35 (1H, t, J=5.9 Hz), 5.08 (2H; d, J=5.9 Hz), 7.38-7.51 (2H, m), 7.76 (1H, dd, J=1.4, 7.8 Hz), 8.07-8.09 (2H, m), 8.78-8.81 (2H, m); APCI-MS m/z: 227 [M+H]$^+$.

(Preparation 3)

1) Triethylamine (7.1 ml, 51 mmol) was added dropwise at room temperature to a suspension of 3-hydroxybenzaldehyde (1.72 g, 14.1 mmol), 4-methoxyphenylboronic acid (3.16 g, 20.8 mmol), molecular sieves 4A powder (1.95 g) and copper (II) acetate (2.96 g, 16.3 mmol) in methylene chloride (100 ml), and the mixture was stirred for 27.5 hrs. The reaction mixture was diluted with ethyl acetate (200 ml), and the insoluble materials were filtered off and washed with ethyl acetate. The filtrate and washings were combined, washed with 10% hydrochloric acid and brine in turn and dried. The solvent was distilled off under reduced pressure, and the residue was purified by column chromatography on silica gel (n-hexane/ethyl acetate=7) to give 3-[(4-methoxy)phenoxy]benzaldehyde (596 mg, 19%) as a pale brown oil.

IR (Neat): 2835, 1699, 1584, 1504 cm$^{-1}$; GCEI-MS m/z: 228 (Mt).

2) Sodium borohydride (158 mg, 4.18 mmol) was added to a solution of 3-[(4-methoxy)phenoxy]benzaldehyde (573 mg, 2.51 mmol) in ethanol (10 ml) with stirring under ice cooling, and the mixture was stirred at room temperature for 25 min. The solvent was distilled off from the reaction mixture, and the residue was diluted with ethyl acetate, washed with water and brine in turn and dried. The solvent was distilled off and the residue was purified by column chromatography on silica gel (chloroform/ethyl acetate=20) to give 3-[(4-methoxy)phenoxy]benzyl alcohol (469 mg, 81%) as a colorless oil.

IR (Neat): 3356, 1611, 1586, 1504 cm$^{-1}$; $^{1H\text{-}NMR}$ (CDCl$_3$): δ 1.67 (1H, t, J=5.3 Hz), 3.81 (3H, s), 4.65 (2H, br.d, J=4.6 Hz), 6.84-6.91 (3H, m), 6.93-7.06 (4H, m), 7.28 (1H, t, J=7.9 Hz); GCEI-MS m/z: 230 (M$^+$).

(Preparation 4)

3-[(4-methoxy)phenoxy]benzyl alcohol obtained in Preparation 3 was subjected to demethylation reaction by a conventional method to give 3-[(4-hydroxy)phenoxy]benzyl alcohol as a pale yellow oil.

IR (Neat): 3350, 1603, 1585, 1505 cm$^{-1}$; $^{1H\text{-}NMR}$ (CDCl$_{3+}$ DMSO-d$_6$): δ 3.57 (1H, t, J=5.9 Hz), 4.60 (2H, d, J=5.5 Hz), 6.79-6.90 (5H, m), 6.92-6.96 (1H, m), 6.98-7.04 (1H, m), 7.24 (1H, t, J=7.8 Hz), 8.49 (1H, s); ESI-MS m/z: 215 [M–H]$^-$.

(Preparation 5)

A solution of n-butyl lithium in hexane (1.5M; 8.9 ml, 13.4 mmol) was added dropwise to a solution of 2-bromo-6-methoxynaphthalene (3.0 g, 12.7 mmol) in tetrahydrofuran (45 ml) under argon atmosphere at −60° C. and the mixture was stirred at the same temperature for 70 min. To the mixture was added tri-n-butylborate (5.2 ml, 19.0 mmol) and the mixture was stirred at the same temperature for 1 hr. and then at 5° C. for 1.5 hrs. To the reaction mixture was added dropwise 20% hydrochloric acid (13 ml) at 5° C., and water was added thereto. The mixture was extracted with ethyl acetate. The organic layer was washed with water and brine in turn and dried. The solvent was distilled off under reduced pressure, and the residue was triturated with ethyl acetate and diethyl ether, filtered and dried to give (2-methoxy)-6-naphthalene boronic acid (1.50 g, 59%) as a colorless solid.

m.p.: 301-311° C.; IR (Nujol): 3290, 1625 cm$^{-1}$; $^{1}H$-$NMR$ (DMSO d$_6$): δ 3.87 (3H, s), 7.14 (1H, dd, J=2.6, 9.0 Hz), 7.28 (1H, d, J=2.6 Hz), 7.74 (1H, d, J=8.2 Hz), 7.79-7.84 (2H, m), 8.06 (2H, s), 8.28 (1H, s).

(Preparation 6)

A solution of boron tribromide in methylene chloride (1.0 M; 7 ml, 7 mmol) was added dropwise to a suspension of [2-(3-methoxyphenyl)-benzox-azol-7-yl]methanol (457 mg, 1.79 mmol) in methylene chloride (10 ml) at −78° C., and the mixture was stirred at the same temperature for 1 hr. After the removal of the cooling bath, the mixture was stirred at room temperature for 2.5 hrs. The reaction mixture was poured into ice-water (50 ml), and the organic layer was separated. The aqueous layer was extracted with ethyl acetate. The organic layers were combined and dried, and the solvent was distilled off under reduced pressure. The residue was purified by flash column chromatography on silica gel (n-hexane/ethyl acetate=3-1) to give 7-bromomethyl-2-(3-hydroxyphenyl)-benzoxazole (535 mg, 98%) as a brown solid.

m.p.: 225-228° C.; IR (Nujol): 3147, 1602, 1559 cm$^{-1}$; $^{1}H$-$NMR$ (DMSO-d$_6$): δ 5.02 (2H, s), 7.04 (1H, ddd, J=0.9, 2.4, 8.0 Hz), 7.36-7.54 (3H, m), 7.62-7.71 (2H, m), 7.78 (1H, dd, J=1.2, 8.0 Hz), 10.0 (1H, s); APCI-MS m/z: 304/306 [M+H]$^+$.

(Preparation 7)

A solution of n-butyl lithium in hexane (1.5M; 3.72 ml, 5.6 mmol) was added dropwise to a solution of 5-bromobenzo[b]furan (1.0 g, 5.0 mmol) in tetrahydrofuran (10 ml) under argon atmosphere at −60° C. and the mixture was stirred at the same temperature for 30 min. To the mixture was added trimethyl borate (0.69 ml, 6.0 mmol) and temperature of the mixture was raised to room temperature in 4 hrs. Water (5 ml) was added to the reaction mixture at 5° C. and tetrahydrofuran was distilled off under reduced pressure. To the residue was added 1N hydrochloric acid (pH 1) and the mixture was extracted with ethyl acetate. The organic layer was washed with brine and dried. The solvent was distilled off and the residue was triturated with a mixture of n-hexane/diethyl ether, filtered and dried to give 5-benzo[b]furan boronic acid (551 mg) as a pale brown solid.

(Preparation 8)

1) A mixture of ethyl ester of 2-bromobenzothiazole-7-carboxylic acid (572 mg, 2.00 mmol), piperidine (5 ml) and ethanol (1 ml) was stirred at 70-75° C. for 2.5 hrs. Diethyl ether (15 ml) was added to the mixture at room temperature and the precipitates were filtered off and washed with diethyl ether. The filtrate and washings were combined and the solvent was distilled off under reduced pressure. The residue was purified by column chromatography on silica gel (chloroform) to give ethyl ester of 2-piperidinobenzothiazole-7-carboxylic acid (526 mg, 90%) as pale orange crystals.

m.p.: 88-89° C.; IR (Nujol): 1791, 1595, 1541 cm$^{-1}$; APCI-MS m/z: 291 [M+H]$^+$ 2) Ethyl ester of 2-piperidinobenzothiazole-7-carboxylic acid (475 mg, 1.64 mmol) was reduced by using lithium aluminium hydride as in Preparation 2-3) to give 2-piperidinobenzothiazole-7-methanol (375 mg, 91%) as pale yellow crystals.

m.p.: 107-108° C.; IR (Nujol): 3261, 3200, 1595, 1541 cm$^{-1}$; APCI-MS m/z: 249 [M+H]$^+$.

(Preparation 9)

1) Tetrakis(triphenylphosphine)palladium (144 mg, 0.125 mmol) and a solution of sodium bicarbonate (630 mg, 7.50 mmol) in degassed water (10 ml) were added in turn to a solution of ethyl ester of 2-bromobenzothiazole-7-carboxylic acid (715 mg, 2.50 mmol) and phenyl boronic acid (341 mg, 2.8 mmol) in degassed dimethoxyethane (20 ml) and the mixture was stirred at 50° C. for 10 min. Copper (I) iodide (24 mg, 0.125 mmol) was added to the mixture at room temperature and the mixture was heated under reflux for 4 hrs. Dimethoxyethane was distilled off under reduced pressure and the residue was extracted with ethyl acetate. The organic layer was washed with brine and dried and the solvent was distilled off under reduced pressure. The residue was purified by column chromatography on silica gel (n-hexane/ethyl acetate=10) to give ethyl ester of 2-phenylbenzothiazole-7-carboxylic acid (500 mg, 70%) as colorless crystals.

m.p.: 86.5-87.5° C.; IR (Nujol): 1716 cm$^{-1}$; APCI-MS m/z: 284 [M+H]$^+$.

2) Ethyl ester of 2-phenylbenzothiazole-7-carboxylic acid (425 mg, 1.50 mmol) was reduced by using lithium aluminium hydride as in Preparation 2-3) to give 2-phenylbenzothiazole-7-methanol (340 mg, 94%) as colorless crystals.

m.p.: 101-102° C.; IR (Nujol): 3241, 1572, 1507 cm$^{-1}$; APCI-MS m/z: 242 [M+H]$^+$.

(Preparation 10)

1) 2,6-Lutidine (1.83 ml, 15.7 mmol) and trifluoro-methanesulfonic anhydride (3.67 g, 13 mmol) were added dropwise in turn to a solution of methyl ester of 5-chloro-3-nitrosalicylicacid (2.32 g, 10.0 mmol) in methylene chloride (25 ml) with stirring under ice cooling and the mixture was stirred under ice cooling for 0.5 hrs. Methylene chloride (20 ml) and ice water (30 ml) were added to the reaction mixture and the aqueous layer was separated and extracted with methylene chloride. The organic layers were combined, washed with water and dried. The solvent was distilled off under reduced pressure and the residue was purified by column chromatography on silica gel (n-hexane/ethyl acetate=10) to give methyl ester of 5-chloro-2-trifluoromethanesulfonyloxy-3-nitrobenzoic acid (3.33 g, 91%) as a pale yellow oil.

IR (Neat): 3088, 2961, 1742, 1603, 1552 cm$^{-1}$; APCI-MS (m/z): 381 [M+NH$_4$]$^+$.

2) Triethylamine (0.33 ml, 2.37 mmol) and isoindoline (0.27 ml, 2.38 mmol) were added in turn to a solution of methyl ester of 5-chloro-2-trifluoromethanesulfonyloxy-3-nitrobenzoic acid (820 mg, 2.25 mmol) in dimethyl sulfoxide (5 ml) and the mixture was stirred at room temperature for 1 hr. The reaction mixture was cooled with ice and ice water (50 ml) was added thereto. The mixture was stirred and the precipitates were filtered, washed with water and dried. The resultant yellow crystals were purified by column chromatography on silica gel (n-hexane/ethyl acetate=15) to give methyl ester of 5-chloro-2-(1,2,3,4-tetrahydroisoquinolinio)-3-nitrobenzoic acid (608 mg, 81%) as yellow crystals.

m.p.: 114-115° C.; IR (Nujol): 1743, 1705, 1603, 1589, 1529, 1503 cm$^{-1}$; APCI-MS m/z: 333[M+H]$^+$.

3) 10% Palladium carbon (water 51.7%, 190 mg) was added to a solution of methyl ester of 5-chloro-2-(1,2,3,4-tetrahydroisoquinolinio)-3-nitrobenzoic acid (590 mg, 1.77 mmol) in methanol (6 ml) and tetrahydrofuran (9 ml) and, the mixture was stirred under hydrogen atmosphere at room temperature for 24 hrs. The catalyst was removed by filtration and the filtrate was concentrated to about 5 ml volume. The precipitating crystals were collected by filtration. To the crystals were added ethyl acetate (50 ml) and water (30 ml) and the mixture was adjusted to pH 8-9 by adding saturated sodium bicarbonate aqueous solution and extracted with ethyl acetate. The organic extract was washed with brine and dried. The solvent was distilled off under reduced pressure to give methyl ester of 1,2,3,4-tetrahydronaphthalene[1,2-a]ben-zimidazole-7-carboxylic acid (96 mg, 20%) as pale yellow crystals.

m.p.: 152-153° C.; IR (Nujol): 1710, 1627, 1611, 1589, 1579, 1551. cm$^{-1}$; APCI-MS (m/z): 265[M+H]$^{+}$.

4) Methyl ester of 1,2,3,4-tetrahydronaphthalene[1,2-a]benzimidazole-7-carboxylic acid (80 mg, 0.30 mmol) was reduced by using lithium aluminium hydride as in Preparation 2-3) to give 1,2,3,4-tetrahydronaphthalene[1,2-a]benzimidazole-7-methanol (67 mg, crude 94%) as a pale grayish white solid. IR (Nujol): 3170, 1615, 1547 cm$^{-1}$; APCI-MS m/z: 237 [M+H]$^{+}$.

(Preparation 11)

1) 3-Biphenylphenylboronic acid (1089 mg, 5.50 mmol), tetrakis(triphenylphosphine)palladium (578 mg, 0.50 mmol) and potassium carbonate (2.07 g, 15.0 mmol) were added in turn to a solution of ethyl ester of 2-chloronicotinic acid (928 mg, 5.00 mmol) in degassed 1,4-dioxane (25 ml) and the mixture was heated under reflux for 18 hrs. Water was added to the mixture and the mixture was extracted with ethyl acetate. The organic layer was washed with water and brine in turn and dried. The solvent was distilled off under reduced pressure and the residue was purified by column chromatography on silica gel (n-hexane/ethyl acetate=5) to give ethyl ester of 2-(3-biphenyl)nicotinic acid (1.411 g, 93%) as a colorless oil.

IR (Neat): 2981, 1722, 1716 cm$^{-1}$; APCI-MS m/z: 304 [M+H]$^{+}$.

2) Ethyl ester of 2-(3-biphenyl)nicotinic acid (1.38 g, 4.55 mmol) was reduced by using lithium aluminium hydride as in Preparation 2-3) to give 2-(3-biphenyl)pyridine-3-methanol (1.115 g, 94%) as colorless crystals.

m.p: 91-93° C.; IR (Nujol): 3265, 1579, 1566 cm$^{-1}$; APCI-MS m/z: 262 [M+H]$^{+}$.

(Preparation 12)

1) 1,2,3,4-Tetrahydroisoquinoline (0.49 ml, 3.9 mmol) and triethylamine (0.47 ml, 3.34 mmol) were added in turn to a solution of ethyl ester of 2-chloronicotinic acid (557 mg, 3.0 mmol) in tetrahydrofuran (17 ml) and the mixture was heated under reflux for 18 hrs. After the mixture was cooled to room temperature, the precipitates were filtered off and the solvent of the filtrate was distilled off under reduced pressure. The residue was dissolved in ethyl acetate, washed with water and brine in turn and dried. The solvent was distilled off under reduced pressure and the residue was purified by column chromatography on amine silica gel (Chromatolex (trademark) NH) (n-hexane/ethyl acetate=19) to give ethyl ester of 2-(1,2,3,4-tetrahydroisoquinolinio)nicotinic acid (529 mg, 62%) as a colorless oil.

IR (Neat): 2979, 1711, 1584, 1555 cm$^{-1}$; APCI-MS m/z: 283 [M+H]$^{+}$.

2) Ethyl ester of 2-(1,2,3,4-tetrahydroisoquinolinio)nicotinic acid (511 mg, 1.81 mmol) was reduced by using lithium aluminium hydride as in Preparation 2-3) to give 2-(1,2,3,4-tetrahydroisoquinolinio)pyridine-3-methanol (386 mg, 89%) as colorless crystals.

m.p.: 95-97° C.; IR (Nujol): 3184, 1595, 1575 cm$^{-1}$; APCI-MS m/z: 241 [M+H]$^{+}$.

(Preparation 13)

1) Methyl ester of 2-(2-methylthiopyrimidine-5-yl)benzoxazole-carboxylic acid was synthesized from 3-aminosalicylic acid hydrochloride and 2-methylthiopyrimidene-5-carboxylic acid chloride hydrochloride according to the method of Preparation 2.

m.p.: 190-191° C.; IR (Nujol): 1719 cm$^{-1}$; APCI-MS m/z: 302 [M+H]$^{+}$.

2) 77% m-Chloroperbenzoic acid (476 mg, 2.12 mmol) was added to a suspension of methyl ester of 2-(2-methylthiopyrimidin-5-yl)benzoxazole-7-carboxylic acid (400 mg, 1.33 mmol) in tetrahydrofuran (10 ml) under ice cooling and the mixture was stirred for 15 min. and then at room temperature for 3 hrs. To the reaction mixture was added dropwise 50% aqueous solution of dimethylamine at room temperature and the mixture was stirred at room temperature for 1 hr. The reaction mixture was cooled with ice and water (25 ml) was added thereto. The mixture was stirred for 15 min. and extracted with ethyl acetate. The organic layer was washed with water and brine in turn and dried. The solvent was distilled off under reduced pressure and the residue was purified by column chromatography on silica gel (chloroform/ethyl acetate=4) to give methyl ester of 2-(2-dimethylaminopyrimidin-5-yl)benzoxazole-7-carboxylic acid (328 mg, 83%) as colorless crystals.

m.p.: 199-201° C.; IR (Nujol): 1719, 1628, 1605 cm$^{-1}$; APCI-MS m/z: 299 [M+H]$^{+}$.

3) Methyl ester of 2-(2-dimethylaminopyrimidin-5-yl)benzoxazole-7-carboxylic acid (480 mg, 1.61 mmol) was reduced by using lithium aluminium hydride as in Preparation 2-3) to give 2-(2-dimethylamino-pyrimidin-5-yl)-benzoxazole-7-methanol (234 mg, 54%) as yellow crystals.

m.p.: 212-215° C.; IR (Nujol): 3283, 1617 cm$^{-1}$; APCI-MS m/z: 271 [M+H]$^{+}$.

(Preparation 14)

1) Methyl ester of 2-[2-[N-2-(hydroxy)ethyl-N-methyl]aminopyrimidin-5-yl]benzoxazole-7-carboxylic acid (322 mg, 74%) was synthesized from methyl ester of 2-(2-methylthiopyrimidin-5-yl)benzoxazole-7-carboxylic acid (400 mg, 1.33 mmol) according to the method of Preparation 13-2).

m.p.: 157-159° C.; IR (Nujol): 3529, 1713, 1626, 1601 cm$^{-1}$; APCI-MS m/z: 329 [M+H]$^{+}$.

2) A hydroxyl group of methyl ester of 2-[2-[N-2-(hydroxy)ethyl-N-methyl]aminopyrimidin-5-yl]benzoxazole-7-carboxylic acid (300 mg, 0.914 mmol) was tetrahydropyranylated by a conventional method to give methyl ester of 2-[2-[N-2-(tetrahydropyran-2-yloxy)ethyl-N-methyl]aminopyrimidin-5-yl]benzoxazole-7-carboxylic acid (286 mg, 69%) as colorless crystals.

m.p.: 126-128° C.; IR (Nujol): 1717, 1625, 1601 cm$^{-1}$; APCI-MS m/z: 413 [M+H]$^{+}$.

3) Methyl ester of 2-[2-[N-2-(tetrahydropyran-2-yloxy)ethyl-N-methyl]aminopyrimidin-5-yl]benzoxazole-7-carboxylic acid (275 mg, 0.667 mmol) was reduced by using lithium aluminium hydride as in Preparation 2-3) to give 2-[2-[N-2-(tetrahydropyran-2-yloxy)ethyl-N-methyl]aminopyrimidin-5-yl]benzoxazole-7-methanol (128 mg, 50%) as colorless crystals.

m.p.: 110-112° C.; IR (Nujol): 3287, 1622, 1603 cm$^{-1}$; APCI-MS m/z: 385 [M+H]$^{+}$.

(Preparation 15)

1) Boron trifluoride ether complex (1.83 ml, 14.86 mmol) was added dropwise to a suspension of sodium borohydride (422 mg, 11.14 mmol) in tetrahydrofuran (30 ml) with stirring under ice cooling in 10 min. To this reaction mixture was added a solution of (±)-2-phenyl-1,4-benzoxa-zin-3-one-8-carboxylic acid (500 mg, 1.86 mmol) in tetrahydrofuran (6 ml) and the mixture was stirred at the same temperature for 5 min. and then at room temperature for 1.5 hrs. The reaction mixture was cooled with ice and water (20 ml) was added dropwise thereto. The mixture was neutralized with saturated sodium bicarbonate solution and then extracted with ethyl acetate. The extract was washed with water and brine in turn and dried. The solvent was distilled off under reduced pressure to give (±)-2-phenyl-1,4-benzoxazine-8-methanol (397 mg, 89%) as a pale orange oil.

IR (Neat): 3375, 1607 cm$^{-1}$.

2) Sodium carbonate (2.90 g, 27.35 mmol) was added to a solution of (±)-2-phenyl-1,4-benzoxazine-8-methanol (600 mg, 2.49 mmol) in diethyl ether (22 ml) with stirring under ice cooling. Trifluoroacetic anhydride (3.86 ml, 27.35 mmol) was added to the mixture and the mixture was stirred at the same temperature for 15 min. and at room temperature for 15 min. The reaction mixture was cooled with ice, poured into ice water and then extracted with ethyl acetate. The extract was washed with water and brine in turn and dried. The solvent was distilled off under reduced pressure. The residue was triturated with diisopropyl ether, filtered and dried to give (±)-4-trifluoroacetyl-8-trifluoro-acetoxymethyl-2-phenyl-1,4-benzoxazine (973 mg, 90%) as colorless crystals.

m.p.: 91-92° C.; IR (Nujol): 1781, 1705 cm$^{-1}$.

3) Glycine buffer (pH 10, 6.33 ml) was added dropwise to a solution of (±)-4-trifluoroacetyl-8-trifluoroacetoxymethyl-2-phenyl-1,4-benzoxazine (953 mg, 2.20 mmol) in methanol (19 ml) at room temperature and the mixture was stirred for 30 min. To the mixture was added water (70 ml) and the mixture was stirred at room temperature for 20 min. and then extracted with ethyl acetate. The extract was washed with water and brine in turn and dried. The solvent was distilled off under reduced pressure to give (±)-4-trifluoroacetyl-2-phenyl-1,4-benzoxazine-8-methanol (793 mg, quantitative yield) as a pale orange oil.

IR (Neat): 3400, 1704 cm$^{-1}$.

(Preparation 16)

(5-Methoxy-2-phenyl)benzo[b]furan-7-carboxylic acid was reduced by using lithium aluminium hydride in a conventional manner to give (5-methoxy-2-phenyl)benzo[b]furan-7-methanol.

m.p.: 150-151° C.

(Preparation 17)

Hydroxy group of 3-hydroxymethylflavone-8-carboxylic acid was acetylated by a conventional method and then the carboxyl group was reduced to give 3-acetoxymethylflavone-8-methanol.

m.p.: 204-206° C.; IR (Nujol): 1739, 1616 cm$^{-1}$; ESI-MS m/z: 337 [M–H]$^-$.

(Preparation 18)

Ethyl ester of 3-bromomethylflavone-8-carboxylic acid was reacted with dimethylamine in a conventional manner and the resultant product was reduced to give 3-dimethylaminomethylflavone-8-methanol.

m.p.: 149.5-150.5° C.; IR (Nujol): 3448, 1627 cm$^{-1}$; APCI-MS m/z: 310 [M+H]$^+$.

(Preparation 19)

1) Hydroxy group of 3-acetoxymethylflavone-8-methanol synthesized in Preparation 17 was methoxymethylated by a conventional method and then the acetyl group was removed. The resultant alcohol was oxidized to give 8-methoxymethoxymethylflavone-3-carboxylic acid.

m.p.: 142-143° C.; IR (Nujol): 1731, 1621, 1606 cm$^{-1}$; ESI-MS m/z: 339 [M–H]$^-$.

2) 8-Methoxymethoxymethylflavone-3-carboxylic acid was reacted with diphenylphosphoryl azide and then with t-butanol. The resultant product was hydrolyzed with aqueous hydrochloric acid-dioxane to give 3-aminoflavone-8-methanol.

m.p.: 191.5-192.5° C.; IR (Nujol): 3391, 3302, 1606 cm$^{-1}$; APCI-MS m/z: 268 [M+H]$^+$.

(Preparation 20)

Amino group of methyl ester of (5-amino-2-phenyl)benzo[b]furan-7-carboxylic acid was dimethylated by a conventional method and then the ester group was reduced by lithium aluminium hydride to give (5-dimethylamino-2-phenyl)benzo[b]furan-7-methanol.

m.p.: 115-116° C.; IR (Nujol): 3243, 1734, 1703 cm$^{-1}$; APCI-MS m/z: 268 [M+H]$^+$.

(Preparation 21)

1) A mixture of methyl ester of 2-acetoamino-3-nitrobenzoic acid (1.444 g, 6.06 mmol) and 6N hydrochloric acid (30 ml) was heated under reflux for 15 min. The reaction mixture was cooled with ice, adjusted to pH 8 with 10% aqueous solution of potassium carbonate and then extracted with ethyl acetate. The extract was washed with water and brine in turn and dried. The solvent was distilled off under reduced pressure. The residue was purified by column chromatography on silica gel (n-hexane/ethyl acetate=1) to give methyl ester of 2-amino-3-nitrobenzoic acid (987 mg, 83%) as yellow crystals.

m.p.: 94-96° C.; APCI-MS m/z: 197 [M+H]$^+$.

2) 10% Palladium carbon (water content 51.7%, 250 mg) was added to a solution of methyl ester of 2-amino-3-nitrobenzoic acid (980 mg, 5.00 mmol) in methanol (20 ml)-tetrahydrofuran (10 ml) and the mixture was stirred under hydrogen atmosphere at room temperature for 3 hrs. The catalyst was removed by filtration and washed with tetrahydrofuran. The filtrate and washings were combined and the solvent was distilled off under reduced pressure to give methyl ester of 2,3-diaminobenzoic acid (814 mg, 98%) as a yellowish green solid.

m.p.: 65-67° C.; IR (Nujol): 3451, 3314, 1701, 1619 cm$^{-1}$; APCI-MS m/z: 167 [M+H]$^-$ 3) A solution of methyl ester of 2,3-diaminobenzoic acid (4.00 g, 24.07 mmol) and benzaldehyde (2.56 g, 24.07 mmol) in nitrobenzene (60 ml) was stirred at 155-160° C. for 3 hrs. After being cooled to room temperature, the reaction mixture was purified by column chromatography on silica gel (n-hexane/ethyl acetate=20 and 4) to give methyl ester of 2-phenylbenzimidazole-4-carboxylic acid (3.89 g, 64%) as a pale yellow crystals.

m.p.: 125-127° C.; IR (Nujol): 3364, 1709 cm$^{-1}$; APCI-MS m/z: 253 [M+H]$^+$.

4) To 60% sodium hydride (32 mg, 0.793 mmol) washed with n-hexane was added dropwise a solution of methyl ester of 2-phenylbenzimidazole-4-carboxylic acid (200 mg, 0.793 mmol) in DMF (1.2 ml) at room temperature. The mixture was stirred at room temperature for 1.5 hrs. and 2-(trimethylsilyl)ethoxymethyl chloride (0.15 ml, 0.841 mmol) was added dropwise thereto. The mixture was stirred at room temperature for 2 hrs., cooled with ice and then water was added thereto. The mixture was extracted with ethyl acetate and the extract was washed with water and brine in turn and dried. The solvent was distilled off under reduced pressure and the residue was purified by column chromatography on silica gel (n-hexane/ethyl acetate=7 and 2.5) to give methyl ester of 1-[2-(trimethylsilyl)ethoxymethyl]-2-phenylbenzimidazole-4 or 7-carboxylic acid (113 mg, 37%) and methyl ester of 1-[2-(trimethylsilyl)ethoxymethyl]-2-phenylbenzimidazole-4 or 7-carboxylic acid (133 mg, 44%) respectively in turn of the elution as a colorless oil. Physical data of the eluted compounds are shown in turn of the elution.

IR (Neat): 2952, 1722 cm$^{-1}$; APCI-MS m/z: 383 [M+H]$^+$.
IR (Neat): 2951, 1723 cm$^{-1}$; APCI-MS m/z: 383 [M+H]$^+$.

5) Methyl ester of 1-[2-(trimethylsilyl)ethoxymethyl]-2-phenylbenzi-midazole-4 or 7-carboxylic acid (120 mg, 0.314 mmol) (compound eluted later) was reduced by using lithium aluminium hydride to give 1-[2-(trimethylsilyl) ethoxymethyl]-2-phenylbenzimidazole-4 or 7-methanol (94 mg, 85%) as colorless crystals.

m.p.: 96-100° C.; IR (Nujol): 3181 cm$^{-1}$; APCI-MS m/z: 355 [M+H]$^+$.

(Preparation 22)

8-Methoxymethoxymethylflavone-3-carboxylic acid obtained in Preparation 19-1) was subjected to amidation by a conventional method and the methoxymethyl group was removed by using aqueous hydrochloric acid-methanol. The resultant product was treated with thionyl chloride to give 8-chloromethyl-3-dimethylcarbamoylflavone.

m.p.: 202-203° C.; IR (Nujol): 1638, 1630, 1616 cm$^{-1}$; APCI-MS m/z: 324 [M+H]$^+$.

(Preparation 23)

8-Methoxymethoxymethylflavone-3-carboxylic acid obtained in Preparation 19-1) was subjected to methyl esterification by a conventional method and the methoxymethyl group was removed by using aqueous hydrochloric acid-methanol. The resultant product was treated with thionyl chloride to give 8-chloromethyl-3-methoxycarbonylflavone.

m.p.: 149.5-150.5° C.; IR (Nujol): 1732, 1637 cm$^{-1}$; APCI-MS m/z: 311 [M+H]$^+$.

(Preparation 24)

Methoxymethyl group of 8-Methoxymethoxymethylflavone-3-carboxylic acid obtained in Preparation 19-1) was removed by a conventional method and the carboxy 1 group was converted to diphenylmethyl ester. The resultant product was treated with thionyl chloride to give 8-chloromethyl-3-diphenylmethoxycarbonylflavone.

m.p.: 185.5-186° C.; IR (Nujol): 1731, 1629 cm$^{-1}$; ESI-MS m/z: 485 [M+Na]$^+$.

(Preparation 25)

8-Hydroxymethyl-3-methylflavone was treated with thionyl chloride to give 8-chloromethyl-3-methylflavone.

m.p.: 112.5-113.5° C.; IR (Nujol): 1622, 1601 cm$^{-1}$; APCI-MS m/z: 285 [M+H]$^+$.

(Preparation 26)

1) 2,6-Dibromonaphthalene (2.20 g, 7.70 mmol) was subjected to amination reaction using palladium catalyst to give 2-[bis-2-(benzyloxy)ethyl]amino-6-bromonaphthalene (2.29 g, 61%) as a yellow oil. IR (Neat): 1625, 1585 cm$^{-1}$; APCI-MS m/z: 490/492 [M+H]$^+$.

2) 2-[Bis-2-(benzyloxy)ethyl]amino-6-bromonaphthalene (205 mg, 0.42 mmol) was treated in the same manner as in Preparation 5 to give 2-[bis-2-(benzyloxy)ethyl]aminonaphthalene-6-boronic acid (124 mg, 65%) as a yellow oil.

(Preparation 27)

1) 37% Aqueous formaldehyde (13.55 ml, 180.3 mmol) was added dropwise to a solution of 2-amino-5-bromopyrydine (2.0 g, 11.56 mmol) in methanol (465 ml) at room temperature. To the mixture was added dropwise a solution of zinc chloride (3.94 g, 28.90 mmol) and sodium cyanoborohydride (3.63 g, 57.80 mmol) in methanol (155 ml) and the mixture was stirred at room temperature for 4 hrs. To the reaction mixture was added ice water (300 ml) at 5° C. and then methanol was distilled off under reduced pressure. The residue was extracted with ethyl acetate-tetrahydrofuran (1/1) and the extract was washed with water and brine in turn and dried. The solvent was distilled off under reduced pressure. The residue was purified by column chromatography on silica gel (n-hexane/ethyl acetate=24 and 5) to give 5-bromo-2-dimethylamino-pyridine (1.00 g, 43%) as colorless crystals.

m.p.: 39-41° C.; IR (Nujol): 1588 cm$^{-1}$; APCI-MS m/z: 201/203 [M+H]$^+$.

2) 5-Bromo-2-dimethylaminopyridine (402 mg, 2.00 mmol) was treated in a similar manner to that of Preparation 5 to give 2-dimethylaminopyridine-5-boronic acid (321 mg, crude 97%) as a pale brown powder.

(Preparation 28)

1) A mixture of 5-bromo-2-chloropyridine (600 mg, 3.12 mmol) and thiomorpholine (1.60 g, 15.59 mmol) was stirred at 100° C. for 16 hrs. Saturated sodium bicarbonate solution was added to the reaction mixture and the mixture was extracted with ethyl acetate. The extract was washed with water and brine in turn and dried. The solvent was distilled off under reduced pressure and the residue was purified by column chromatography on silica gel (n-hexane/ethyl acetate=50) to give 5-bromo-2-thiomorpholnopyridine (465 mg, 58%) as a colorless oil.

IR (Neat): 1581, 1481 cm$^{-1}$; APCI-MS m/z: 259/261 [M+H]$^+$.

2) Triethylamine (30 ml), bis(tributyltin) (3.05 ml, 6.04 mmol) and tetrakis(triphenylphosphine)palladium (315 mg, 0.272 mmol) were added in turn to a solution of 5-bromo-2-thiomorpholinopyridine (706 mg, 2.72 mmol) in degassed toluene (30 ml)-1,4-dioxane (30 ml) at room temperature, and the mixture was degassed and replaced with argon. The mixture was stirred at 95-100° C. for 14 hrs. After the mixture was cooled to room temperature, the solvent was distilled off under reduced pressure. The residue was purified by column chromatography on amine silica gel (Chromatolex (trademark) NH) (n-hexane/ethyl acetate=100) to give 5-tri-n-butyl-stannyl-2-thiomorpholinopyridine (467 mg, 37%) as a colorless oil.

IR (Neat): 1575, 1535, 1483 cm$^{-1}$; APCI-MS m/z: 467/469/471 [M+H]$^+$.

(Preparation 29)

1) 50% Aqueous solution of dimethylamine (30 ml) was added to 5-bromo-2-chloropyridine (1.79 g, 10 mmol) and the mixture was stirred at room temperature under argon atmosphere for 5 hrs. Saturated sodium bicarbonate solution (15 ml) was added to the reaction mixture and the mixture was extracted with ethyl acetate. The extract was washed with brine and dried. The solvent was distilled off under reduced pressure and the residue was dried at 40° C. under reduced pressure for 2 hrs. to give 5-bromo-2-dimethylaminopyrimidine (1.83 g, 90%) as colorless crystals.

m.p.: 81-82° C.; IR (Nujol): 1586, 1527 cm$^{-1}$; APCI-MS m/z: 202/204 [M+H]

2) n-Butyl lithium (1.5 Mn-hexane solution; 6.06 ml, 9.09 mmol) was added dropwise to a solution of 5-bromo-2-dimethylaminopyrimidine (1.75 g, 8.66 mmol) in tetrahydrofuran (18 ml) at −78° C. under argon atmosphere in 15 min. The mixture was stirred at the same temperature for 2 hrs. and then tri-n-butyltin chloride (2.5 ml) was added dropwise thereto. The mixture was stirred at the same temperature for 0.5 hrs. and then at room temperature for 1 hr. To the reaction mixture were added 10% aqueous potassium fluoride (50 ml) and ethyl acetate (50 ml) in turn and the mixture was stirred at room temperature for 0.5 hrs. The organic layer was separated and washed with water and brine in turn and dried. The solvent was distilled off under reduced pressure and the residue was purified by column chromatography on amine silica gel (Chromatolex (trademark) NH) (n-hexane) to give 5-tri-n-butylstannyl-2-dimethylaminopyrimidine (2.65 g, 74%) as a colorless oil.

IR (Neat): 2955, 2925, 2870, 2853, 1569, 1519 cm$^{-1}$; APCI-MS m/z: 410/412/414 [M+H]$^+$.

(Preparation 30)

Tris(dibenzylideneacetone)dipalladium (37 mg, 0.04 mmol) and triphenylphosphine (69 mg, 0.261 mmol) were added in turn to a solution of N-t-butoxycarbonyl-3,5-diiodo-L-tyrosine methyl ester (700 mg, 1.28 mmol) in degassed N-methylpyrrolidone (2.1 ml) under argon atmosphere and the mixture was stirred at 50° C. for 10 min. After the mixture was cooled to room temperature, copper (I) iodide (24 mg, 0.125 mmol) was added thereto. The reaction mixture was stirred at 50° C. for 10 min. After the mixture was cooled to room temperature, tetramethyltin (0.39 ml, 2.82 mmol) was added dropwise thereto and the mixture was stirred at 65° C. for 18 hrs. in a sealed tube. To the ice-cold reaction mixture were added water (10 ml) and saturated sodium fluoride aqueous solution in turn. The mixture was extracted with ethyl acetate. The extract was washed with water and brine in turn and dried. The solvent was distilled off under reduced pressure. The residue was purified by column chromatography on silica gel (n-hexane/ethyl acetate=5) to give N-t-butoxycarbonyl-3,5-dimethyl-L-tyrosine methyl ester (230 mg, 56%) as a brown oil.

IR (Neat): 3389, 1739, 1695 cm$^{-1}$; APCI-MS m/z: 324 [M+H]$^+$.

(Preparation 31)

N-Chlorosuccinimide (9.79 g, 73.32 mmol) was added to a solution of 4-amino-N-trifluoroacetyl-L-phenylalanine ethyl ester (9.30 g, 30.6 mmol) in dimethylformamide (305 ml) and the mixture was stirred under argon atmosphere at 55° C. for 2.5 hrs. Ethyl acetate and water were added to the reaction mixture under ice cooling and the mixture was adjusted to pH8 with saturated sodium bicarbonate solution and extracted with ethyl acetate. The extract was washed with water and brine in turn and dried. The solvent was distilled off under reduced pressure. The residue was purified by column chromatography on silica gel (n-hexane/ethyl acetate=6) to give 4-amino-3,5-dichloro-N-trifluoroacetyl-L-phenylalanine ethyl ester (8.49 g, 74%) as colorless crystals.

m.p.: 124-125° C.; IR (Nujol): 3300, 1742, 1707 cm$^{-1}$; ESI-MS m/z: 371/373 [M–H]$^-$.

(Preparation 32)

Figure 9A:
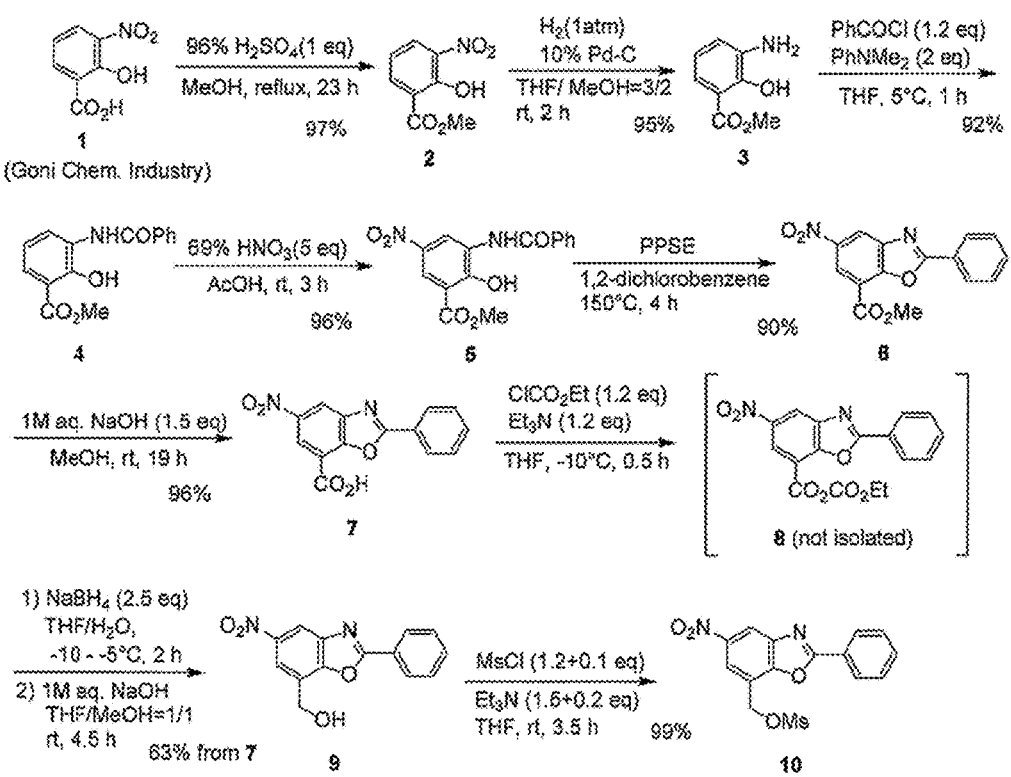
FIGS. 9A and 9B are diagrams showing reaction schemes of the compound according to the present invention.
Figure 9B:
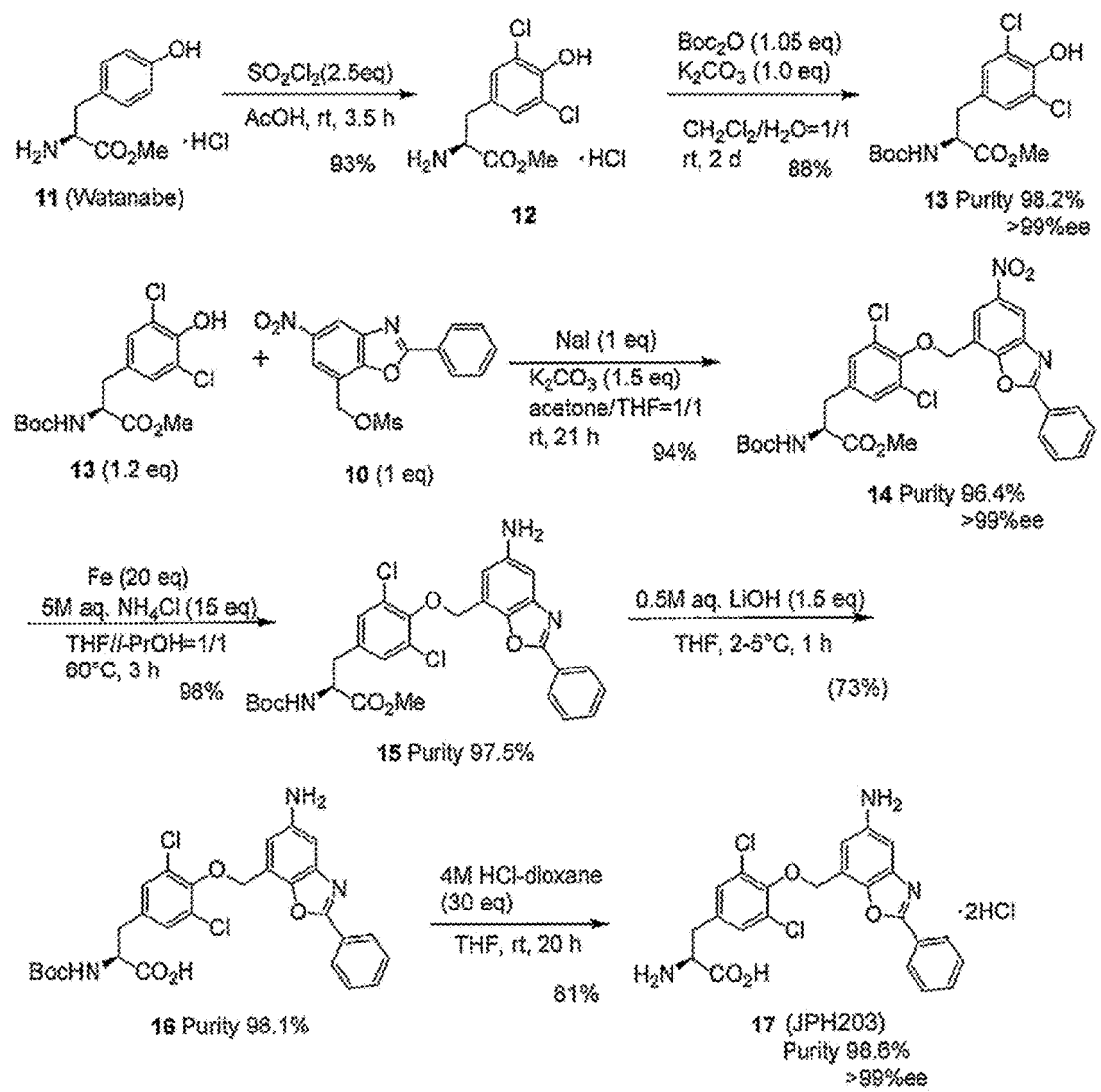

According to the reaction schemes as described in FIGS. 9A and 9B, inclusion complex of β-cyclodextrin of O-(5-amino-2-phenyl-benzoxazol-7-yl)methyl-3,5-dichloro-L-tylosine dihydrochloride of the present invention was prepared. This salt was a powder form which is pale yellow crystal or crystalline and had a melting point of 180 to 200° C. (decomposition).

1) Synthesis of a Benzoxazole Derivative

Synthesis of (2)

To a solution of 3-nitrosalicylic acid (1) (201 g, 1.09 mol) in methanol (1600 ml), 96% sulfuric acid (60.6 ml) was added in drops at room temperature, followed by refluxing for 23 hours. Thereafter, the reactant liquid was concentrated up to approximately ⅓ under reduced pressure, which was then cooled in ice bath. Through the obtained solid was filtered and washed by ice-cold methanol (600 m) and cold water (600 ml), followed by drying it under reduced pressure at 40° C., methyl 3-nitrosalicylate (2) was obtained as a yellow solid of 209.7 g (97%).

Synthesis of (3)

To a solution of methyl 3-nitrosalicyliate (2) (108.2 g, 0.549 mol) in THF (1140 ml)/MeOH (810 ml), 10% Pd—C (15.2 g) was added, followed by catalytic-reducing with hydrogen at 1 atom and room temperature for 2 hours. After filtering out the catalyst, it was washed with THF and then the solvent was distilled away. The residue was washed with diisopropylether to obtain methyl 3-aminosalicyliate (3) as a brown solid of 166.7 g (950).

Synthesis of (4)

To a solution of methyl 3-aminosalicyliate (3) (74.8 g, 0.447 mol) in THF (1130 ml), N,N-dimethylaniline (108.7 g, 0.897 mol) at 5° C. was added in drops for 40 minutes. The reactant liquid was stirred for 15 minutes, after which a solution of benzoyl chloride (75.7 g, 0.538 mol) in THF (570 ml) was added thereto in drops. After stirring at the same temperature for 1 hour, water (100 ml) was added thereto, after which THF was distilled away. Water (900 ml) was added to the residue, followed by extracting by ethyl acetate, washing the organic phase by 10% hydrochloric acid, water and saturated saline, drying by sodium sulfate, after which the solvent was distilled away. Through the obtained rough crystallization was combined with the crystal obtained according to the same procedure with the amino compound (3) (90.16 g) and it was recrystallized with ethyl acetate, methyl 3-benzoylaminosalicylate (3) was obtained as a colorless solid of 247.1 g (92%).

Synthesis of (5)

To a solution of methyl 3-benzoylaminosalicylate (4) (83.2 g, 0.296 mol) in acetic acid (1480 ml), 69% nitric acid (d=1.42) (95 ml, 1.458 mol) was added in drops at inner temperature 15° C. The reactant liquid was stirred at room temperature for 3 hours, which was then poured in ice water (300 ml) to be stirred for 10 minutes. Through the obtained solid was filtered, washed with water (3 times) and ether and dried in air, methyl 3-benzoylamino-5-nitrosalicylate (5) was obtained as a yellow solid of 93.4 g (96%).

Synthesis of (6)

A mixture of methyl 3-benzoylamino-5-nitrosalicylate (5) (72.2 g, 0.260 mol) and a solution of PPSE in 1,2-dichloro benzene (780 ml) was stirred at 150° C. for 4 hours. Through the reactant liquid was ice-cooled, the precipitated crystal was filtered, followed by washing with n-hexane and ice-cold methanol and drying under reduced pressure, methyl 5-nitro-2-phenylbenzoxazole-7-carboxylate ester was obtained as a pale yellow solid of 61.2 g (90%).

Synthesis of (7)

To suspension of methyl 5-nitro-2-phenylbenzoxazole-7-carboxylate ester (6) (59.2 g, 0.198 mol) in methanol (990 ml), 1M sodium hydroxide aqueous solution (297 ml, 0.297 mol) was added in drops, followed by stirring at room temperature for 19 hours. The reactant liquid was acidified with 10% hydrochloric acid under ice-cooling and stirred for a few minutes. Through the obtained solid was filtered, washed with water and methanol and dried under reduced pressure, 5-nitro-2-phenylbenzoxazole-7-carboxylic acid (7) was obtained as a colorless solid of 54.2 g (96%).

Synthesis of (9)

To a suspension of 5-nitro-2-phenylbenzoxazole-7-carboxylic acid (7) (26.4 g, 0.0931 mol) in THF (470 ml), triethylamine (15.57 ml, 0.112 mol) was added, followed by stirring at room temperature for 30 minutes. The reactant liquid was cooled to −10° C. and ethyl chlorocarbonate (10.68 ml, 0.112 mol) was added thereto, followed by stirring at the same temperature for 30 minutes. After sodium borohydride (8.84 g, 233.7 mmol) was added thereto and stirring was made for 30 minutes, THF/water (317 ml/64 ml) was added thereto in drops over 3 hours at −10° C. to −6° C. The reactant liquid was stirred further for 2 hours, followed by pouring ice water, filtering the precipitated solid and washing with water. The solid obtained in accordance with the same procedure as that of 5-nitro-2-phenylbenzoxazole-7-carboxylic acid (7) (14.6 g) was combined, followed by suspending THF (600 ml)/methanol (600 ml), adding thereto 1M a sodium hydroxide aqueous solution (115 ml) stirring at room temperature for 4.5 hours. Through the reactant liquid was immersed in ice water and the precipitated solid was filtered and then dried in air, 7-hydroxymethyl-5-nitro-2-phenylbenzoxazole (9) was obtained as an approximately colorless solid of 24.4 g (63%).

Synthesis of (10)

To a suspension of 7-hydroxymethyl-5-nitro-2-phenylbenzoxazole (9) (46.2 g, 0.171 mol) in THF (1150 ml), triethylamine was added (34.9 ml, 0.250 mol) under ice-cooling. Methylsulfonyl chloride (23.1 g, 0.200 mol) was added thereto in drops, followed by stirring at 30 minutes under ice-cooling and then 3 hours at room temperature. Triethylamine (4.55 ml, 0.033 mol) and Methylsulfonyl chloride (1.29 ml, 0.017 mol) were added thereto and stirred further for 30 minutes. The reactant liquid was poured in ice water to filtrate the precipitated solid. Through the obtained solid was washed with water and diisopropylether and dried at 40° C. under reduced pressure, 5-nitro-2-phenylbenzoxazole-7-ylmethylmetanesulfonate (10) was obtained as a pale yellow solid of 59.1 g (99%).

2) Synthesis of Dichlorotyrosine

Synthesis of (12)

To a suspension of (S)-tyrosine methyl ester hydrochloride (11) (60.15 g, 0.26 mol) in acetic acid (294 ml), sulfuryl chloride (52.22 ml, 0.65 mol) was added in drops, which was then stirred for 3.5 hours. Through the reactant liquid was concentrated and the residue was fully washed with ether and then dried, (S)-dichlorotyrosine methyl ester hydrochloride (12) was obtained as a colorless solid of 72.70 g (93%).

Synthesis of (13)

To a suspension of (S)-dichlorotyrosine methyl ester hydrochloride (12) (72.42 g, 0.24 mol) in water (1.41), 2M potassium carbonate aqueous solution (120.5 ml) was added in drops under ice-cooling. A solution of Di-t-butyl-dicarbonate (58.1 ml, 0.25 mol) in dichloromethane (1.41) was added thereto, followed by stirring 1.5 hours under ice-cooling and 40 hours at room temperature. The reactant liquid was filtrated using celite, followed by extracting the filtrate with chloroform. The organic phase was washed with water and saturated saline and dried with sodium sulfate, and then the solvent was distilled away. By washing the residue with n-hexane, (S)—N-Boc-dichlorotyrosine methyl ester (13) was obtained as a colorless solid of 76.95 g (88%).

3) Synthesis of the Salt of the Compound according to the Present Invention

Synthesis of (14)

5-nitro-2-phenylbenzoxazole-7-ylmethylmetanesulfonate (10) (29.11 g, 83.6 mmol) was dissolved in THF (820 ml), to which acetone (820 ml) was added. (S)—N-Boc-dichlorotyrosine methyl ester (13) (36.54 g, 100 mmol), sodium iodide (12.53 g, 83.6 mmol) and potassium carbonate (17.37 g, 125 mmol) was added thereto and stirred at room temperature for 21 hours. The reactant liquid was filtered and then the filtrate was concentrated up to approximately ½. Ethyl acetate and water were added thereto and separated into liquids, followed by washing the organic phase with water, 5% sodium thiosulfate aqueous solution and saturated saline, distilling away the solvent using sodium sulfate. After the product obtained by the same procedure as those of 5-nitro-2-phenylbenzoxazole-7-ylmethylmetanesulfonate (10) (30.06 g) and (S)—N-Boc-dichlorotyrosine methyl ester (13) (37.66 g) were added thereto, a total crude product of 116.2 g was washed with diisopropylether and dried, due to which, the nitro compound was obtained as a pale yellow solid of 98.43 g (94%).

Synthesis of (15)

The nitro compound (14) (57.04 g, 92.5 mmol) was dissolved in THF (1340 ml), to which isopropanol (1340 ml) was added and thereafter heated at 60° C. as internal temperature. 5M ammonium chloride aqueous solution (278 ml, 1.39 mol) and subsequent iron powder (103.32 g, 1.85 mol) are added thereto, followed by stirring at 60° C. for 3 hours. After the reactant liquid was filtered using Celite, the filtrate was concentrated up to approximately ⅓. After the undesired substance on Celite were washed with hot ethyl acetate 3 times, the filtrate was combined, followed by washing with water and saturated saline and drying with sodium sulfate. Through the solvent was distilled away and the obtained solid was washed with diisopropylether and dried, the amino compound (15) was obtained as a yellow solid of 53.03 g (98%).

Synthesis of (16)

The Amino compound (15) (86.91 g, 0.148 mol) was dissolved in THF (1430 ml), to which 0.5M lithium hydroxide aqueous solution (444 ml, 0.222 mol) was added in drops while cooling in ice bath to be approximately 10° C. as internal temperature, followed by stirring further 1 hour in ice bath. The reactant liquid was concentrated up to approximately ½ and water (600 ml) was added thereto, followed by setting pH to around 4 by 10% citric acid aqueous solution and extracting with ethyl acetate-THF 10:1). The extract liquid was washed with water and saturated saline, followed by drying with sodium sulfate and distilling away the solvent. Through the obtained residue was recrystallized with ethyl acetate-THF (10:1), nearly colorless solid (72.94 g, crude yield 86%) was obtained. Through the solid (10.03 g) was recrystallized with chloroform-methanol (10:1), the carboxylic acid (16) was obtained as nearly colorless solid of 8.63 g (yield 86%).

Synthesis of the Salt of the Compound According to the Present Invention (17)

To a solution of the carboxylic acid (16) (85.23 g, 0.149 mol) in THF (750 ml) under ice cooling, 4M hydrogen chloride-dioxane (1117 ml, 4.47 mol) was added in drops at 5 to 10° C. for 2 hours. The reactant liquid was stirred at the same temperature for 1 hour and stirred at room temperature for 20 hours while gradually elevating temperature. Diisopropylether was added thereto and the solid was filtered away, followed by washing with diisopropylether. The obtained solid was divided into 3 lots, followed by dissolving in ethanol (total 2300 ml) to filtrate away the insoluble matter. The filtrate was concentrated at room temperature under reduced pressure up to approximately 1000 ml, followed by stirring the obtained solution at room temperature. Through the obtained crystal was filtered and dried, the salt of the compound according the present invention (17) was obtained as pale yellow solid of 66.11 g (81%).

4) Synthesis of Cyclodextrin Inclusion Complex (1) 1,000 g of sulfobutyl ether-β-cyclodextrin (abbreviated as SBE-CD, trade name: Captisol) was weighed, and taken up in a 5-L container in a sterile hood for cell culture, and to which 1,800 ml of HPLC-grade pure water was added, and the resultant mixture was stirred overnight to obtain a clear solution (resulted in approximately 36% by weight).

(2) Next morning, the clear solution was heated to 32-36° C. in a water tank, 45.5 g of a HCl salt of a compound according to the present invention; 100 ml of ethanol for 35.5 g as a free base, 200 ml of pure water, and 300 ml of the SBE-CD solution were added while maintaining the temperature, as a result, a compound solution was obtained. The pH of the solution was confirmed to be 3-4.

(3) 3.4 g of caustic soda was dissolved in 200 ml of pure water, the resultant caustic soda aqueous solution was added to the above solution to adjust the pH to 6.5 while stirring the solution.
(4) In this warm state, the solution was sterile-filtered through a 0.4 μm filter using a vacuum pump. The filtrate was taken up in a 5-L sterilized container, diluted with the SBE-CD solution prepared in (1), and adjusted to 2800 ml of the final volume.
(5) Further, after the stirring of 5 minutes, the pH was measured, and confirmed to be 6.5. The resultant mixture was aliquoted into 30-ml vial bottles each by 15 ml using a sterilized dispenser. The final compound concentration was 10 mg/ml. Each vial bottle was treated over one week in a freeze dryer (Lyostar3, FTS Systems SP Scientific).
(6) The vial bottle after the freeze drying was sealed with a rubber stopper, fastened with a metal, and stored in a refrigerator.
(7) For the resolubilization, 14.1 ml of distilled water for injection was added, and the resultant mixture became a 15 ml of pale yellow solution using a voltex mixer for 5-10 minutes.

Test Examples

The test was performed by the following materials and methods.
(Pten-Deficient Mice (tPTEN−/−))
Animal experiments were conducted in accordance with the Declaration of Helsinki and protocols were approved by an institutional ethical committee (2011-73) and by CIEPAL (NCE/2011-33). Mice were maintained under specific pathogen-free conditions at the C3M's animal room facility. Pten-deficient mice (tPTEN−/−) were generated by crossing mice carrying two Pten floxed alleles with proximal lck promoter-cre transgenic mice (Reference 53). Animals were characterized via PCR as previously described (Reference 53).
(Transcriptomic Analysis)
When clinical signs of lymphomagenesis were observed (e.g. fur ruffling, hunched posture, facial oedema, and/or shallow breathing) mice were sacrificed with a lethal pentobarbital injection. Tumors were dissected, homogenized in PBS on 70 μm cell strainers (BD Biosciences) and the total RNA isolated and transcribed to cDNAs as previously described (Reference 54); four independent tumors were analyzed and thymocytes from two wild-type mice were also processed. cDNAs were hybridized to Affymetrix DNA chips (Affymetrix-MoGene-1_0-st-v1) and gene expression data were normalized (GSE 39591) and submitted to a supervised SAM (Significance Analysis of Microarrays) analysis using a 25% false discovery rate. The Linear Models for Microarray Analysis (LIMMA) was then used to identify differentially expressed probes with a p value<$10^4$. This leads to gene selection having an abs (log Fold Change) >0.5. After removing replicates with smaller p values between phenotypes and non-annotated sequences, the combined analysis identified 498 up-regulated genes and 279 down-regulated genes in the tumors.
(Cell Cultures)
In addition to the murine cell lines denoted as KO99L, KO1081L, and KO631L which were established from independent tPTEN−/− tumors, the human Ke37, DND41, Sil-ALL, Peer, Molt-16, Jurkat (T-ALL) and SupT1 (T-LL) were proliferated in RPMI 1640 medium (Invitrogen) supplemented with 10 or 20% (Sil-ALL and murine cell lines) Fetal Calf-Serum and 50 units/ml penicillin, 50 mg/ml streptomycin and 1.0 mM sodium pyruvate (Sigma-Aldrich). Cell cultures were maintained at 37° C. under 5% $CO_2$.
(Reagents) Chemical Compounds Used in this Study:
2-Aminobicyclo-(2,2,1)-heptane-2-carboxylic acid (BCH), dexamethasone, doxorubicin hydrochloride, essential amino acid (EAA; 50× solution), non-essential amino acid (NEAA; 100× solution), D-leucine and wortmannin (Sigma-Aldrich); KU0063794 (rel-5-[2-[(2R,6S)-2,6-dimethyl-4-morpholinyl]-4-(4-morpholinyl)pyrido[2,3-d]pyrimidin-7-yl]-2-methoxybenzenemethanol), PI-103 hydrochloride (3-[4-(4-Morpholinylpyrido[3',2':4,5]furo[3,2-d] pyrimidin-2-yl]phenol hydrochloride), and rapamycin (Tocris Bioscience); L-Asparaginase, Erwinase® (Crisantaspase) (EUSA-PHARMA). Salubrinal (N-(2,2,2-trichloro-1-(3-(quinolin-8-yl)thioureido)ethyl)cinnamamide) (Enzo Life Science); Q-VD-OHP (MPBiomedicals).
(Patients)
Informed consent was obtained according to institutional guidelines. Heparin-treated blood was obtained from three T-ALL patients and from two healthy donors. Patient lymphoblasts were isolated within 24 hours post collection using Ficoll-Paque PLUS density gradient following vendor recommended procedures (GE Healthcare Life Sciences).
(Cell Viability, Proliferation and Cytotoxicity Assays)
Two different assays were employed: i) In a 96-well plate format, cells ($4.0\pm0.1\times10^4$ per well; 100 μL) were incubated with effectors (48 h, 37° C.; n=4 per experiment) and then WST-1 reagent (10 μL; Roche Diagnostics) added to each well of 96-well plates, incubated, and the formazan production was measured at 490 nm; and ii) cells ($2.0\pm0.1\times10^4$ per well; 100 μL) were incubated with effectors (48 h, 37° C.; n=4 per experiment) and then bromodeoxyuridine reagent (10 μL/well; Roche Diagnostics) was added to each well and incubated (8 h, 37° C.). The cells were then fixed, denatured and incubated with anti-BrdU-conjugated with peroxidase (POD) antibody (100 μL/well). Colorimetric substrate (TMB: tetramethyl-benzidine; 100 μL/well) was added and BrdU incorporation quantified via optical density measurement (450 nm) which corresponds to DNA synthesis and proliferating cells.
(Western-Blotting Analysis)
Cell extracts were prepared using a cell lysis buffer (50 mM HEPES, pH 7.4, 150 mM NaCl, 20 mM EDTA, 100 mM NaF, 10 mM $Na_3VO_4$, 0.5% nonyl phenoxypolyethoxylethanol (NP40) supplemented with a cocktail of protease inhibitors. After SDS-PAGE separation and transfer to nitrocellulose immunoblotting was performed using the following antibodies against: Akt (Cell Signaling Technologies, #9272), CHOP (#2895), cleaved caspase 3 (#9664), c-Myc (#9402), eIF2a (#9721), 4EBP1 (#9644), LC3A/B (#12741), PARP (#9542), pJnk (T183/Y185) (#9251), pSer235-236-S6RP (#4856), pSer473-Akt (#9271), pSer65-4EBP1 (#9451) and S6RP (#2217); Bax (Sigma-Aldrich, B8429); PUMA (Abcam, ab54288); Bak (Millipore, 06536); ATF4 (Santa Cruz Biotechnologies, sc200), GADD34 (sc8327), Hsp60 (sc-1722), Hsp90 (sc-13119) and XBP1 (sc-7160); ATF6 (Imgenex, IMG-273).
(Annexin V/PI Staining Assay)
Apoptosis assessment was performed by measuring phosphatidyl-serine membrane redistribution via annexin-V-FITC (Invitrogen). Cells ($5.0\pm0.1\times10^5$ per well; 2.0 mL) were incubated with effectors, and re-suspended in staining solution (110 μL; Annexin-V (1/10) and incubated in the dark (15 min, RT). Cells were washed with PBS and re-suspended in propidium iodide staining solution (1.0 μg/ml; 2.0 mL) and immediately analyzed by flow cytometry on a MacsQuant Analyser (Miltenyi Biotech). Basal apoptosis and necrosis were determined on control untreated cells.
(Analysis of CD98 Surface Expression)

Cells were collected and wash with PBS. After spinning, cells ($10^6$; 1.0 mL in PBS, EDTA 5.0 mM, 0.1% BSA) were incubated with a rat anti-CD98 antibody (H202-141, 5.0 µg/mL, BDPharmingen), for 30 min, at 4° C., in the dark. Cells were washed and incubated with a goat anti-rat-AlexaFluor®-488 secondary antibody (A11006, 2 µg/ml, Life Technologies) for 30 min at 4° C. Cells were spinned down, washed twice and fixed with 1% PFA, until analysis on a MacsQuant Analyser (Miltenyi Biotech).
(Mitochondrial Trans-Membrane Potential Determination)

Mitochondrial trans-membrane potential ($\psi$m) changes as a function of apoptotic events were measured using Tetra Methyl Rhodamine Ethyl Ester Perchlorate assay (TMRE; Molecular Probes). Murine or human cells ($5.0\pm0.1\times10^5$ per well; 2.0 mL) were exposed to varying concentrations of COMPOUND-JP for up to 24 h and were then incubated with TMRE (1.0 µM; 30 min, 37° C.). Thereafter, the cells were washed twice with PBS and then stained with DAPI (Sigma-Aldrich, 1.0 µg/mL) and examined via a MACSQuant Analyser (Miltenyi Biotech) and the data evaluated via FlowJo software.
(Active Caspase 3 Staining)

Cells ($1.0\pm0.1\times10^6$ per well; 1.0 mL) were stimulated with different COMPOUND-JP doses with or without caspase3 inhibitor Qvd-OH (20 µM). Cells were then stained with caspase 3 inhibitor conjugated (RED-DEVD-FMK; Biovision) and incubated (1.0 h, 37° C. at 5% $CO_2$). Cells were washed with Wash Buffer, then centrifuged (3000 rpm, 5.0 min) and stained with annexin V-FITC (10 µL/mL; Miltenyi Biotech) for 30 min and DAPI (1.0 µg/mL) added prior to examination via a MacsQuant Analyser.
(Intracellular Flow Cytometry Analysis (Phosphoflow))

Cells ($1.0\pm0.1\times10^6$ per well; 1 mL) were incubated with various effectors (24 h, 37° C.) and then permeabilized with Cytofix/Cytoperm buffer (100 µL, 30 min, 4° C.) and then washed with PermWash (BD Biosciences) and stained with phospho-Ser235/236-S6RP antibody (30 min, 4° C.). After an additional PermWash, cells were then stained with a secondary anti-rabbit-alexaF 488 (20 µg/mL; Life Technologies) for (30 min, 4° C.). Cells were then washed in PermWash and re-suspended in staining buffer (PBS+0.1% bovine serum albumin+1.0% paraformaldehyde) and analyzed by flow cytometry on a MacsQuant Analyser (Miltenyi Biotech).
(Monitoring In Vivo Tumor Growth)

All mice in each experimental group were subcutaneous injected with 99KOL-LUC T-lymphoma cells (200 µL; $5.0\pm0.1\times10^6$) stably expressing a reporter luciferase gene. After two days post injection, mice were intraperitoneally administered COMPOUND-JP (50 mg/kg/day/5 days a week) which had been prepared by dissolving drug powder and mixing into saline (NaCl 0.9%). Body weights and tumor volumes were measured every five days. Tumor volumes were calculated according to the mathematical formula: $V=(L*W^2)/2$ (L:Length; W:Width). To conduct the bioluminescence imaging, mice received an intraperitoneal injection (150 µL, 30 mg/mL) of D-luciferin (Caliper Life Science) and were anesthetized via inhaled isoflurane (2.0%). Bioluminescence signals were monitored using the Photon imager (Biospace Lab) equipped with a highly sensitive cooled CCD camera; all images were collected 10 min post D-luciferin injection. Data were analyzed using total photon flux emission (photons/second) focused on the regions of interest (ROI) enveloping the tumor region.

(Immunohistochemistry)

Sections (4 µm) in paraffin blocks of dissected tumors were labeled with a primary rabbit phospho-S6RP antibody (#4858, Cell Signaling Technology). A second, anti-rabbit antibody conjugated with peroxidase (HRP) (SignalStain®, #8114, Cell Signaling Technology) was added to the sections before revelation with diaminobenzidine (DAB) as recommended by the manufacturer. For necrosis evaluation, sections were stained with hematoxylin/eosin/safran (HES). The images were analyzed and necrosis areas quantified using the ImageJ software (NIH).
(Statistical Analyses)

Statistical analyses for in vitro experiments were performed using either two-tailed Student's t test or calculated using ANOVA followed by a Dunnett's multiple comparison test at the 95% confidence level. Combinations were analyzed by ANOVA followed by Tukey's Multiple comparison test to determine significance between experimental groups. The synergism between drugs was analyzed using the Chou-Talalay method. For in-vivo experiments, statistical analyses were performed using the two-tailed Mann-Whitney rank sum test. P-value <0.05 was accepted as statistically significant (*:$p<0.05$; :$p<0.01$; *:$p<0.001$). Analyses were performed using the GraphPAd Prism 3.0 software.
(Quantification of a Neutral Amino Acid Transporter, LAT1 Gene, and LAT2 Gene Expressed in an Established Culture Cell Derived from Various Cancers of a Human Being)

RNA is extracted from each cell, and each mRNA was measured by a quantitative PCR method using a primer specific to LAT1 and LAT2. (Inhibitory effect of a LAT1 selective inhibitor, COM-JP on the proliferation of a 44As3-11 cell derived from human scirrhous stomach cancer and a Panc-1 cell derived from human pancreatic cancer)

The culture in the absence of COM-JP and in the presence of COM-JP with different concentrations in the culture medium of each cancer cell was continued for 5 days. Proliferation activity of the cell on each elapsed day was measured by a MTT method.
(Procedure of an Experiment in which an Effect is Shown when Each of a LAT1 Selective Inhibitor, COM-JP, and Existing Agents, Gemcitabine (GEM) and Paclitaxel (Pac) was Used alone or in Combination)

Two kind of cancer cells of a 44As3-11 cell derived from human scirrhous stomach cancer and a Panc-1 cell derived from human pancreatic cancer were cultured in the presence or absence of COM-JP, to which GEM and Pac was added on day 2, and the resultant mixture was continued to be cultured for 2 hours. Subsequently, the medium was replaced with a new medium, and the culture was performed in the presence or absence of COM-JP for 2 days more. Finally, the cells were collected, and the quantity of survival activity of the cells was determined by a MTT method. In each experiment, three cases of the group under the same conditions were measured, and the average value and the standard error, and the p-value of significance test were shown in the diagram.
(Effect on the Tumor Growth in a Nude Mouse Model Inoculated with a HT-29 Cell Derived from Human Large Intestine Cancer when COM-JP and 5-FU were Used in Combination)

A HT-29 cell was inoculated subcutaneously into a mouse, and the transition of the size of the tumor lump was measured with time from the day on which the tumor has grown to a certain size, when each of COM-JP and 5-FU was used alone or in combination.
(Synergistic Effect on the Tumor Growth in a Nude Mouse Model (SOI Model) Inoculated in the same Site with a HT-29 Cell Derived from Human Large Intestine Cancer when COM-JP and CDDP were Used in Combination)

Figure 16:
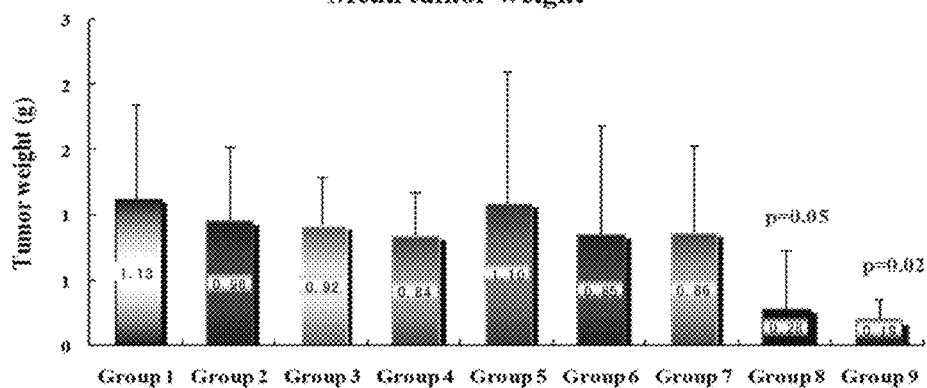
FIG. 16 is a diagram showing a synergistic effect on the tumor growth in a nude mouse model (SOI model) inoculated in the same site with a HT-29 cell derived from human large intestine cancer when COM-JP and CDDP were used in combination.

Cypridina luciferin was expressed in a HT-29 cell derived from human large intestine cancer, and which was grafted onto the wall of large intestine of a mouse to produce a metamouse. According to this, the quantity of the size of the tumor could be determined with time with emission intensity. In FIG. 16, the size of tumor in each treatment group was shown with a bar graph. Group 1 is a control group, Groups 2 to 4 are a group in which COM-JP was intraperitoneally administered alone at 3.1, 12.5, and 50 mg/kg weight/day every day for 4 weeks, Group 5 is a group in which CDDP was intraperitoneally administered alone at 2.5 mg/kg/day three times on day 0, day 6, and day 13, Groups 6 to 8 are a group in which Groups 2 to 4 and Group 5 were combined to be administered in combination, and Group 9 is a group in which COM-JP was orally administered at 300 mg/kg/day every day for 4 weeks.

<Results>

The results of the above test are shown below.
(tPTEN−/− Tumors, Human T-ALL/T-LL Cells Lines, and Primary Cells have Enhanced LAT1/CD98hc (slc7a5/slc3a2) Expression.)

Figure 1B:
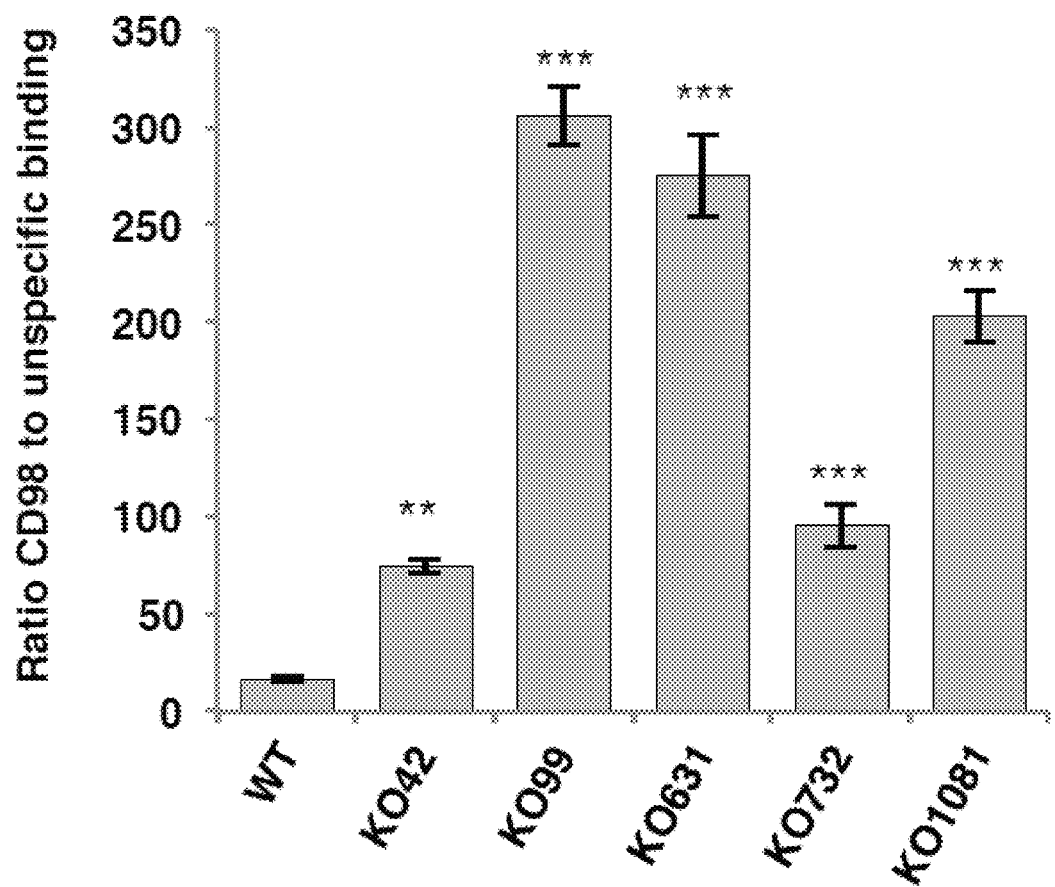
FIG. 1B-E shows the flow cytometry analysis of surface CD98 levels after anti-mouse CD98 rat mAb staining followed by revelation with a secondary anti-rat FITC antibody, ratio of specific MFI/non-specific MFI.
Figure 1C:
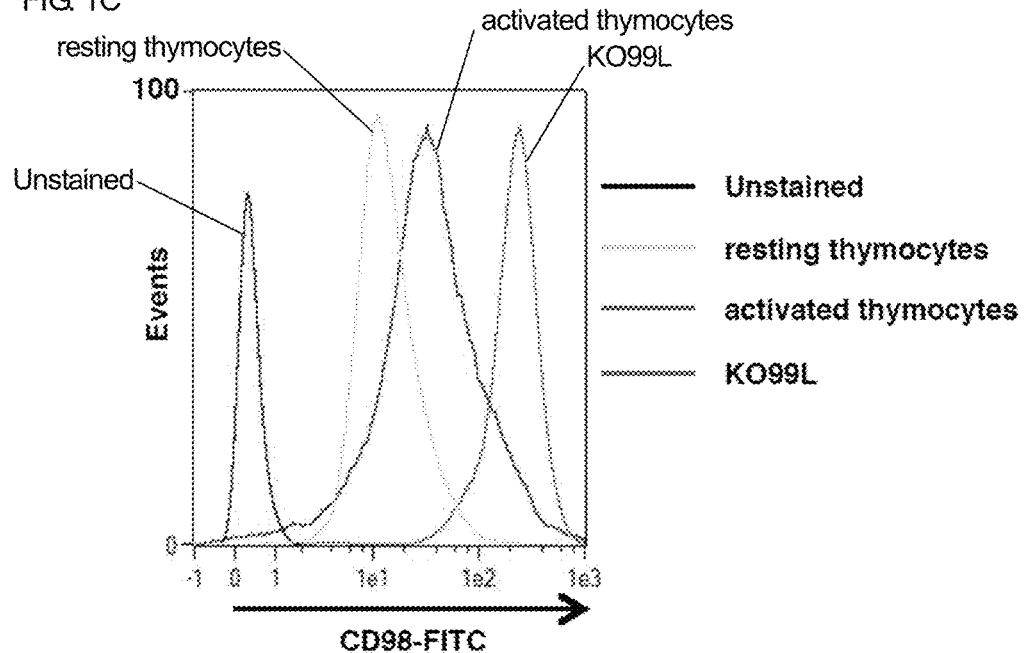

Mice (tPTEN−/−) develop aggressive and invasive lymphomas. Global gene expressions of normal thymocytes and tPTEN−/− thymic tumor cells were established using pan-genomic Affymetrix mouse DNA chips. After data normalization, gene expression profiles (GEP) from wild-type thymocytes (n=3) and tPTEN−/− tumor cells (n=4) were evaluated. Compared to wild-type, tPTEN−/− tumor cells displayed four hundred and ninety eight up-regulated genes. As depicted in FIG. 1A, the present inventors observed that the SLC7A gene encoding LAT1 was up-regulated (log 2: 2.44 fold) in tPTEN−/−; compared to normal cells. By contrast, the expression of SLC3A2 that codes for CD98hc was only slightly enhanced in the tumors (0.874 fold). In addition, to serve as references, the present inventors also present the results of the c-myc gene which was also highly expressed in tPTEN−/− cells (2.22 fold), while marks—a house-keeping gene—was not significantly different between the two categories. Quantitative PCR analysis was able to confirm the observed enhanced expression of LAT1 and c-myc, but not SLC3A2 in malignant cells (data not shown). High LAT1 expression was observed in two primary tPTEN−/− tumors (KO mice #99, #631) and used to establish cell lines denoted as KO99L and KO631L, respectively. As previously discussed in the introduction, LAT1 requires CD98hc linked via a disulfide bond in order to be transport active; therefore, the present inventors also analyzed its surface expression by performing flow cytometry analysis using an anti-CD98hc antibody. Compared to normal (WT) thymocytes (FIG. 1B), five tPTEN−/− tumors displayed higher CD98 expression; cell activation: (PMA+ionomycin) resulted in a 2.8 fold increased expression compared to 17 fold in tumor thymocytes (FIG. 1D).

Figure 1D:
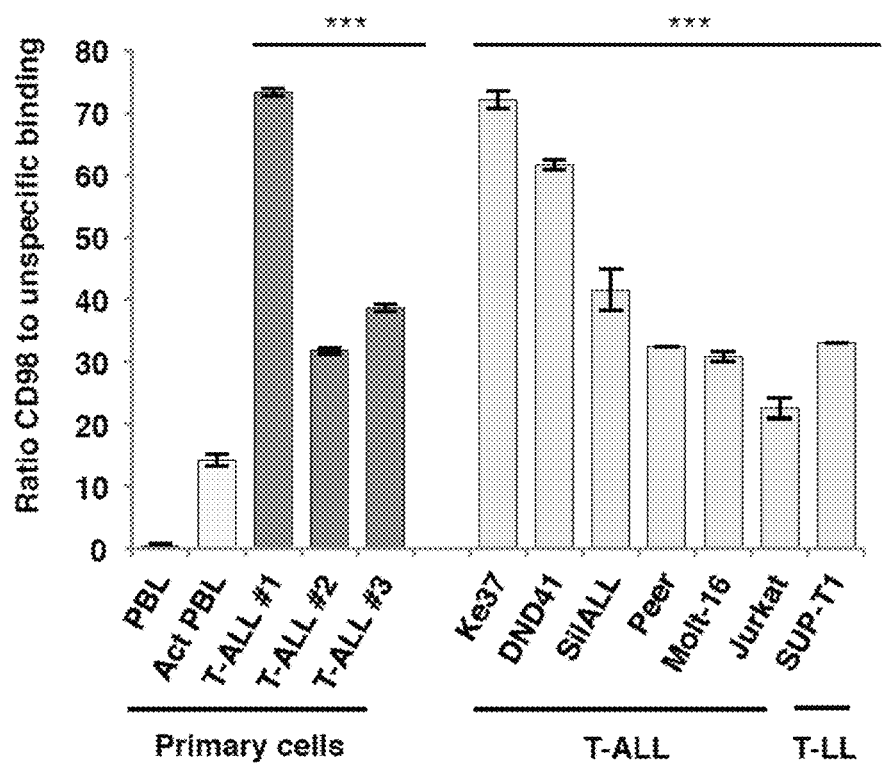
Figure 1E:
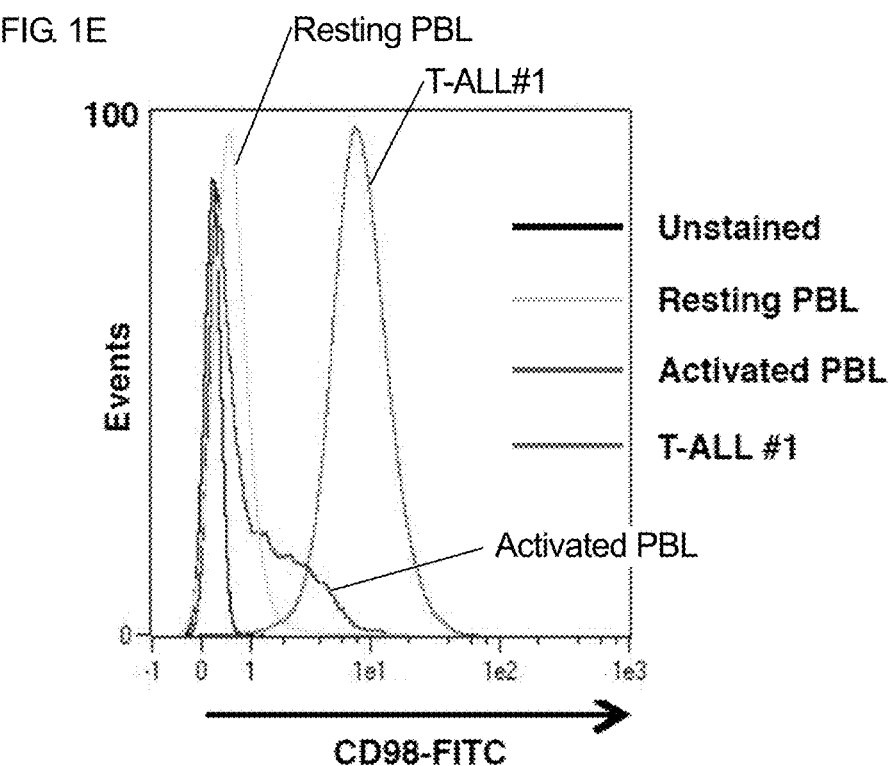

Similarly, three primary human T-ALL samples displayed higher CD98 levels compared to resting and activated peripheral blood lymphocytes (PBL) from healthy donors (FIG. 1D-E). Altogether, these results show that CD98 expression is enhanced in activated murine and human T cells and attained even higher levels in transformed lymphocytes.

(Pharmacological CD98/LAT1 Targeting Decreases In Vitro tPTEN−/− Cell Survival)

Figure 2A:
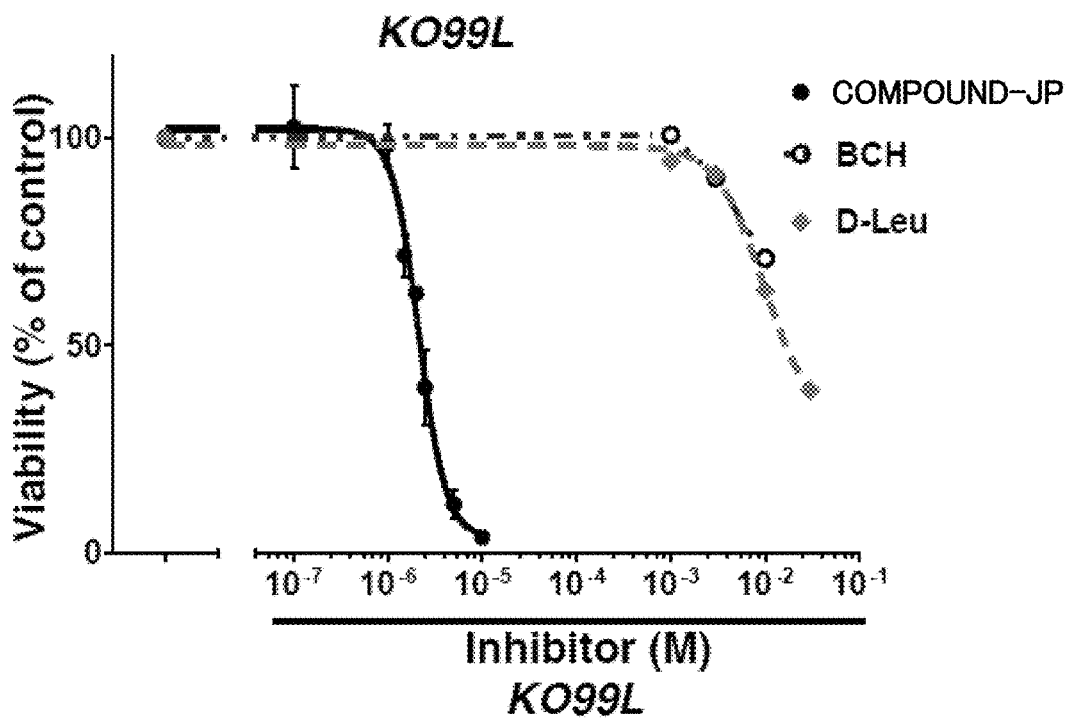
FIG. 2A shows the analysis of metabolic activity using a WST-1 cell viability assay in the presence of disruptors of amino acid uptake. Cells were incubated with COMPOUND-JP, BCH or D-Leucine for 48 h. COMPOUND-JP: mean of seven independent experiments in triplicates+/−SEM; p-value calculated using two-tailed Student's t test; BCH, D-Leu: one experiment in triplicates.
Figure 2B:
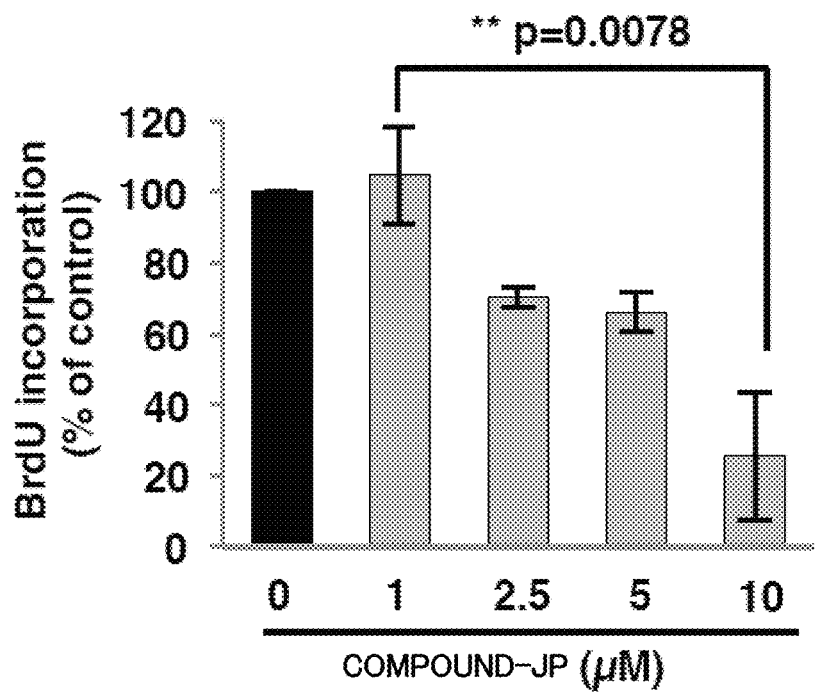
FIG. 2B shows the result that the proliferation was assessed by a BrdU incorporation Elisa. Data are shown as mean of two independent experiments performed in quadruplicates (mean+/−SEM; Student's t test).
Figure 9C:
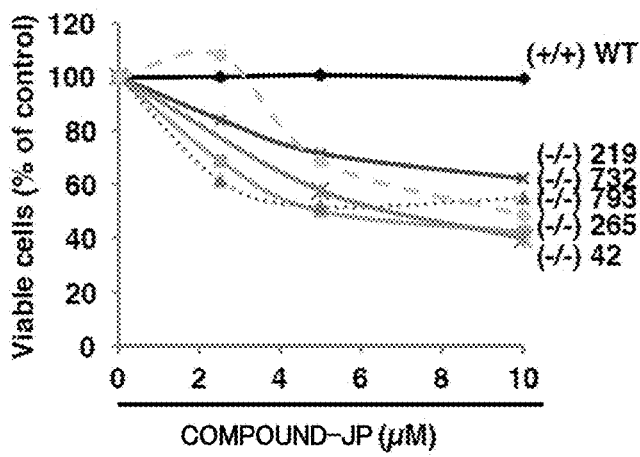
FIG. 9C shows that COMPOUND-JP interferes with the survival of primary tPTEN−/− cells, but not normal thymocytes. Fresh primary cells from tPTEN KO tumors (−/−) or normal thymocytes (+/+) were incubated with indicated doses of COMPOUND-JP before WST-1 analysis of cell viability.

The present inventors used the established tPTEN−/− tumor cell line denoted as KO99L to probe cell viability in the presence of varying concentrations of BCH, D-Leucine and COMPOUND-JP. BCH is a classic System L inhibitor but lacks LAT1 selectivity (Non-Patent Literature 18). As depicted in FIG. 2A, BCH and D-Leucine maintained high cell viability at high dose concentrations; cell viability was 30% and 60% at 10.0 and 30.0 mM, respectively; FIG. 2A). In contrast, the LAT1 selective inhibitor COMPOUND-JP influenced KO99L cell viability to a much greater extent displaying a lower drug concentration to kill half of the cells with an $IC_{50}$=2.4 µM (FIG. 2A). At 10.0 µM, COMPOUND-JP diminished cell cycling (proliferation) by 75% after 48 h (FIG. 2B). In a concentration dependent manner, COMPOUND-JP influenced cell viability in freshly isolated tPTEN−/− tumor cells but was non-toxic in normal murine thymocytes (Supplementary Materials FIG. 9C).

(COMPOUND-JP Inhibits Essential Amino Acid Influx)

Figure 2C:
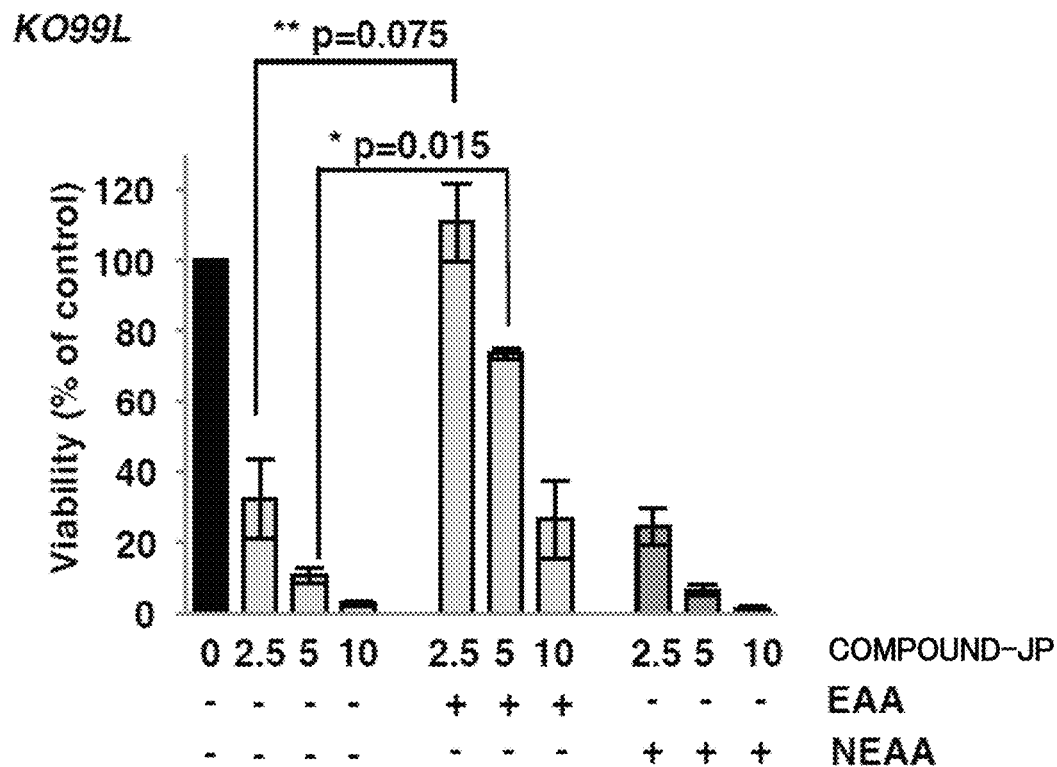
FIG. 2C shows the result that the cells were treated or nor with COMPOUND-JP and the medium was supplemented with Non Essential (N) or Essential (E) Amino Acids when indicated. Cell viability was measured after 48 h (mean of three independent experiments in triplicates+/−SEM; Student's t test).
Figure 2D:
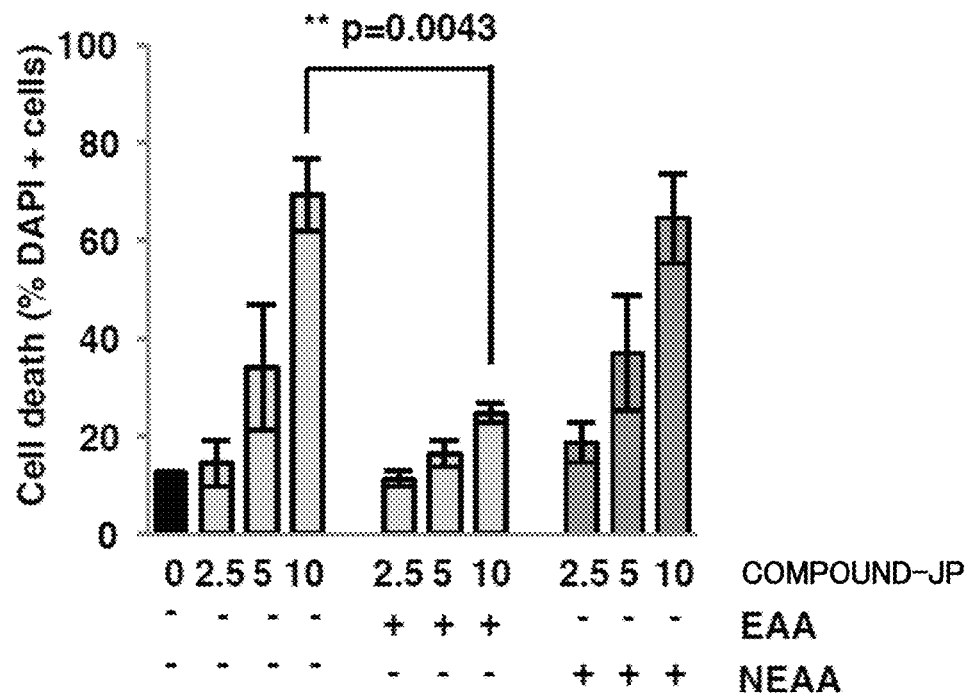
FIG. 2D shows the result that the cell death was analyzed by flow cytometry after DAPI staining, 48 h after treatments (mean of three independent experiments in triplicates+/−SEM, Student's t test).

It has been well established that LAT1 mediates large neutral amino acid uptake (Reference 21); (Reference 22). As depicted in FIG. 2C, incubating KO99L cells with COMPOUND-JP (2.5-10.0 µM) produced a dose-dependent decrease in cell viability which could be partially reversed by supplementing the culture medium with Essential Amino Acids (EAA) whereas Non Essential Amino Acids (NEAA) had no rescue effect. In parallel, as summarized in FIG. 2D, the COMPOUND-JP induced cell death was decreased by 2.5 fold upon EAA addition but not NEAA. These data further demonstrate that COMPOUND-JP functions by altering EAA uptake.

(COMPOUND-JP Interferes with tPTEN−/− Tumor Growth In Vivo)

Figure 2E:
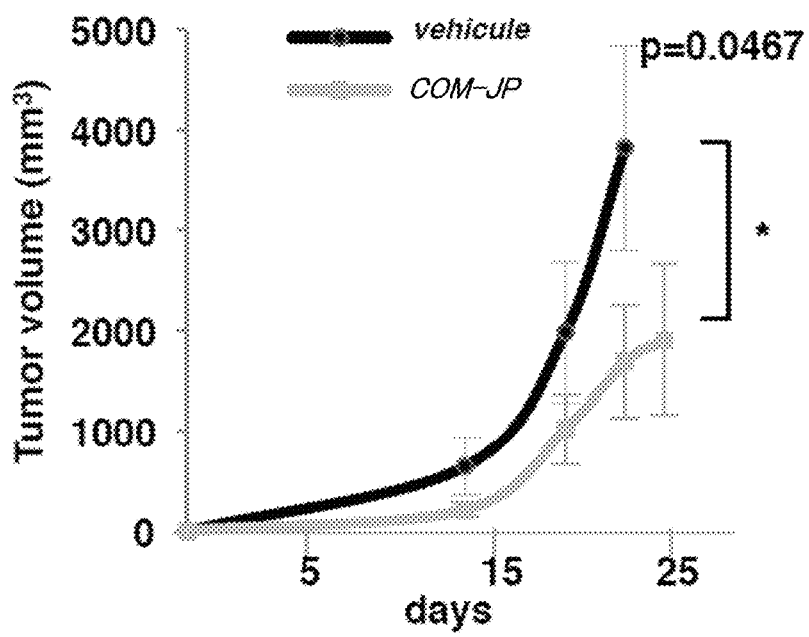
FIG. 2E-G) shows the result that the nude mice were inoculated subcutaneously with KO99L-LUC cells and treated daily with COMPOUND-JP (1.5 mg/mice/day) after 48 h. Measurements of tumor were made after 18 days; mean+/−SEM. Bioluminescence was recorded on a BioImager after intraperitoneal injection of D-luciferin.
Figure 2F:
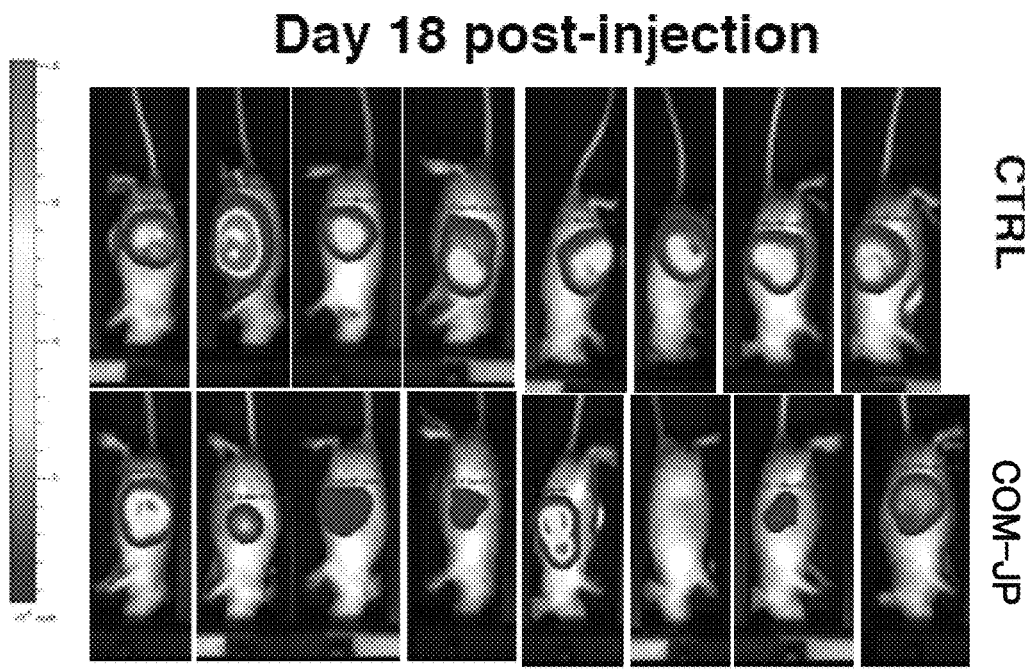
Figure 2G:
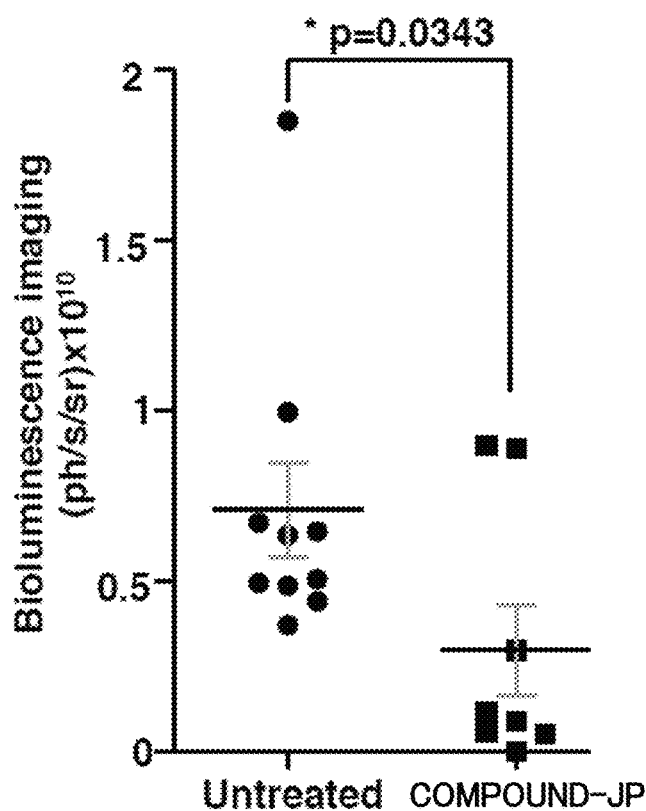
Figure 4A:
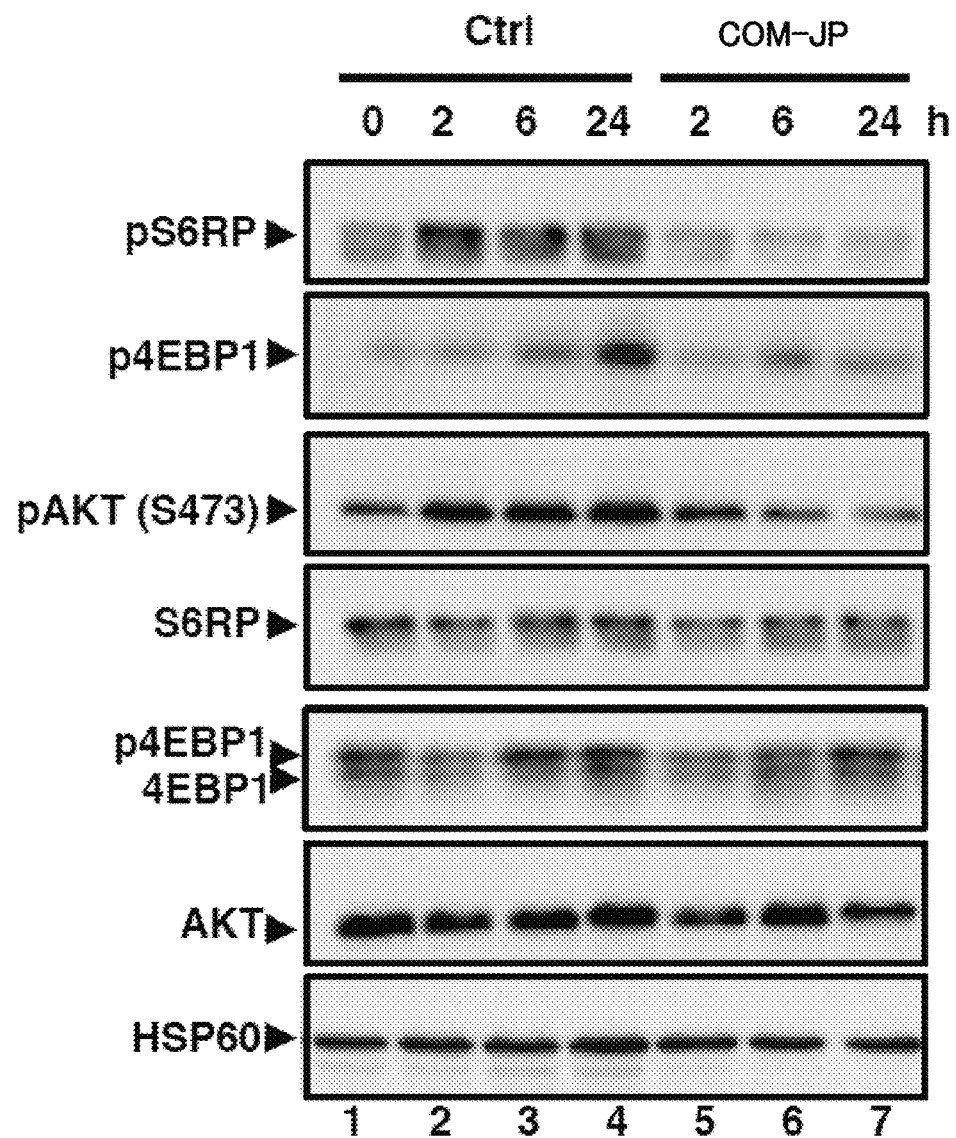
FIG. 4A shows the time course experiment on KO99L cells with indicated doses of COMPOUND-JP. Total cell lysates were analyzed by Western blotting with specified antibodies. Data are representative of at least three independent experiments.
Figure 4B:
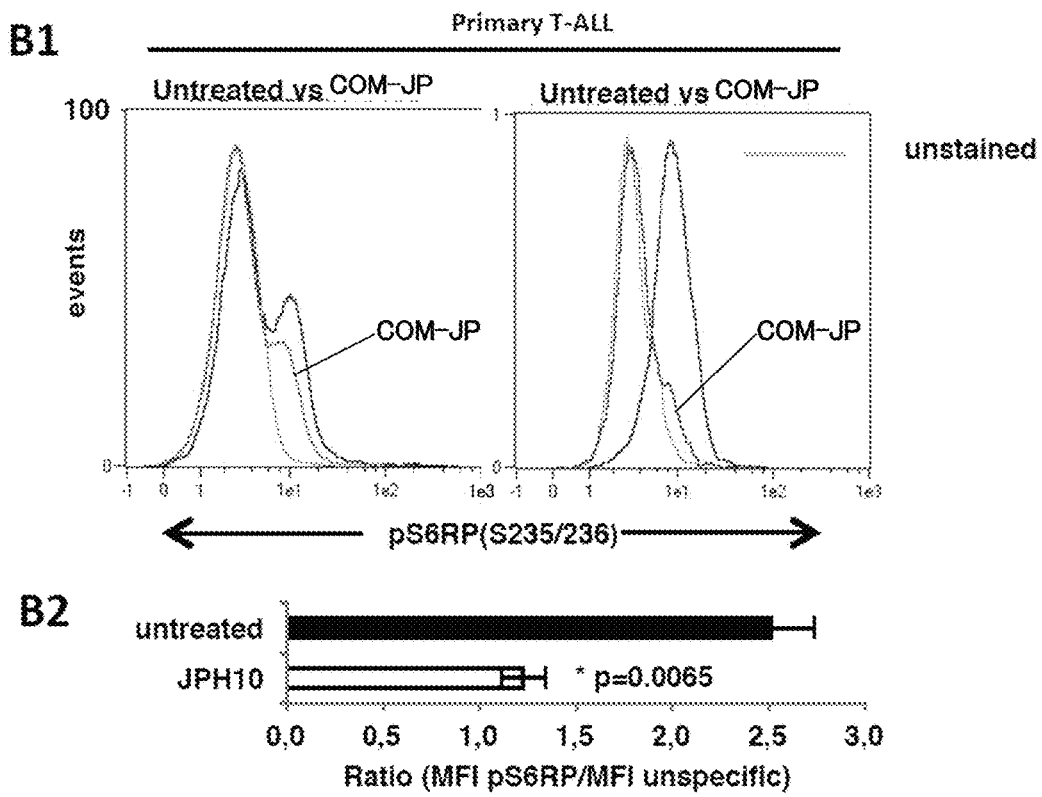
FIG. 4B the Phospho-Flow staining with phospho-S6RP mAb in COMPOUND-JP (10 μM) treated (red/blue line) or untreated T-ALL primary samples (n=2, duplicate) (black line). Isotype control is shown in grey line. (mean+/−SEM). The curves of the untreated or treated samples were normalized to the high of the peak. Events ($10^4$) were acquired for each samples. Conditions were performed in duplicates.
Figure 4C:
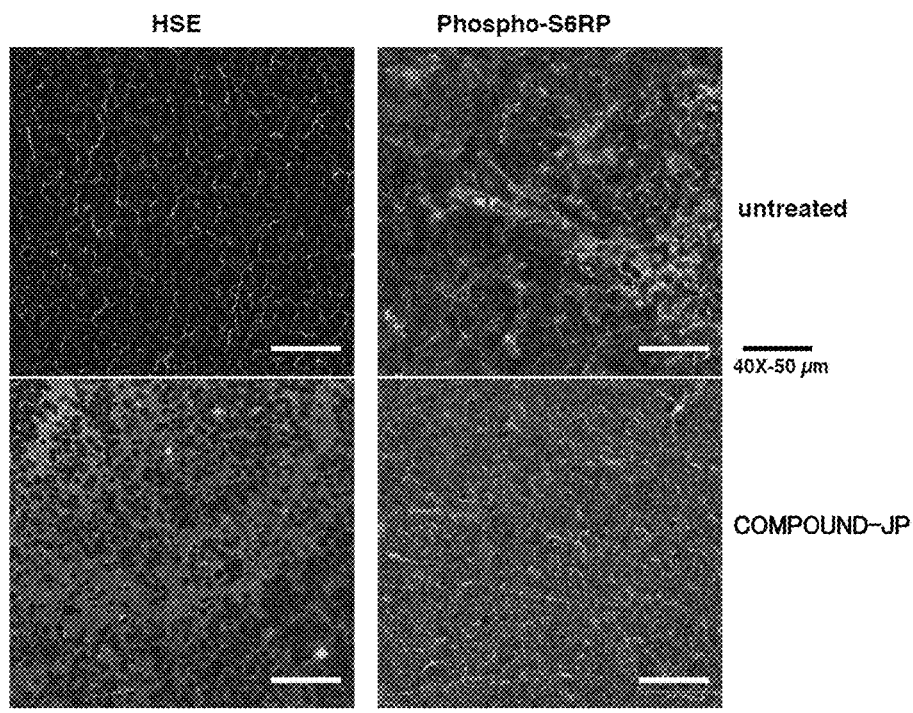
FIG. 4C shows the immunohistochemistry analysis of necrosis (HES staining, left panels) and mTORC1 activation (phospho-S6RP levels, right panels) within tumors in untreated or COMPOUND-JP-treated mice (50 mg/kg/day=1.5 mg/mice/day). Magnification: 40×; scale bars 50 μm.

KO99L cells stably transfected with a luciferase expressing vector were injected subcutaneously into nude mice; thereafter (2 days), animals were treated with COMPOUND-JP (50 mg/kg/day=1.5 mg/mouse/day). Tumor-associated bioluminescence and tumor volume data were collected every five days. Daily COMPOUND-JP treatment decreased the mean tumor volume by 45% (p<0.05) at day 18 as compared to the vehicle treated group (FIG. 2E). Tumor luminescence (FIG. 2F) also illustrated a statistically significant decrease (59%; p<0.05) via COMPOUND-JP treatment (FIG. 2G). Immunohistology analyses of the tumors showed that JPH206 treatment resulted in a necrotic response within the tumors (10.5+/−0.5% vs 4.6+/−0.5%; FIG. 4C).

(COMPOUND-JP Alters Human T-ALL/T-LL Cell Lines and Primary Patient Cells)

Figure 2H:
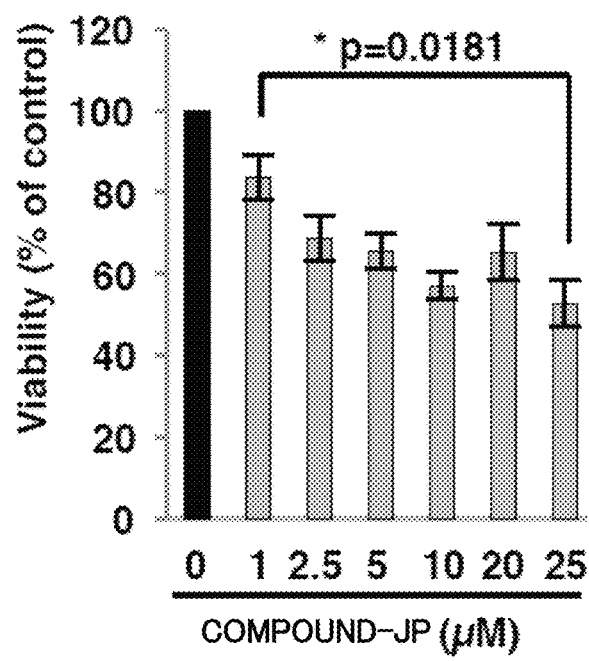
FIG. 2H shows the result of the measurement of cell viability of Jurkat human T-ALL cells, in the presence of indicated doses of COMPOUND-JP. COMPOUND-JP affects T-ALL/T-LL models.
Figure 2I:
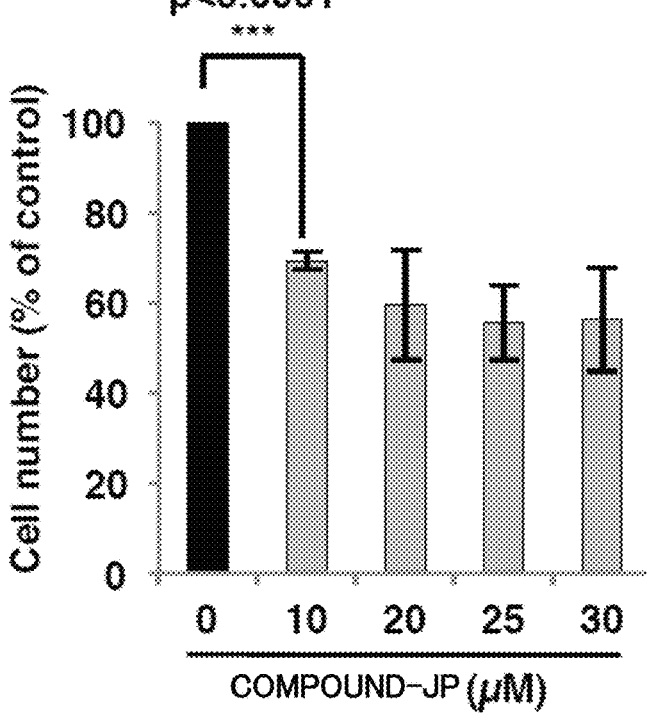
FIG. 2I shows the result of the measurement of cell proliferation measured in the same way (mean of three independent experiments+/−SEM; Student's t test).
Figure 2J:
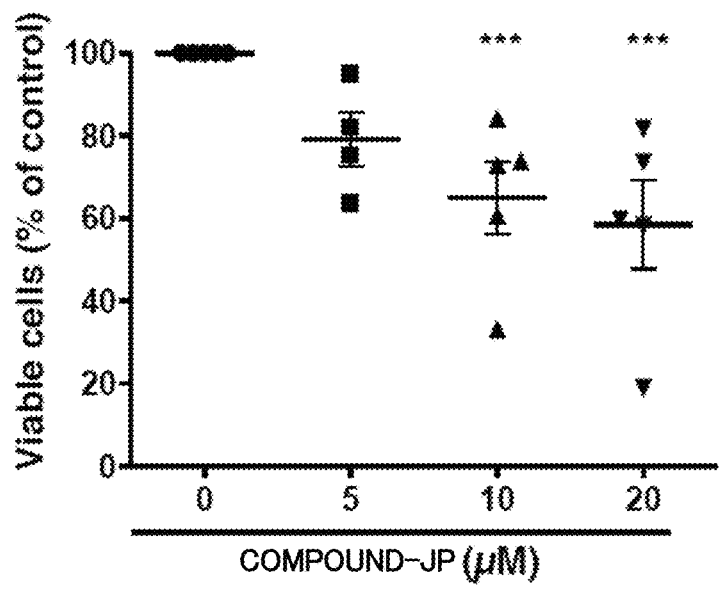
FIG. 2J shows the effect of COMPOUND-JP on cell viability of human T-ALL primary samples (n=5; one experiment, mean+/−SEM; p-value calculated using ANOVA followed by a Dunnett's multiple comparison test; 95% confidence level).
Figure 9D:
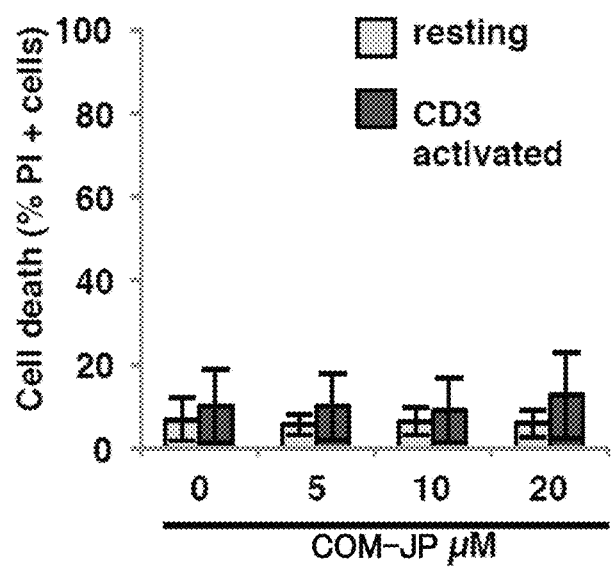
FIGS. 9D, 9E, and 9F show that COMPOUND-JP is not toxic for normal human blood cells.
Figure 9E:
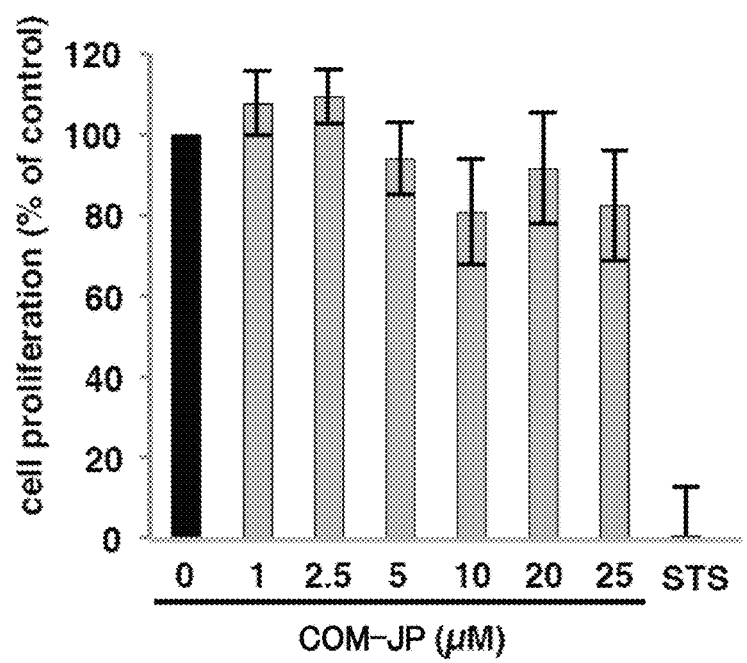
Figure 9F:
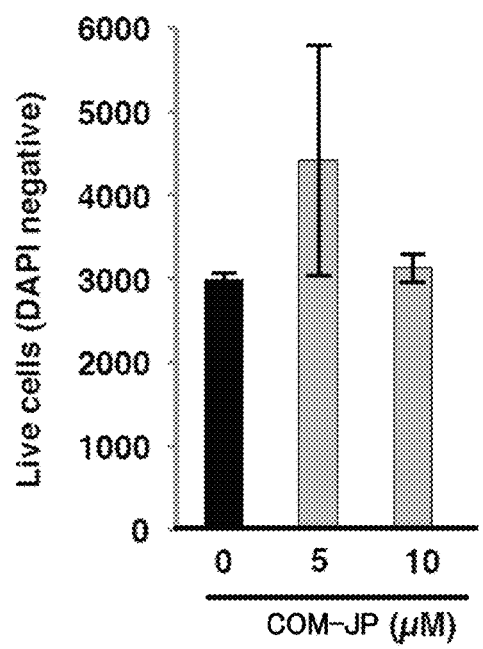

The present inventors sought to establish if LAT1 targeting via COMPOUND-JP could also affect T-ALL/T-LL cell lines and primary tumor cells. The human Jurkat T-ALL line was utilized to demonstrate that COMPOUND-JP could alter cell survival (FIG. 2H) and proliferation (FIG. 2I). In addition, primary T-ALL cells isolated from four different patients also displayed COMPOUND-JP sensitivity (cell viability) in a concentration dependent fashion (FIG. 2J). By strong contrast, COMPOUND-JP did not induce cell death in normal resting or activated human PBL cells (FIG. 9D). Furthermore, in contrast to the apoptotis-inducing agent staurosporine (STS: 1.0 µM) which strongly affected cell proliferation, COMPOUND-JP did not significantly alter PBL cell proliferation (1.0-50.0 µM; FIG. 9E) or normal cord blood mononuclear cells (5.0 and 10.0 µM; FIG. 9F). Consistent with its known LAT1/LAT2 inhibitor selectivity, these experimental results demonstrate that COMPOUND-JP has a preferentially influence toward leukemic cells (LAT1 expressing) compared to normal (healthy, LAT2 expressing) T cells.

(COMPOUND-JP Triggers Apoptosis and Autophagy)

Figure 3A:
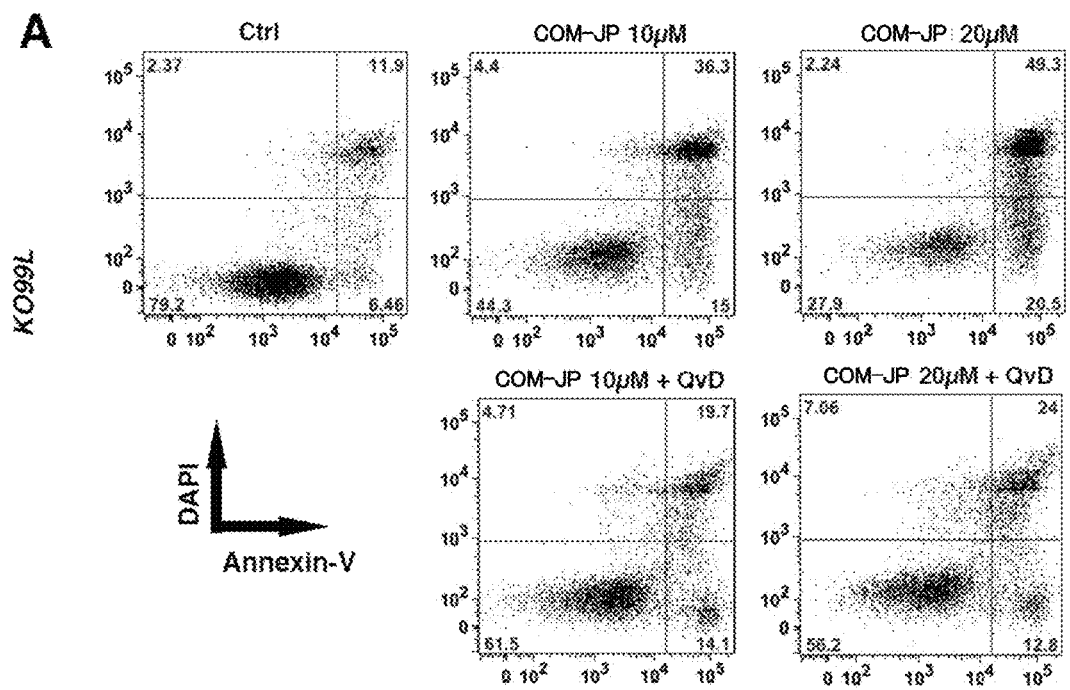
FIG. 3A shows the representative cytometry plots of KO99L cells after a 48 h incubation period with effectors, followed by staining with annexin-V-FITC and DAPI. The % of cells in each state is displayed in the quadrants. Data are representative of five independent experiments.
Figure 3E:
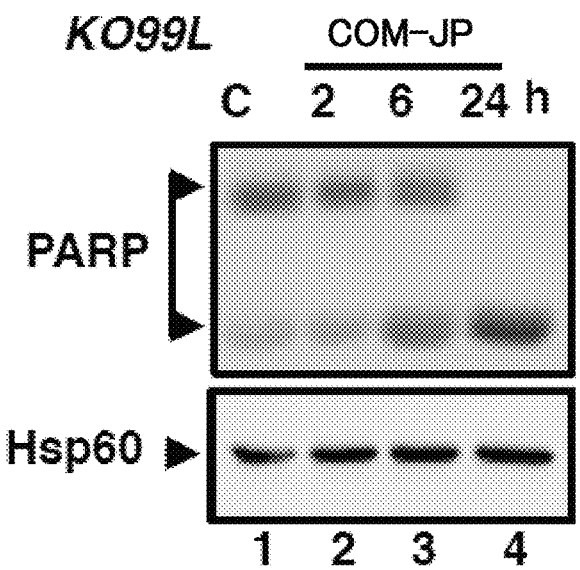
FIG. 3E shows the time course Western blot analysis of PARP cleavage by caspase 3 in KO99L cells.
Figure 3F:
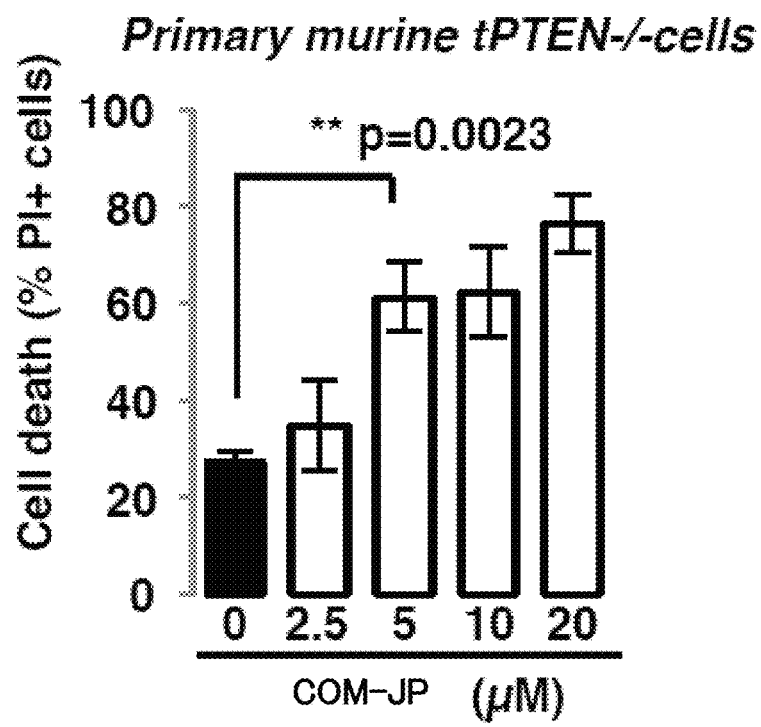
FIG. 3F shows the Cell death induction by COMPOUND-JP in primary tPTEN−/− lines after a 48 h treatment followed by PI staining and Facs analysis (n=5, mean+/−SEM, Student's t test).
Figure 3G:
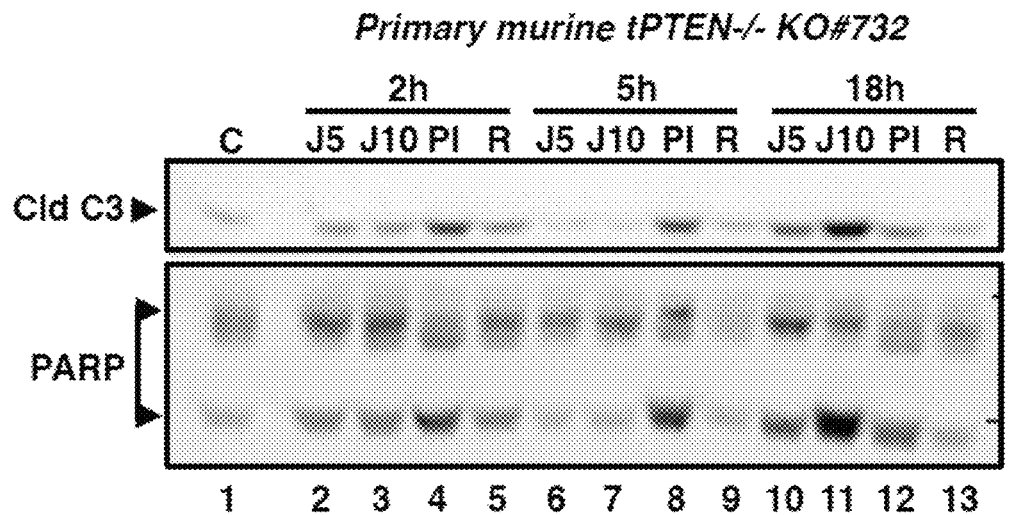
FIG. 3G shows the Western blot analysis of caspase 3 activation and PARP cleavage in primary tPTEN−/− tumor cells. COMPOUND-JP 5.0 μM (J5), 10.0 μM (J10); PI-103 10.0 μM (PI), rapamycin (R: 10.0 nM).
Figure 3H:
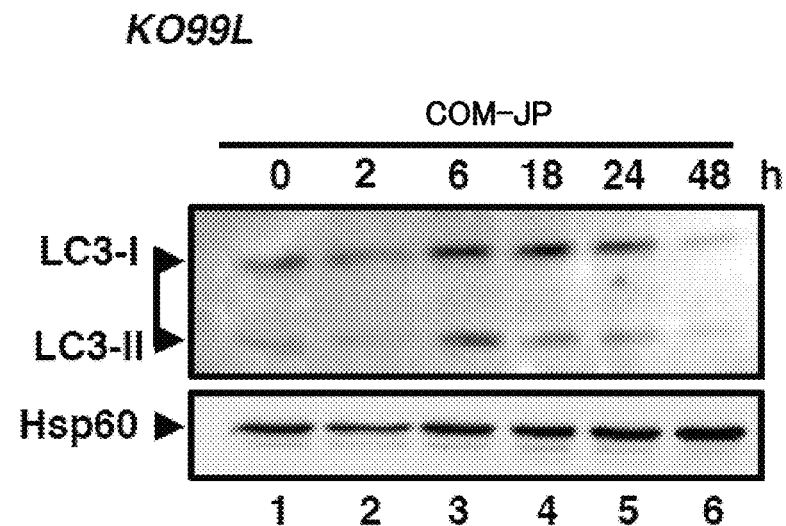
FIG. 3H shows the Western blot analysis of LC3 processing induced by COMPOUND-JP (10.0 μM) in KO99L cells.

COMPOUND-JP exposure to KO99L cells induced apoptosis. Compared to control (no COMPOUND-JP), annexin-V+ and annexin-V+/DAPI+ cell analysis (FIG. 3A) after 48 hr exhibited 2.8 and 3.8 fold higher levels of apoptosis at 10.0 and 20.0 µM, respectively. These results were further confirmed when COMPOUND-JP was co-administered with QvD-OPH (20.0 µM)—an inhibitor which prevents caspase activation—which markedly decreased the quantity of apoptotic cells. Mitonchondrial Outer Membrane Permeabilization (MOMP) is an early apoptotic cell death event that distorts mitochondrial trans-membrane potential (Δψm) (Reference 23). Using the Tetra-Methyl-Rhodamine-Ethyl-Ester Perchlorate staining assay (TMRE), COMPOUND-JP (5.0 and 10.0 µM) was shown to cause MOMP in KO99L cells (FIG. 3B1). The observed mitochondrial depolarization in KO99L cells was found to be COMPOUND-JP concentration dependent (2.5-20.0 µM; 48 hr) reaching 70% at the highest concentration tested (FIG. 3B2). The present inventors monitored caspase activation by examining caspase 3 cleavage over a 48 hr period via Western blotting methods (FIG. 3C). After four-to-six hour post COMPOUND-JP addition (10.0 µM), caspase 3 cleavage could be observed (FIG. 3C, lanes 4 and 5). By 48 hr (lane 8), essentially all cellular caspase 3 was processed. In addition, the present inventors also probed COMPOUND-JP's ability to increase cell-associated fluorescence via Red-DEVD-fmk, a well-known caspase substrate; a result which was returned to baseline upon pre-incubation with QvD-OPH (20.0 µM; FIG. 3D1). As depicted in FIG. 3D2, the COMPOUND-JP results were dose and time-dependent and could be countered by co-administration with QvD-OPH (FIG. 3D1, 2). A caspase 3 substrate, PARP was also observed to be fully cleaved in the presence of COMPOUND-JP (10.0 µM; 24 h) with no observable variations in cellular Hsp60 levels (FIG. 3E, lane 4). COMPOUND-JP was also effective toward primary tPTEN−/− cells and induced cell death in a dose dependent (2.5-20.0 µM) fashion (FIG. 3F; data are mean of five primary tPTEN−/− tumors). Using primary KO#732 cells (FIG. 3G), apoptosis was molecularly confirmed. COMPOUND-JP induced caspase 3 processing and PARP cleavage (18.0 h; lanes 10, 11). Rapamycin had no effect (lanes 5, 9, 13) while PI103 appeared as an early (2.0 h, lane 4) and efficient cell death inducer (lanes 8, 12). As a protective response that may occur during times of nutrient shortage, autophagy may occur prior to apoptosis. As illustrated in FIG. 3H, COMPOUND-JP (10.0 µM) exposure stimulated LC3-II accumulation; LC3-II is the autophagic form of LC3 and associated with the first steps of autophagy (Reference 24). LC3-II accumulation peaked at 6.0 h (FIG. 3H, lane 3) and decreased thereafter (lanes 4-6). As presented in FIG. 3I, the presence of QvD-OPH (20.0 µM) was able to counteract apoptosis and to maintain LC3-II for up to 18.0 h (lane 5 compared to lane 7). Autophagosome formation associated, Atg5 levels increased over time to a maximum at 6.0 h (lane 6) and returned to baseline at 18.0 h (lane 7). Furthermore, pJNK stress pathway activation was detected when apoptosis was blocked (lane 5 compared to 7). Overall, these experimental results support the notion that COMPOUND-JP first triggered an autophagic response, which was rapidly followed by apoptosis.

(LAT1 Inhibition Via COMPOUND-JP Interferes with mTORC1 Activation)

Figure 9G:
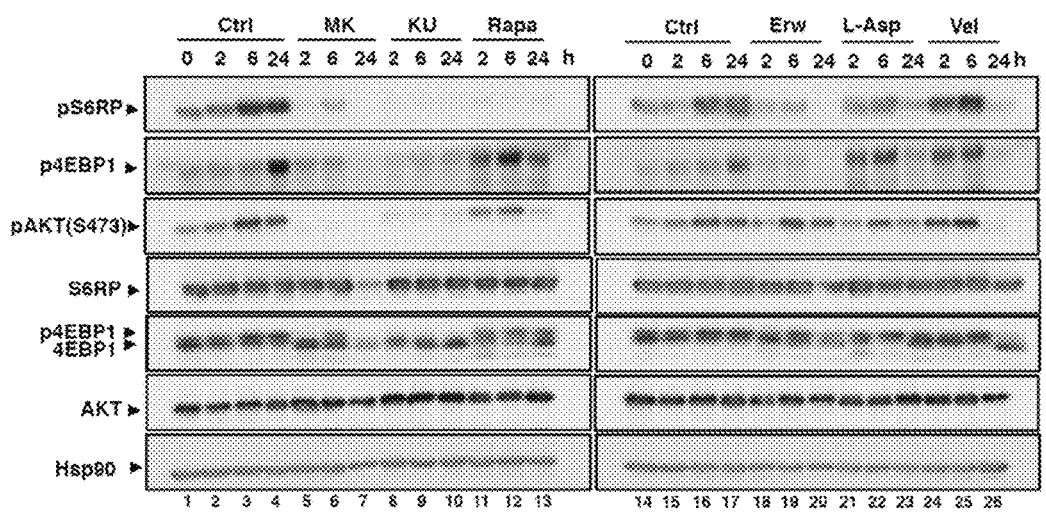
FIG. 9G shows the effect of signaling inhibitors Total cell lysates separated by SDS-PAGE before analysis by western blotting with specified antibodies is shown. Time course experiment on KO99L cells with indicated doses of MK2206 (5 µM), KU0063794 (5 µM), rapamycin (10 nM), Erwinase (2.5 UI/ml), L-Asparaginase (2.5 UI/ml) Velcade (15 nM). Data are representative of three independent experiments.

Established via pS6RP reduction in KO99L cells (FIG. 4A), the present inventors observed that COMPOUND-JP (10.0 µM) could affect mTORC1 activation as early as 2.0 h (lane 5) and was maintained at 6.0 h (lane 6) and 24 h (lane 7). The mTOR inhibitory effect of COMPOUND-JP was also observed by phospho-Flow cytometry on two primary T-ALL samples (FIG. 4B). Moreover, pS6RP staining was dramatically decreased in tumors from COMPOUND-JP-treated mice, demonstrating an in vivo inhibitory effect of the compound (FIG. 4C). In KO99L cells, COMPOUND-JP also interfered with Akt activation as measured by serine 473 phosphorylation (FIG. 4A). In contrast, COMPOUND-JP displayed no effect on 4E-BP1 phosphorylation and demonstrates that COMPOUND-JP only partially perturbs mTORC1 activation. Akt inhibitor MK-2206 (5.0 µM) and Akt/mTOR dual inhibitor KU0063794 (5.0 µM) were shown to completely block S6RP, 4EBP1 and Akt phosphorylation as early as 2.0 h (FIG. 9G). Rapamycin (10.0 nM) resembled the action observed with COMPOUND-JP (10 µM); rapamycin is an mTORC1 inhibitor but not of mTORC2 (Reference 25) which completely inhibited S6RP phosphorylation but not 4EBP1 (FIG. 9G). Rapamycin also affected Akt phosphorylation/activation at later time points compared to COMPOUND-JP (FIG. 9G). As LAT1 has been established to be an extracellular EAA exchanger with intracellular glutamine (Reference 26), the present inventors sought to probe how varying glutamine levels might interfered with EAA influx and mTORC1 activation. For this the present inventors used L-Asparaginase (L-Asp) and Erwinase (Erw), two enzymes that can degrade extracellular asparagine and also possess glutaminase activity. As presented in FIG. 9G, both L-Asp and Erw (2.5 units/ml) altered S6RP phosphorylation; as Erw has a higher glutaminase activity, it was more potent than L-Asp. Compared to control (FIG. 9G; lanes 15-17), Erw (lanes 18-20) and L-Asp (lanes 21-23) also altered 4EBP1 phosphorylation; whereas they did not significantly influence Akt phosphorylation. Inhibiting proteasome activity has been reported to disturb amino acid homeostasis (References 27). In the present inventors' model, the proteasome inhibitor velcade (Vel; FIG. 9G) completely abolished S6RP, 4EBP1 and Akt phosphorylation at 24 h (lane 26), but not at early time points (2.0 and 6.0 h; lanes 24 and 25, respectively). In all these experiments, the total levels of S6RP, 4EBP1, Akt and Hsp 90 were not significantly altered by the different drugs and demonstrates that the observed effects on phosphorylation were not due to differences in protein amounts.

(LAT1 Inhibition and c-myc Protein Level)

Figure 4D:
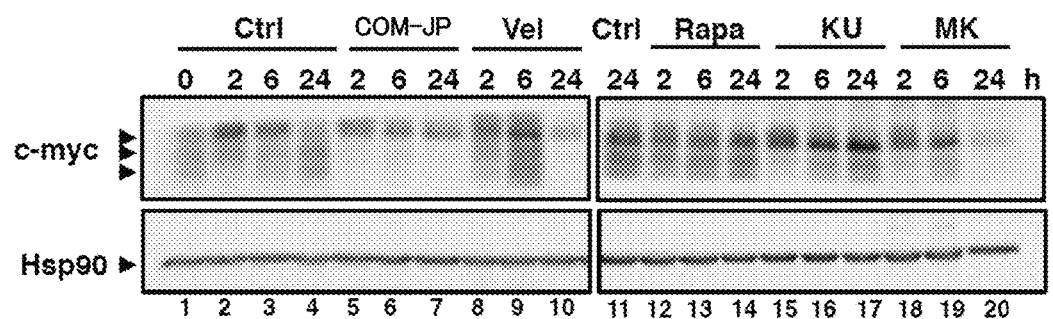
FIG. 4D shows the Western blot analysis of c-myc levels after KO99L cell stimulation with indicated inhibitors: COMPOUND-JP (JPH) (10.0 μM), Velcade (Vel) (15.0 nM), rapamycin (Rapa) (100 nM), KU0063794 (KU) (10.0 μM), MK2206 (MK; 5.0 μM). Data are representative of at least three independent experiments.

The c-myc protein has been shown to be upregulated in human lymphomas and in tPTEN−/− tumors (Reference 28). In tPTEN−/− cells, c-myc was observed to migrate as a triplet around 60 kDa in SDS-PAGE (FIG. 4D; lanes 1-4). Upon cell incubation with COMPOUND-JP (10.0 µM), total c-myc had already decreased at 2.0 h (lane 5) and was maintained up to 24 h (lane 7); in particular, the two lower migrating forms of c-myc were significantly diminished. Analogous observations were present when incubated with Velcade (8 nM; 24 h; lane 10). Akt/mTOR inhibition via KU0063794 (10.0 µM) also slightly influenced the two lower bands (lanes 15-17). MK-2206 (10.0 µM) mediated Akt inhibition resulted in a dramatic disappearance of all three c-myc isoforms within 24 h (lanes 18-20). In sharp contrast to COMPOUND-JP, rapamycin (100 nM) did not affect c-myc levels (lanes 12-14) and attributed to the lack of apoptosis induction. Throughout these various experiments, no Hsp90 level variations could be definitely observed and thereby helps to establish that the different observed drug provoked results were not a function of significant changes in global cellular protein content. Moreover, the present inventors did not observe any interference of COMPOUND-JP with global protein synthesis (data not shown). Collectively, the experimental data are consistent with the notion that c-myc down-regulation produced via COMPOUND-JP may be an important attribute of its anti-leukemic effect.

(COMPOUND-JP Activates the Integrated Stress Response/ Unfolded Protein Response)

Figure 5A:
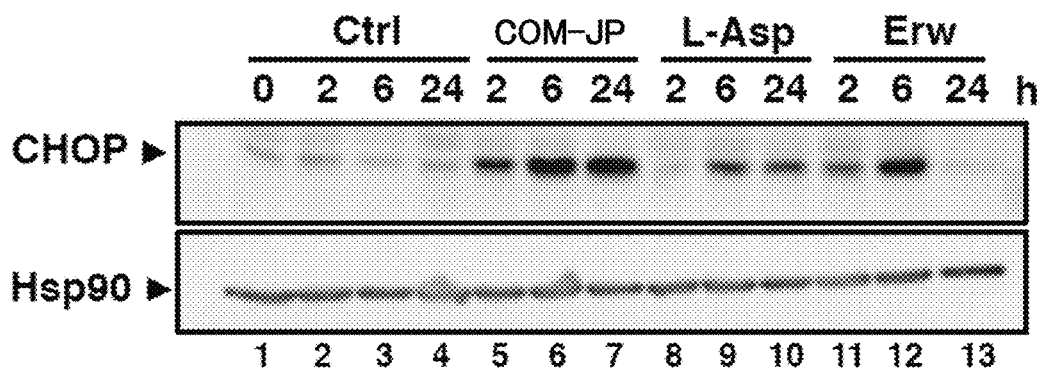
FIG. 5A shows the analysis of CHOP protein levels by Western blotting in KO99L cells. COMPOUND-JP 10.0 μM, L-asparaginase 2.5 UI/ml (L-asp), Erwinase 2.5 UI/ml (Erw).
Figure 5B:
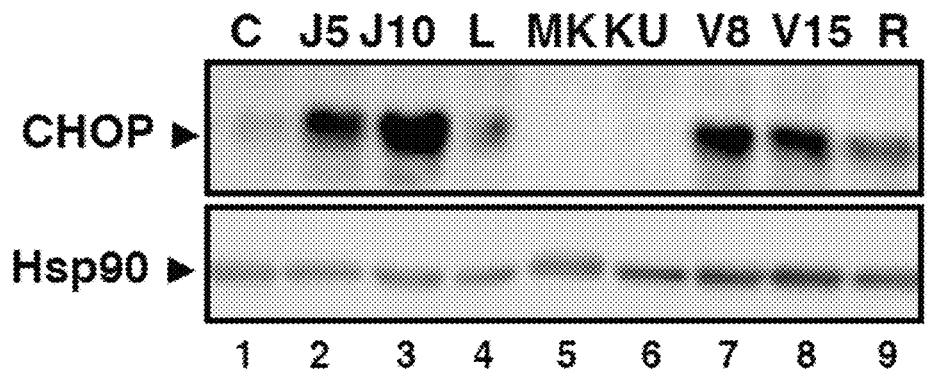
FIG. 5B shows the analysis of CHOP protein levels by Western blotting in KO99L cells. COMPOUND-JP 5.0 μM (J5), 10.0 μM (J10); velcade 8.0 nM (V8), 15.0 nM (J15), rapamycin 10.0 nM (R).

Protein and/or amino acid homeostasis abnormalities are known to trigger an Endoplasmic Reticulum/Integrated Stress Response (ISR)/Unfolded Protein Response (UPR) which can lead to autophagy and cell death (Reference 29). Expression of a transcription factor known as 'C/EBP homologous protein' (CHOP) becomes induced during ER stress and participates in ER-mediated apoptosis (Reference 30). Deregulated CHOP activity compromises cell viability, and cells lacking chop are significantly protected from the lethal consequences of ER stress (Reference 31). When assessed by immunoblotting in KO99L cells, COMPOUND-JP (10.0 µM) rapidly induced CHOP expression by 2.0 h (FIG. 5A, lane 5) which was maximal at 6.0 h (lane 6) and remained stable at 24 h (lane 7). While lower magnitude compared to COMPOUND-JP, CHOP induction by L-Asp (2.5 units/ml) was evident at 6.0 h (lane 9) and 24 h (lane 10). Erw (2.5 units/ml) also induced a transient response which was maximal at 6.0 h (lane 12) and returned to basal levels by 24 h (lane 13). As demonstrated in FIG. 5B, CHOP displayed a profound and COMPOUND-JP dose dependent induction (5.0 and 10.0 µM; lane 2 and 3, respectively); CHOP induction was also strongly induced by velcade (8.0 and 15.0 µM; lanes 7 and 8, respectively) and to a lower extent by L-Asp (2.5 units/ml) and rapamycin (10.0 nM), lanes 4 and 9, respectively. In contrast, Akt and Akt/mTOR inhibitors MK-2206 (10.0 µM; lane 5) and KU0063794 (10.0 µM; lane 6) did not result in CHOP induction which suggests that this pathway is not triggered by the PI3K/Akt/mTOR pathway.

(COMPOUND-JP Induced UPR is Directly Linked to Blocking Essential Amino Acid Uptake)

Figure 5C:
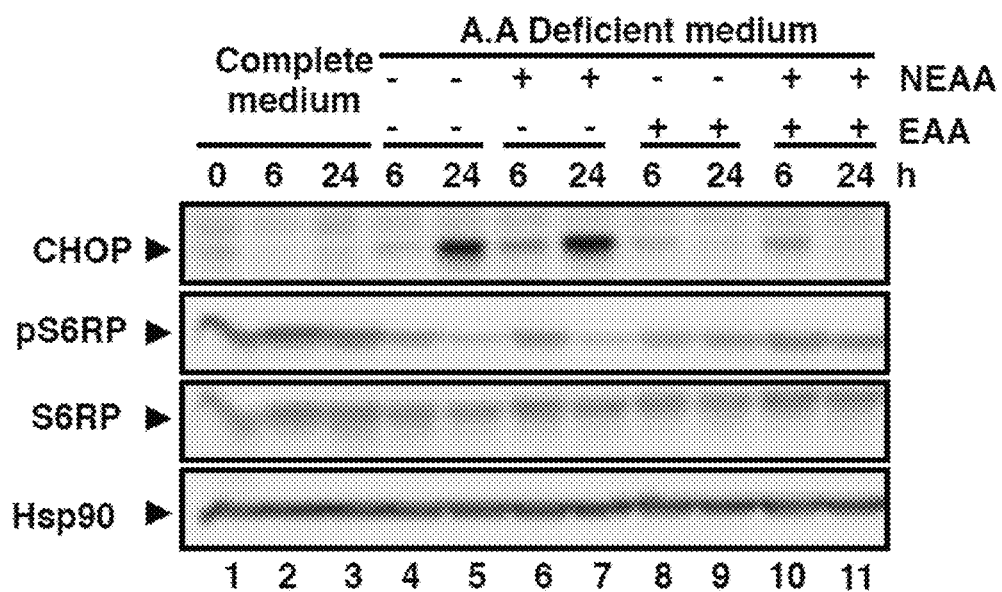
FIG. 5C shows the effect of amino acid depletion/complementation on signaling pathways. Medium was diluted to 10% with HBSS and was supplemented with Non Essential (NEAA) (100×) or Essential (EAA) Amino Acids (50×) before harvest and western blotting analysis.
Figure 5D:
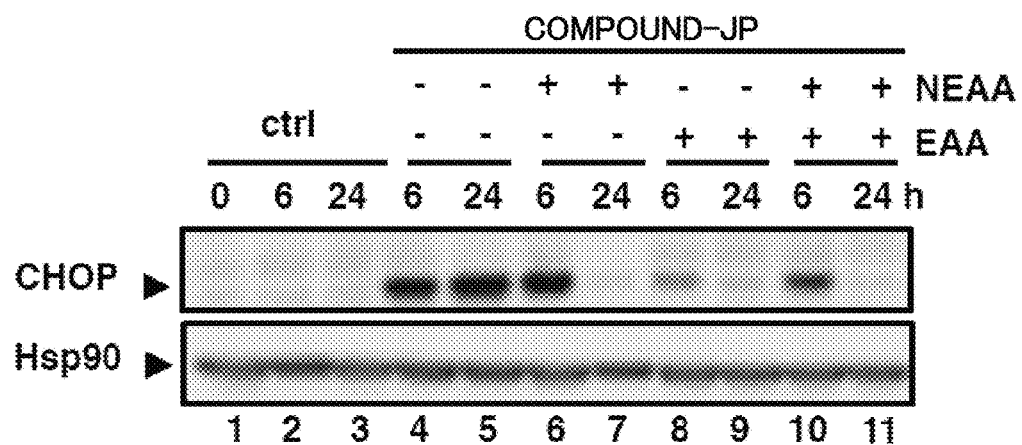
FIG. 5D shows the result in case amino acid were added to complete medium in the presence of COMPOUND-JP (10 µM).

The present inventors next investigated how tPTEN−/− cells response to modifying the media amino acid composition. When complete medium was diluted ten-fold with HBSS (FIG. 5C; 6.0 and 24 h, lanes 4 and 5) a clear time-dependent CHOP induction was observed. Supplementing the nutrient deficient media with NEAA (FIG. 5C; lanes 6 and 7) did not modify CHOP induction while addition of EAA (lanes 8 and 9) or the combination of NEAA+EAA (lanes 10 and 11) prevented CHOP appearance. It was interesting that S6RP phosphorylation inversely correlated with CHOP expression; EAA deficiency in the media lead to mTORC1 down regulation. In addition, the present inventors observed that COMPOUND-JP mediated CHOP induction (FIG. 5D) was modulated via extracellular amino acid content. Indeed, EAA supplementation positively prevented CHOP induction (lanes 8 and 9). NEAA shortened the response as little CHOP protein could be detected at 24 h (lane 7) compared to 6.0 h (lane 6); on the contrary, EAA+NEAA combination showed an intermediate response (lanes 10 and 11). This experimental result illustrate that the COMPOUND-JP triggered stress response can be counterbalanced by increasing extracellular EAA concentration and further demonstrates that the action of COMPOUND-JP is due to inhibiting EAA uptake.

(COMPOUND-JP-Induced CHOP Triggered Apoptosis)

Figure 5E:
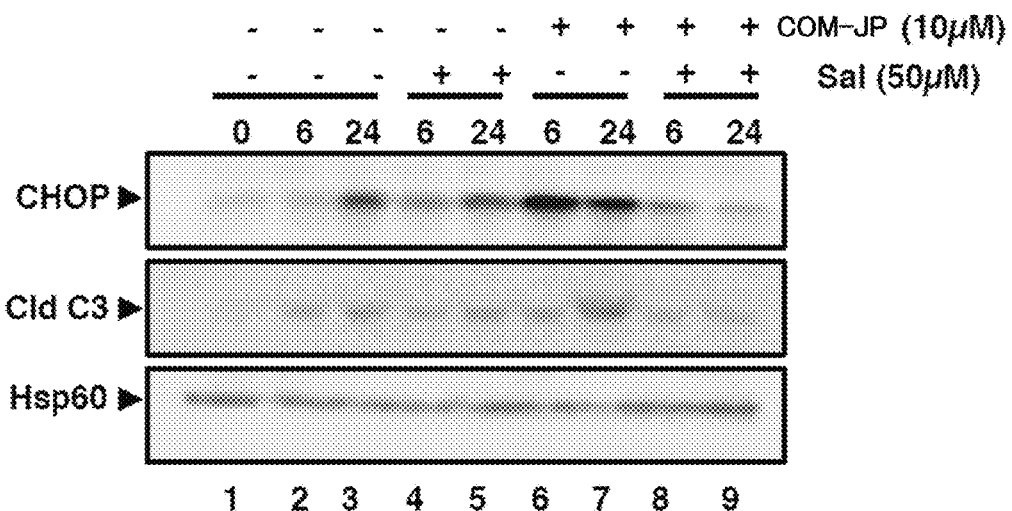
FIG. 5E shows the result in case cells were treated with salubrinal (50 µM) for 30 min before addition of COMPOUND-JP (10 µM).
Figure 5F:
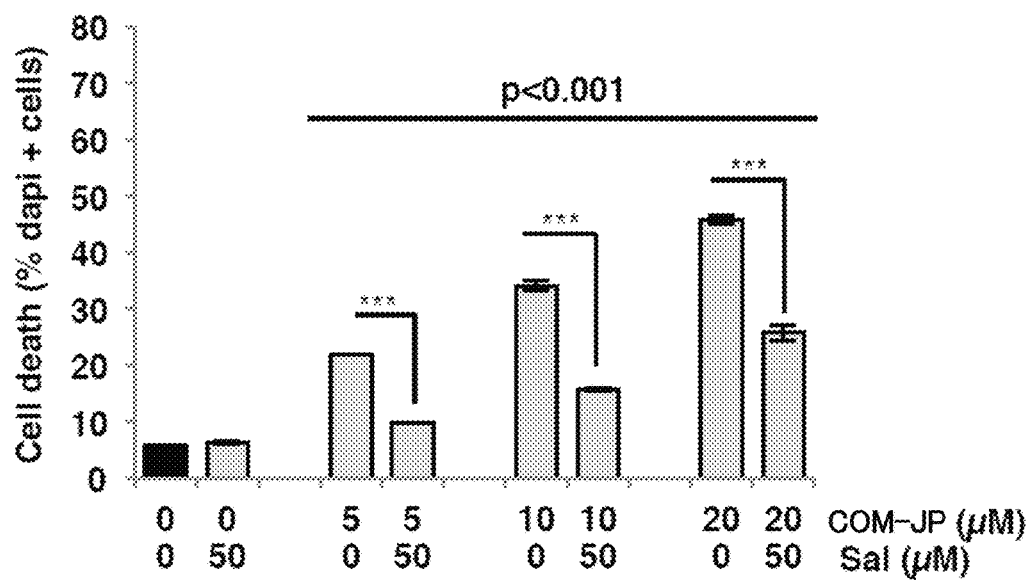
FIG. 5F shows the sensitivity of COMPOUND-JP effects to salubrinal. Cell death visualized by DAPI staining (data are representative of three independent experiments performed in triplicates; mean+/−SEM; Student's t test). Proliferation was assessed by BrdU Elisa
Figure 5G:
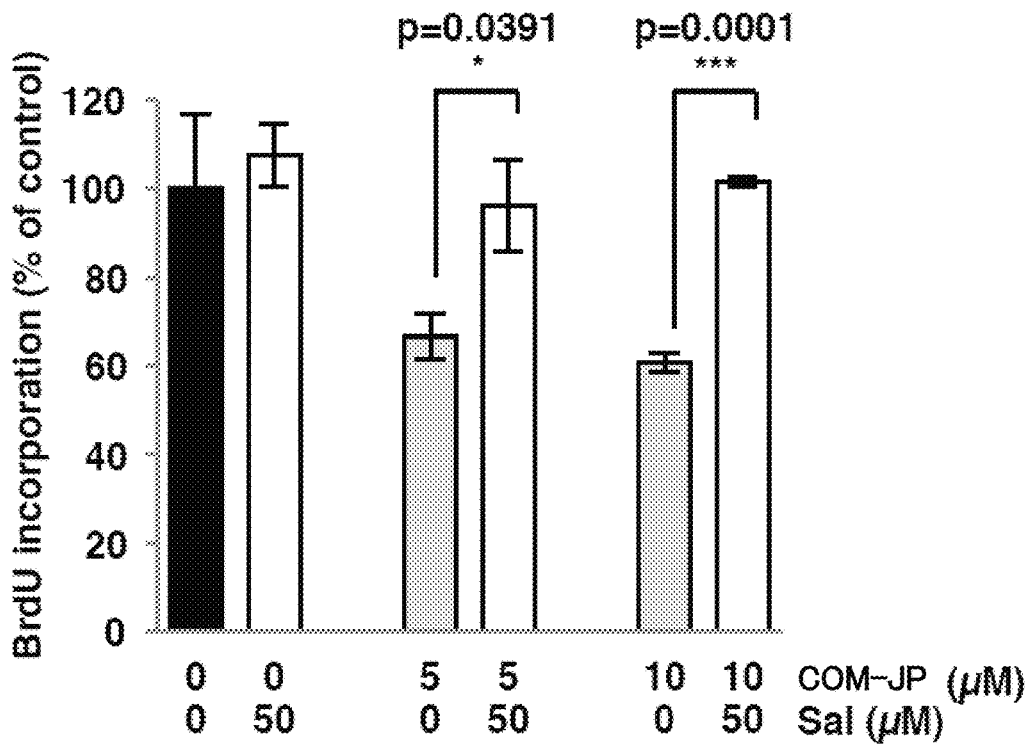
FIG. 5G shows the sensitivity of COMPOUND-JP effects to salubrinal. (one experiment performed in triplicates; mean+/−SEM; Student's t test) or cell counting
Figure 5H:
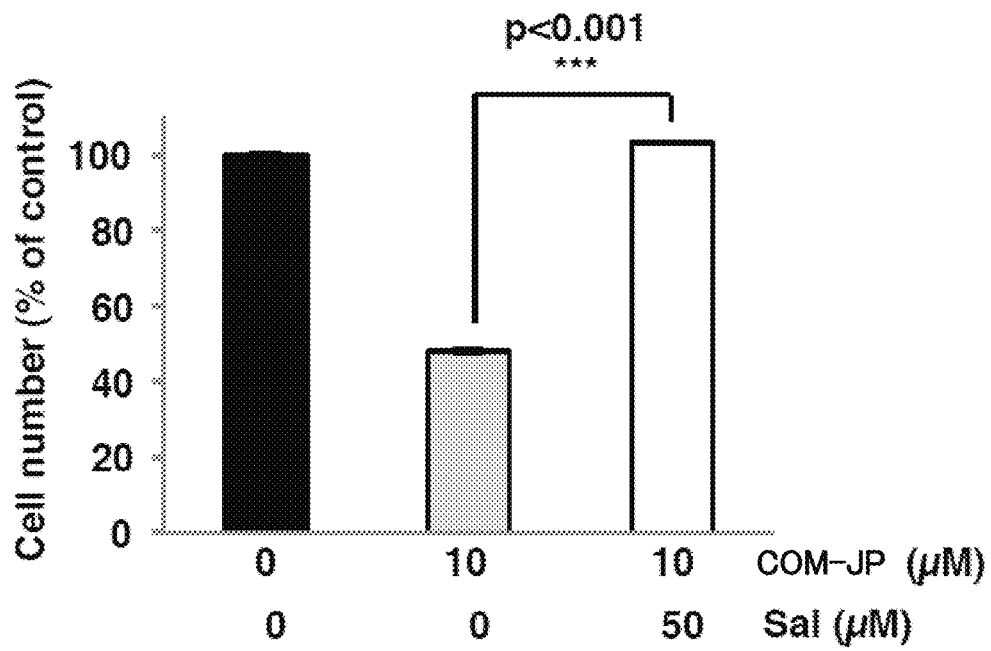
FIG. 5H shows the sensitivity of COMPOUND-JP effects to salubrinal. (data are representative of three independent experiments performed in triplicates; mean+/−SEM; Student's t test).

To examine if the ISR/UPR observed via COMPOUND-JP (LAT1 inhibition) was responsible for the subsequent apoptosis, the present inventors used the salubrinal compound; established as an inhibitor which prevents eIF2☐ de-phosphorylation and induced cell protection towards ER stress (32). As represented in FIG. 5E, salubrinal (50.0 µM) could offset CHOP induction by COMPOUND-JP (10.0 µM) (lanes 8 and 9 compared to 6 and 7). In addition, these results were also accompanied by decreased caspase 3 cleavage (middle panel) while Hsp60 levels remained unchanged (lower panel). Furthermore, salubrinal (50.0 µM) could rescue KO99L cells against cell death induced via COMPOUND-JP (FIG. 5F) and restored cell proliferation evaluated by BrdU incorporation (FIG. 5G) or cell counting (FIG. 5H). These results demonstrate that COMPOUND-JP can trigger CHOP induction during the cell death response.

(Molecular Events in the UPR Pathway Induced by COMPOUND-JP)

Figure 6A:
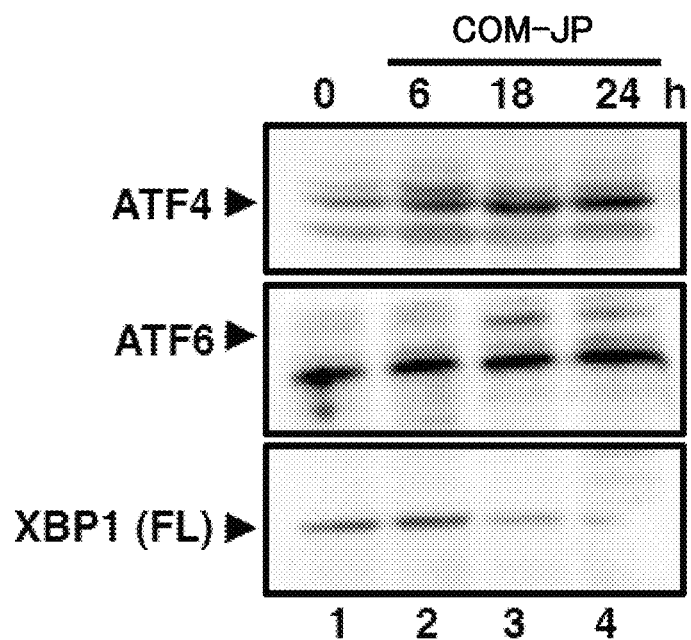
FIG. 6A-C shows the time course Western blot analysis of ISR components upon COMPOUND-JP (10 µM) stimulation of KO99L cells.
Figure 6B:
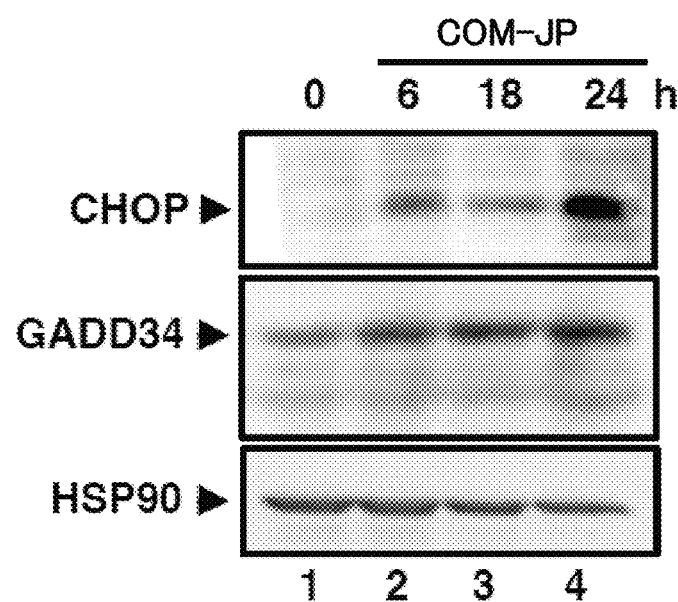
Figure 6C:
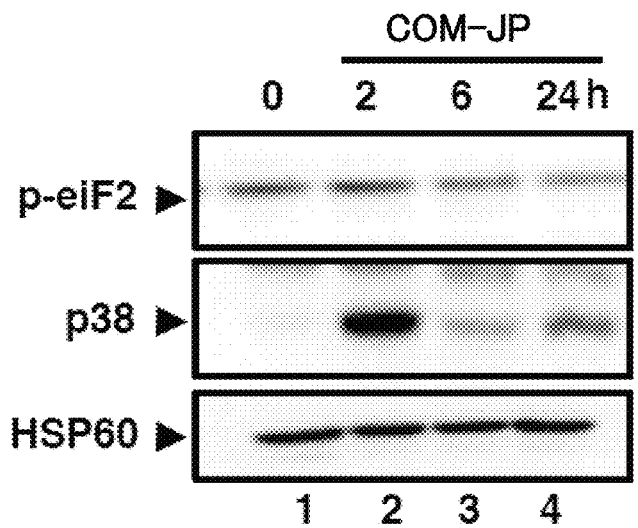

Unfolded Protein Response (UPR) is characterized by coordinated activation of multiple ER proteins which include: i) inositol-requiring enzyme 1 alpha (IRE1☐); ii) PKR-like ER kinase; and iii) Activating Transcription Factor (ATF6) (reviewed in (Reference 33)). Activated IRE1☐ initiates unconventional splicing of the mRNA encoding an isoform of transcription factor XBP-1 that induces expression of chop ((Reference 30). Activated PKR-like ER kinase phosphorylates eIF2☐ (serine-51A) which results in ATF4 translational induction (Reference 34). ATF6 gets cleaved during ER stress, and its cytosolic domain [ATF6(N)] will translocate to the nucleus to regulate transcription (Reference 35). XBP-1, ATF4 and ATF6 are the three transcription factors known to induce chop during ER stress (Reference 30). The present inventors therefore examined, ATF4, ATF6 and the status of XBP-1, after cell incubation with COMPOUND-JP (10.0 µM). The present inventors observed ATF4 (6.0 h) and ATF6 (18.0 h) induction while full length XBP1 gradually disappeared (FIG. 6A; lanes 3 and 4) with concurrent CHOP and GADD34 expression (FIG. 6B; lanes 3 and 4). De-phosphorylation of eIF2☐ was observed at 24 h with paralleled expression of the GADD34 phosphatase (FIG. 6C). The p38 stress pathway was strongly activated at 2.0 h (FIG. 6C; lane 2).

(COMPOUND-JP Modulates Pro- and Anti-Apoptotic Bcl2 Family Members)

Figure 6D:
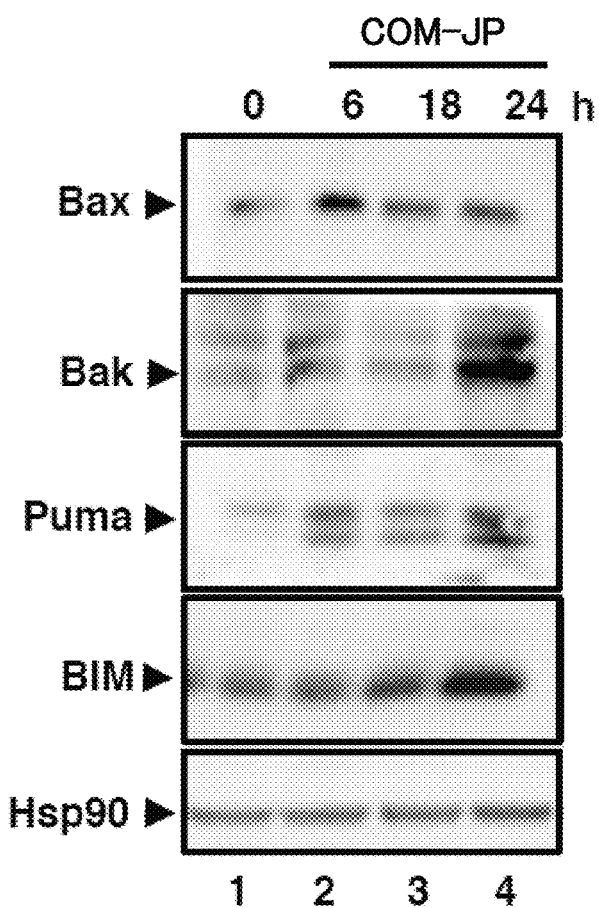
FIG. 6D shows the time course Western blot analysis of Bcl2 family members upon COMPOUND-JP (10 µM) stimulation of KO99L cells.
Figure 6E:
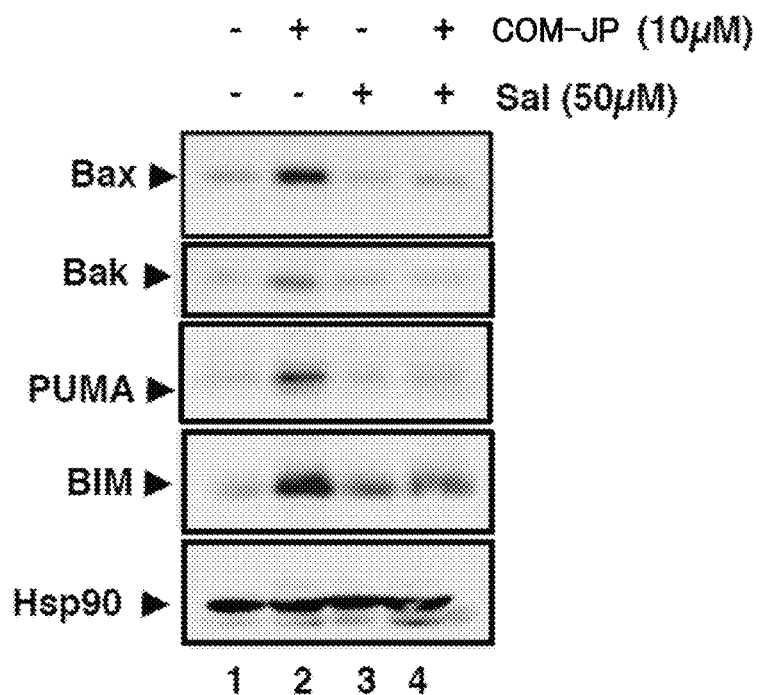
FIG. 6E shows the effect of salubrinal on COMPOUND-JP-induced Bcl2 family members. Hsp90 was used as a loading control. All data are representative of at least three independent experiments.

In order to molecularly define apoptosis induction via COMPOUND-JP, the present inventors analyzed Bcl2 family members; the present inventors sought to measure the members known to control initiation of apoptosis at the mitochondrial and ER membrane level. Starting at 6.0 h (FIG. 6D), COMPOUND-JP (10.0 µM) increased protein levels of four pro-apoptotic members: Bak (FIG. 6D; lanes 2-4), Bax (lane 4), PUMA (lanes 2-4) and Bim (lanes 3 and 4). The induction of Bax, Bak, PUMA and Bim was sensitive to inhibition of CHOP by salubrinal (FIG. 6E, lanes 3 and 4), while total Hsp90 protein levels were not affected.

(KO99RJ Cells: a COMPOUND-JP Resistant Variant)

Figure 7A:
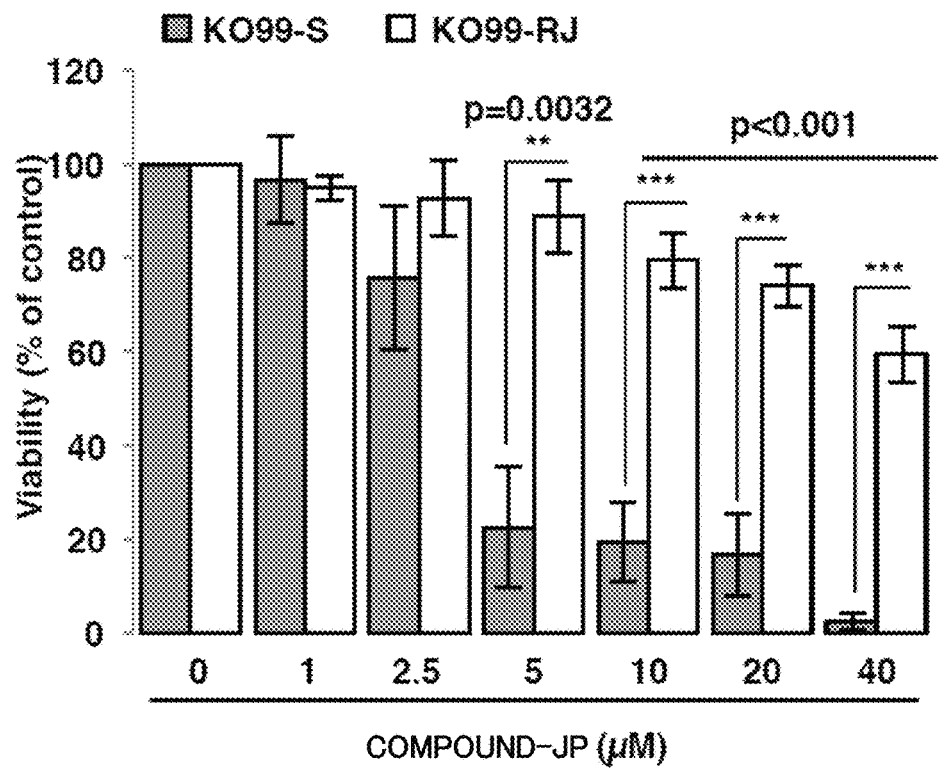
FIG. 7A-C shows the result that KO99L cells parental cells that are sensitive to COMPOUND-JP (KO99-S) were incubated over several months with increasing concentrations of the drug and surviving resistant cells (KO99-RJ) were obtained.
Figure 7B:
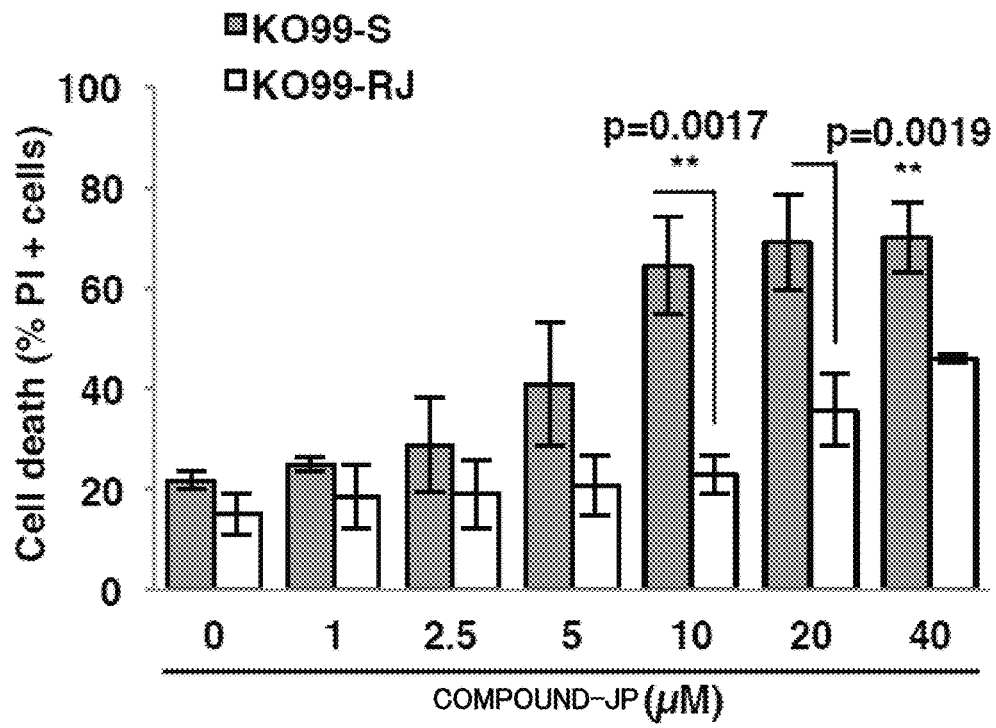
Figure 7C:
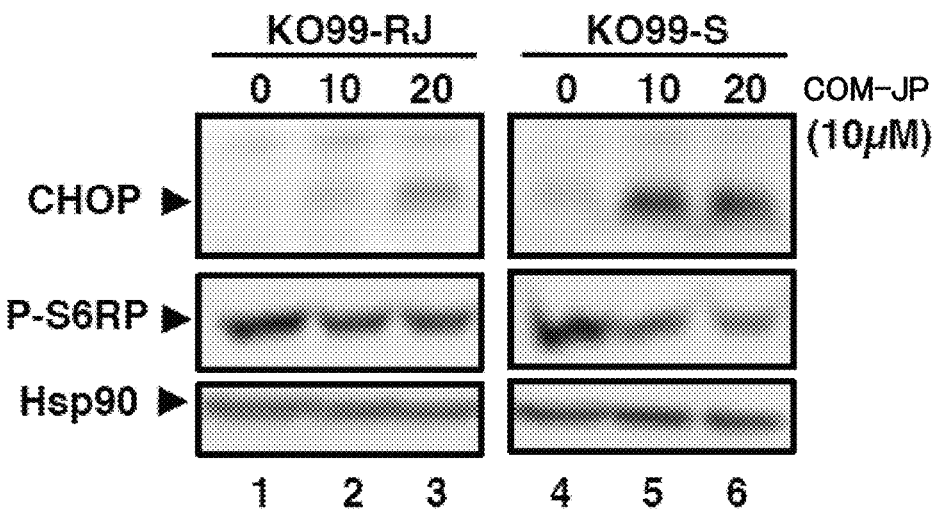

By regularly culturing KO99L cells with increasing concentrations of COMPOUND-JP, the present inventors were able to obtain a cellular variant that resisted COMPOUND-JP's anti-proliferative and apoptotic effects. After approximately 4 months, the present inventors obtained the cell line denoted as KO99-RJ which could still proliferate in the presence of COMPOUND-JP (20.0 µM). As summarized in FIG. 7A, the decrease in cell viability was COMPOUND-JP dose-dependent and far more potent in the parental line (i.e. KO99-S) compared to the variant cell line (i.e. KO99-RJ); for example, at 40 µM COMPOUND-JP cell viability decreased by approximately 40% in KO99-RJ versus essentially 95-100% for KO99-S. As illustrated in FIG. 7B, COMPOUND-JP displayed concentration dependent cell death in KO990-S but was far less efficient in KO99-RJ. Furthermore, as established by the absence of CHOP induction (FIG. 7C) it was interesting to observe that COMPOUND-JP failed to trigger the integrated stress response in the KO99-RJ cells. These data further accentuate the important role of this pathway which triggers the apoptotic response induced via COMPOUND-JP. Lastly, as no decrease in S6RP phosphorylation could be observed (FIG. 7C) COMPOUND-JP also failed to inhibit mTOR in KO99-RJ; KO99-RJ expresses CD98 at comparable levels with parental cells (data not shown).

(COMPOUND-JP Potentiates Chemotherapeutic Drugs and Signaling Inhibitors)

Figure 9H:
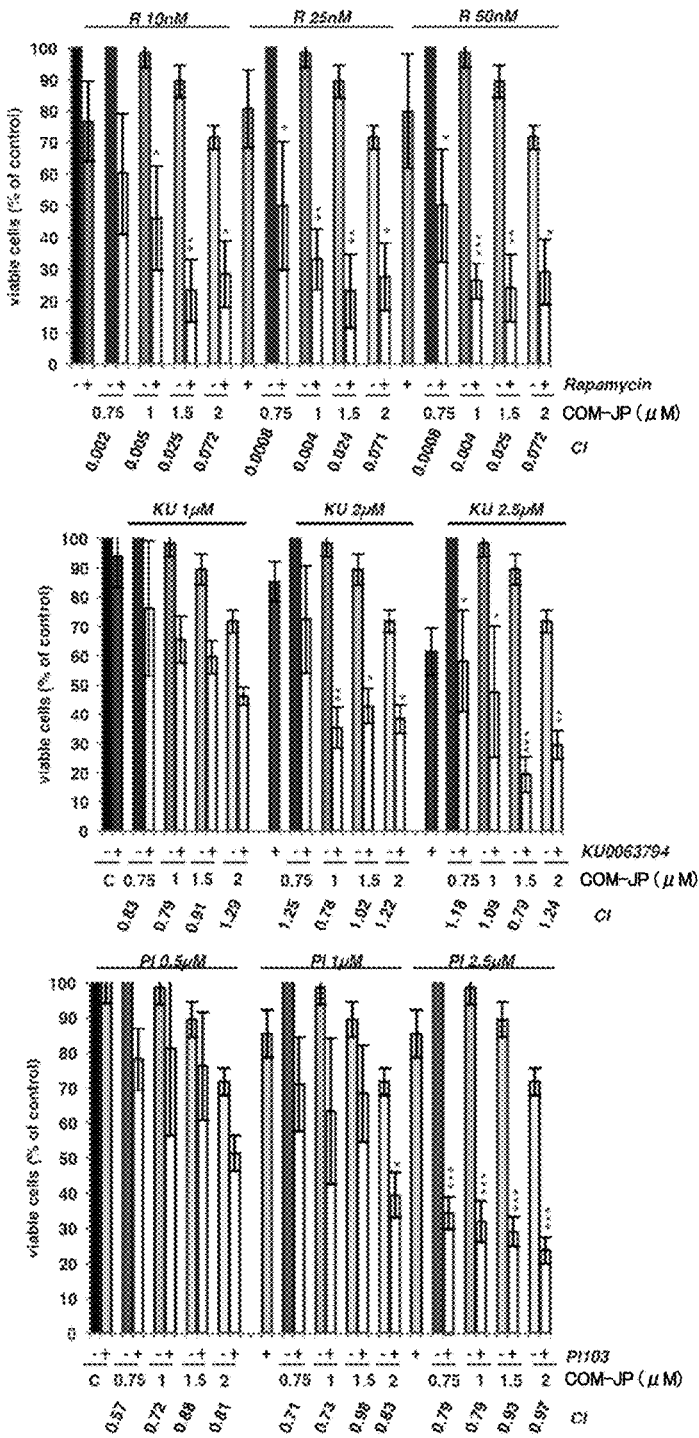
FIGS. 9H and 9I show the combination studies. KO99L tPTEN−/− cells were incubated with COMPOUND-JP associated with other drugs for 48 h at indicated concentrations before viability measurement using a WST1 assay.
Figure 9I:
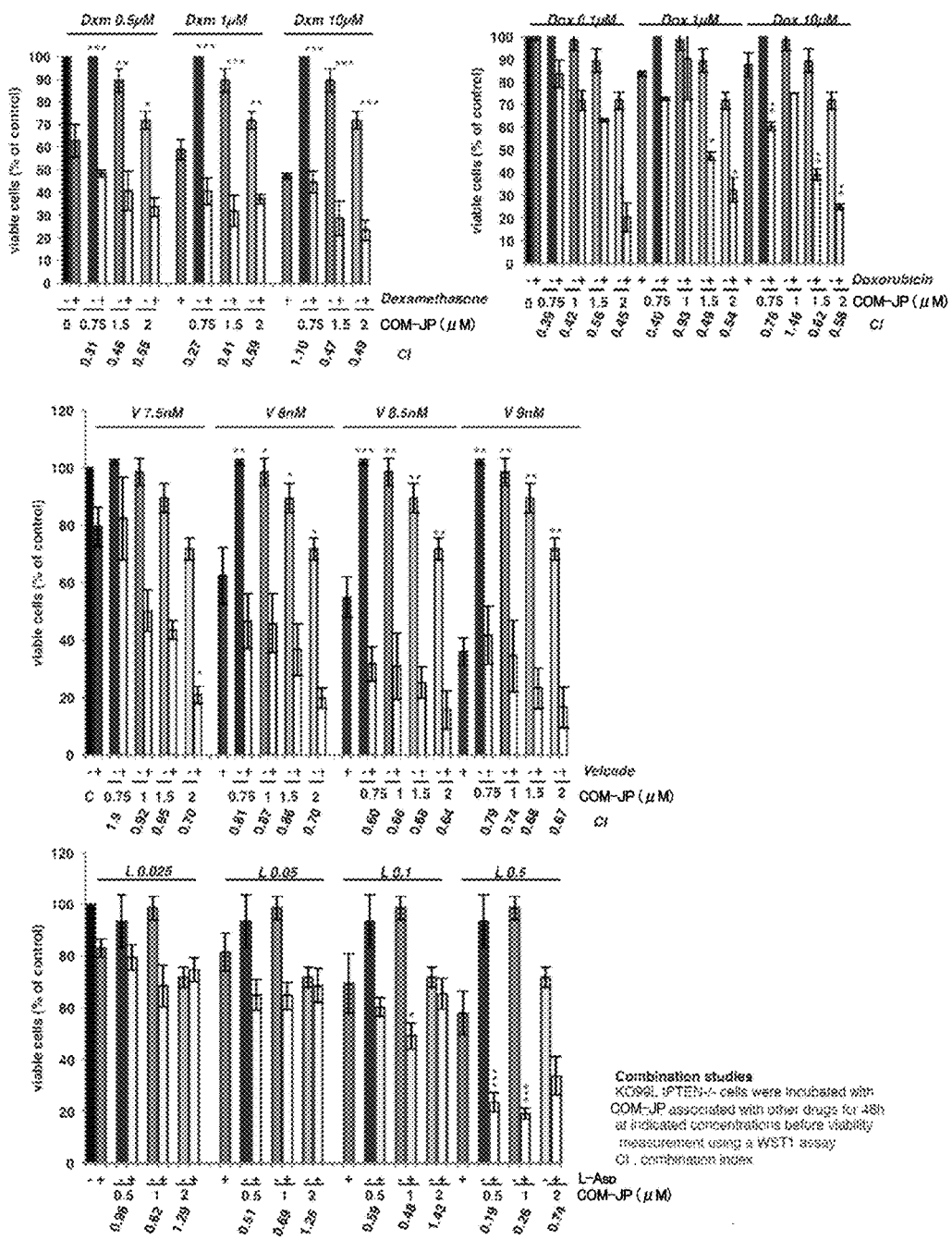

As represented in FIG. 8, COMPOUND-JP was tested (in vitro) in combination with various chemotherapeutic drugs or signaling inhibitors. The present inventors tested dexamethasone and doxorubicin, two chemotherapeutic agents used clinically during the induction phase of leukemia treatments (Reference 36). In these experiments, all compounds were used at suboptimal concentrations and these results are presented in supplemental materials FIGS. 9H and 9I. The computed Combination Index (CI) values are displayed in FIG. 8A. COMPOUND-JP appears to strongly synergize with rapamycin to decrease overall metabolic activity/cell survival. Synergistic or additive effects were observed with all compounds, in particular COMPOUND-JP showed synergy with dexamethasone and doxorubicin. The LAT1 inhibitor could potentiate the effects of velcade and of L-Asparaginase, but appeared less efficient with PI103 and KU-0063794. WST1-derived isobolograms further illustrate the potential of the different combinations tested (FIG. 8B). Overall, the data show that COMPOUND-JP can produce positive effects when combined with other molecules that interfere with T-ALL cell survival (Quantitative Results of a Neutral Amino Acid Transporter, LAT1 Gene and LAT2 Gene Expressed in an Established Culture Cell Derived from Various Cancers of a Human Being)

Figure 10:
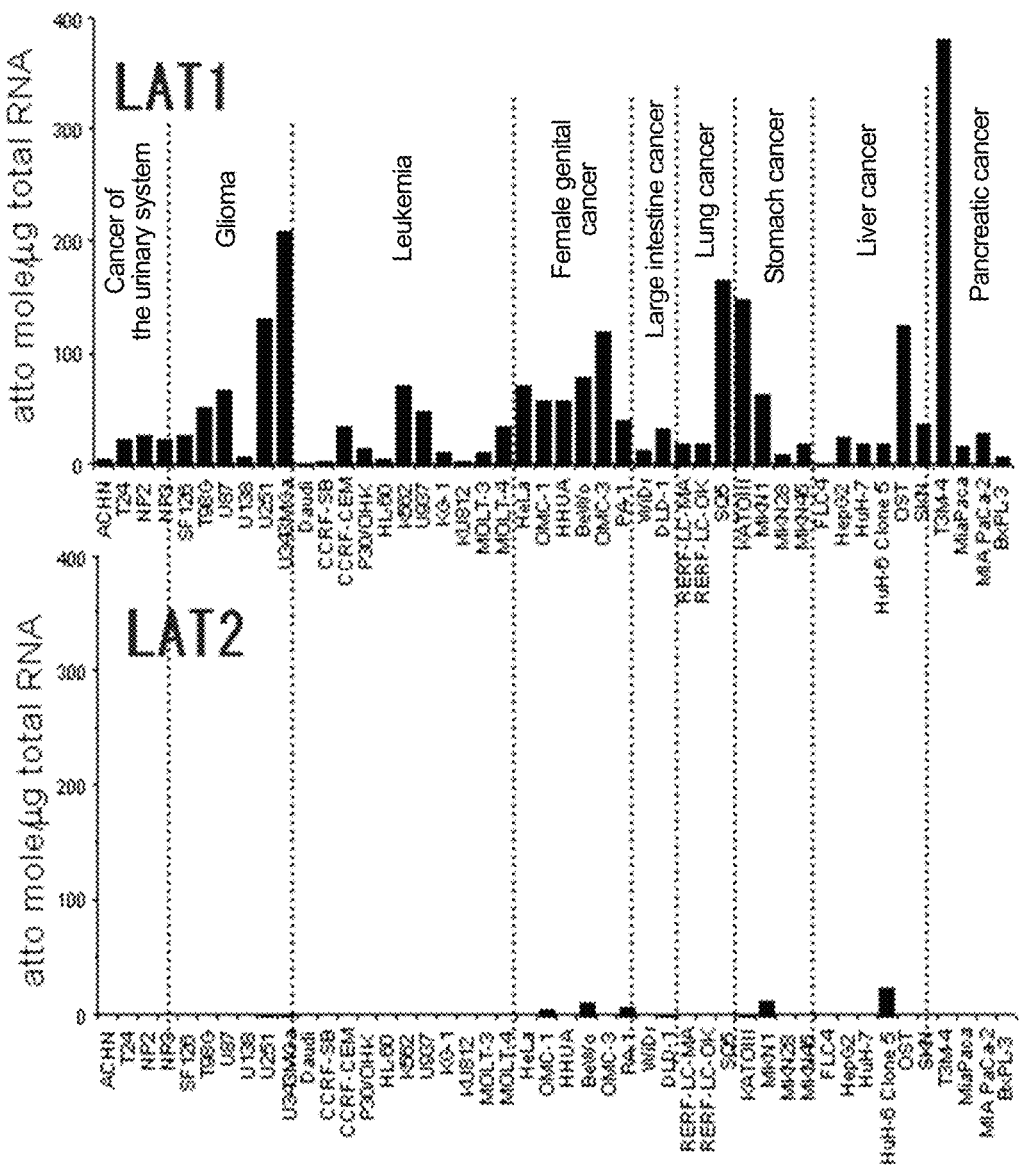
FIG. 10 is a diagram showing quantitative results of a neutral amino acid transporter expressed in an established culture cell derived from various cancers of a human being, and LAT1 and LAT2 genes. Cancer classification name was described in the table with the vertical axis as an amount of mRNA per an RNA unit and with the horizontal axis as the name of cancer cell used. LAT1 was described in the lower section and LAT2 was described in the lower section.

In FIG. 10, cancer classification name was described in a table with a vertical axis as an amount of mRNA per an RNA unit and with a horizontal axis as name of cancer cell used. Except for five exceptions, the LAT1 mRNA was expressed in all of the 46 kinds of cells, and it can be said to be a cancer-type transporter. On the other hand, the expression of the LAT2 is zero or extremely low level in a cancer cell, and it can be understand to be a normal type.

(Inhibitory Effect of a LAT1 Selective Inhibitor, COM-JP on the Proliferation of a 44As3-11 Cell Derived from Human Scirrhous Stomach Cancer and a Panc-1 Cell derived from Human Pancreatic Cancer)

Figure 11:
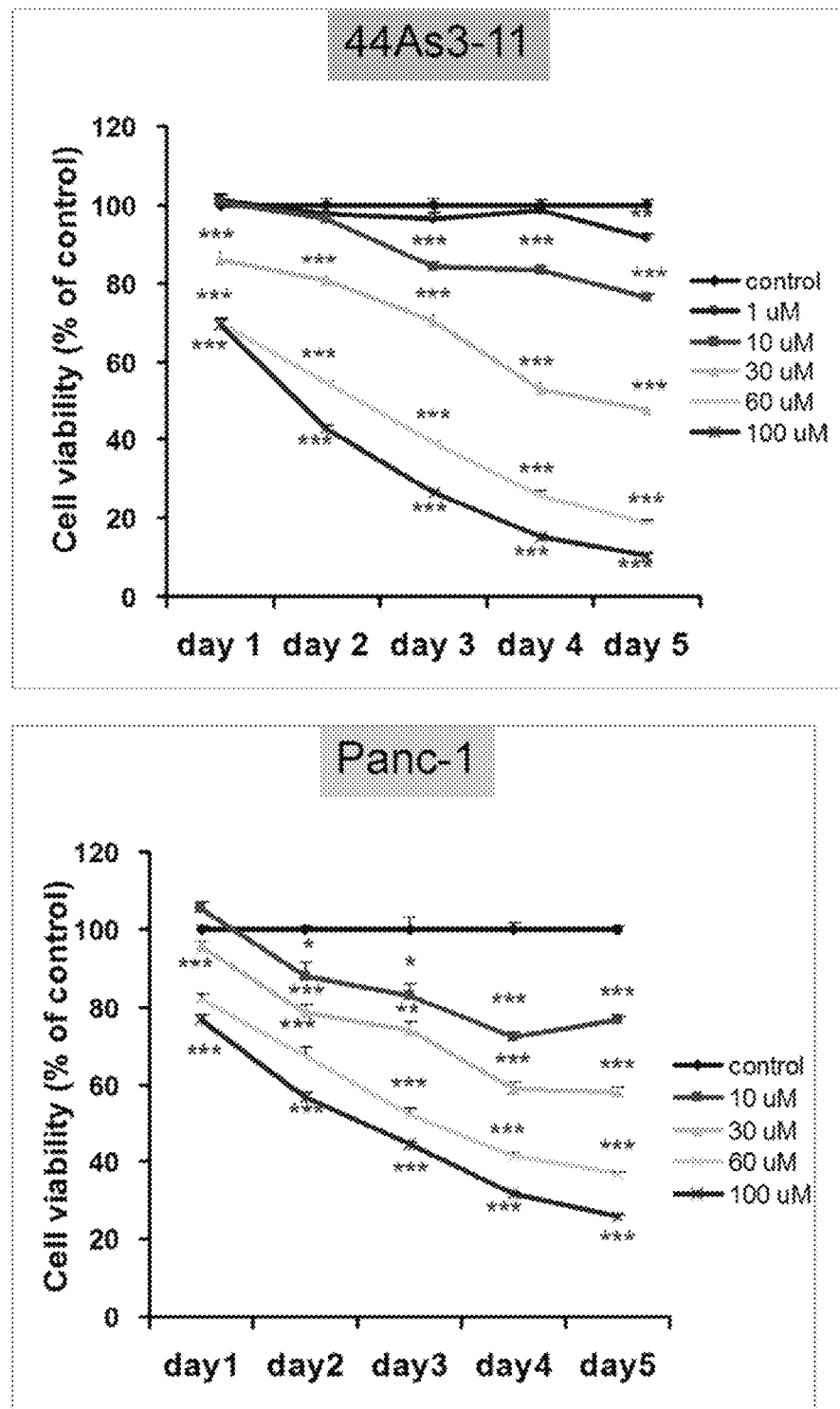
FIG. 11 is a diagram showing an inhibitory effect of a LAT1 selective inhibitor, COM-JP on the proliferation of a 44As3-11 cell derived from human scirrhous stomach cancer and a Panc-1 cell derived from human pancreatic cancer. Each value showed the average value of 4 cases under the same conditions as a relative value based on the activity in the absence of COM-JP as 100%. The average value and the standard error, and the p-value of significance test were shown in the diagram.
Figure 12:
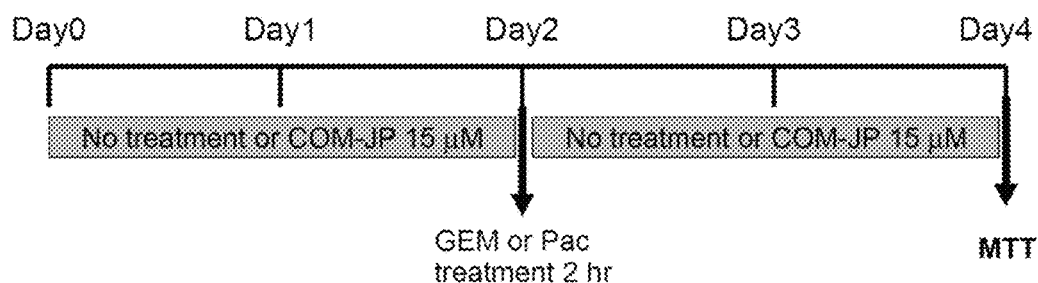
FIG. 12 is a diagram showing a procedure of an experiment in which an effect is shown when each of a LAT1 selective inhibitor, COM-JP, and existing agents, gemcitabine (GEM) and paclitaxel (Pac) was used alone or in combination.

In FIG. 11, each value showed the average value of four cases under the same conditions as a relative value based on the activity in the absence of COM-JP as 100%. The average value and the standard error, and the p-value of significance test were shown in the diagram. Although the difference is recognized depending on the type of the cancer cell, dose-dependent decrease of the proliferation activity of COM-JP was apparently recognized in both cells.

(Effect on the Proliferation of a 44As3-11 Cell Derived from Human Scirrhous Stomach Cancer when COM-JP and other Agents were used in Combination)

The effect on the proliferation of a 44As3-11 cell derived from human scirrhous stomach cancer when each of gemstabine and paclitaxel was used alone for 2 hours represents the difference value of a left bar graph of each group column. In each experiment, three cases of the group under the same conditions were measured, and the average value and the standard error, and the p-value of significance test were shown in the diagram. The proliferation activity in a cell was decreased in a dose-dependent manner in both. The inhibitory effect of paclitaxel was stronger than that of gemstabine. The combined effect resulted from treating with COM-JP (15 µM) for the whole period (a bar graph in the right of each group) was stronger as compared with that resulted from treating with the COM-JP (15 µM) for past 2 days (a bar graph in the middle of each group). The inhibitory effect due to the combination was resulted from the addition of each single effect, and showed a so-called additive effect.

(Effect on the Proliferation of a Panc-1 Cell Derived from Human Pancreatic Cancer when COM-JP and other Agents were Used in Combination)

The effect on the proliferation of a Panc-1 cell derived from human pancreatic cancer when each of gemstabine and paclitaxel was used alone for 2 hours represents the difference value of a left bar graph of each group column. In each experiment, three cases of the group under the same conditions were measured, and the average value and the standard error, and the p-value of significance test were shown in the diagram. The proliferation activity in a cell was decreased in a dose-dependent manner in both. The inhibitory effect of paclitaxel was stronger than that of gemstabine. However, the single effect of gemstabine was extremely small, and was an effect being clearly weaker than the effect on the proliferation of a 44As3-11 cell derived from human scirrhous stomach cancer. Although the inhibition of the combined effect resulted from treating with COM-JP (15 µM) for the whole period (a bar graph in the right of each group) was slightly observed as compared with that resulted from treating with the COM-JP (15 µM) for past 2 days (a bar graph in the middle of each group), the degree of the inhibition was clearly lower as compared with that of the proliferation of a 44As3-11 cell derived from human scirrhous stomach cancer. The inhibitory effect due to each combination in a Panc-1 cell was resulted from the addition of each single effect, and showed a so-called additive effect as in the case of a 44As3-11 cell.

(Effect on the Tumor Growth in a Nude Mouse Model Inoculated with a HT-29 Cell Derived from Human Large Intestine Cancer when COM-JP and 5-FU were Used in Combination)

In the single administration of both pharmaceuticals, the increase of the tumor showed more significant decrease, respectively as compared with that in the untreated control group. With the combination of both, the increase of the residual tumor in each single group was further decreased. It was revealed that this combined effect is additive, and due to the difference of the action mechanism of both pharmaceuticals.

(Synergistic Effect on the Tumor Growth in a Nude Mouse Model (SOI Model) Inoculated in the same Site with a HT-29 Cell Derived from Human Large Intestine Cancer when COM-JP and CDDP were Used in Combination)

In Groups 8 and 9 of FIG. 16, the increase of the tumor is more significantly decreased as compared with that in the untreated control group. From this Result, each efficacy that was not recognized in the single administration of each of COM-JP and CDDP was apparently recognized in the combination of COM-JP and CDDP. It was concluded that the efficacy of due to the combination was a synergistic effect.

<Discussion>

According to the above test results, the following was revealed.

The current study demonstrates that inhibiting LAT1/SLC7A5, an essential amino acid (EAA) transporter, can alter metabolism and survival in ALL/T-LL cellular models. The present inventors used primary cells and cell lines derived from a T cell lymphoma (tPTEN–/–) mouse model generated after the T-lymphocyte specific inactivation of the PTEN tumor suppressor gene. First, a gene expression profiling established that tPTEN–/– cells have elevated SLC7A5 levels compared to resting or activated normal T cells. Tumor cells were also shown to overexpress CD98 at their surface, compared to normal cells. These results are important as they verify that not only LAT1/SLC7A5 levels are higher but also that transformed cells overexpress the membrane spanning protein CD98hc/4F2 encoded by the SLC3A2 gene, that is required for functional LAT1 (Non-Patent Literature 11). Likewise, compared to resting and activated peripheral blood lymphocytes (PBL) via healthy donors, primary human T-ALL samples and T-ALL/T-LL cell lines also displayed enhanced CD98 levels. Expression of CD98 appears to be associated with a poor prognosis in several cancers such as adenocarcinomas (Reference 37, 38), or breast cancer (Referece 39) suggesting that its expression could be related to important pathological characteristics such as intense proliferation and aggressiveness. A high expression of CD98 positively correlated with the proliferation rate (Ki-67) and poorer prognosis in gastric carcinomas (Reference 40) and elevated LAT1/CD98 levels were observed in metastatic sites compared to primary tumors (Reference 41). Collectively, these data prompted the present inventors to investigate the importance of inhibiting essential amino acid LAT1 mediated uptake and its ability to alter T-cell lymphoblastic lymphoma/T-cell acute lymphoblastic leukemia cell growth and survival.

The present inventors' study was first conducted on primary tPTEN–/– cells and cell lines derived from tPTEN–/– tumors. The present inventors tested BCH—a proto-typical System L inhibitor—and D-leucine to compete with neutral amino acid import by LAT1. While both molecules could affect the survival of tPTEN–/– cells, they displayed limited efficiency and required high concentrations (>1.0 mM); similar results have been reported on head and neck squamous cell carcinomas cell lines (Reference 42). The present inventor next examined a potent and LAT1 selective inhibitor, COMPOUND-JP (Reference 43). When added to the cell culture media, COMPOUND-JP significantly decreased tPTEN–/– cell survival ($IC_{50}$=2.4 μM). In addition, COMPOUND-JP displayed a concentration dependent and statistically significant effect on cell proliferation. Addition of EAA to culture media decreased COMPOUND-JP's ability to distort cell viability and cell death, illustrating that COMPOUND-JP presumably acts via a competitive process on EAA influx (Reference 21). The present inventors next performed in vivo imaging experiments by injecting nude mice with KO99L cells which stably express luciferase. COMPOUND-JP produced a significant decrease in tumor volume. While COMPOUND-JP has already been reported to reduce the growth of HT-29 colon cancer cells transplanted in nude mice (Reference 43), the current studies further illustrate the utility of COMPOUND-JP as an LAT1 inhibitor both in vitro and in vivo.

Once the present inventors had established COMPOUND-JP mediated in vitro and in vivo effects on tPTEN–/– cells, the present inventors sought to establish if LAT1 targeting could also alter T-ALL/T-LL cell lines and primary leukemic cells. First, the present inventors used the well-known human Jurkat T-ALL cell line which displayed that COMPOUND-JP influenced in vitro cell survival and proliferation. Secondly, the present inventors isolated primary T-ALL cells from four different human patients and they too displayed a COMPOUND-JP dose dependent effect on cell viability. In contrast to Jurkat cells and patient derived cells, COMPOUND-JP did not induce cell death in normal resting or activated human PBL cells supporting the notion that the LAT1 selective inhibitor has a preferential influence toward leukemic (LAT1 expressing) compared to normal (LAT2 expressing) cells.

At a molecular level, the present inventors observed that COMPOUND-JP could interfere partially with mTORC1 activation. COMPOUND-JP blocked S6RP phosphorylation but did not affect phosphorylation of 4EBP1. Xenografted tPTEN–/– tumors of mice treated with COMPOUND-JP also displayed a strong reduction in phospho-S6RP. The present inventors were also able to observe this mTOR inhibitory effect caused by COMPOUND-JP using phospho-Flow cytometry on two primary T-ALL samples.

An important specificity of COMPOUND-JP is its ability to induce the CHOP transcription factor in the Integrated Stress Response (ISR)/Unfolded Protein Response (UPR). This response, triggered by the accumulation of misfolded proteins in the Endoplasmic Reticulum (ER) or by AA scarcity, allows the cells to restore proteostasis in the ER (Reference 44). If they fail, an apoptotic elimination of the cells is then launched. Furthermore, altering AA content in the media, produced a clear time-dependent CHOP induction. CHOP was also strongly induced by the velcade proteasome inhibitor and with a lower intensity by L-Asparaginase and Erwinase which affect asparagine and glutamine levels and by rapamycin. Inhibitors of PI3K/Akt/mTOR did not induce CHOP. COMPOUND-JP-induced CHOP was modulated via extracellular EAA addition, demonstrating that COMPOUND-JP acts through inhibition of EAA uptake. Moreover, salubrinal, a compound established as an inhibitor which prevents eIF2□ de-phosphorylation and induces cell protection towards ER stress (Reference 32) was able to offset COMPOUND-JP triggered CHOP induction, rescued KO99L cell death, and restored cell proliferation. UPR can be triggered by at least three pathways through ATF6, IRE-1 and PERK (Reference 44). Interestingly, COMPOUND-JP could mobilize the three pathways through ATF6, IRE-1 and PERK suggesting that it could interfere with a common and upstream event.

Molecularly, COMPOUND-JP induced the expression of four pro-apoptotic Bcl-2 family members: Bax, Bak, Bim and Puma that have been associated with UPR and CHOP engagement. The BH3-only protein Puma is induced by tunicamycin with Puma–/– cells showing resistance to ER stress-induced apoptosis (Reference 45). Moreover, CHOP interacts with AP-1 within the Puma promoter region (Reference 46) and directely regulates Bim promoter (Reference 47). Furthermore, Bax and Bak can form a protein complex with the cytosolic domain of IRE1□ that is essential for IRE1□ activation (Reference 48). Modulations of Bax, Bak, Bim and Puma likely participate in the induction of apoptosis at the mitochondrial and ER levels. For instance, COMPOUND-JP exhibited dose dependent mitochondrial depolarization in tPTEN–/– cells that preceeded caspase activation. Apoptosis was found to follow an early autophagic response that likely results from an inhibitory effect of COMPOUND-JP on mTORC1.

Figure 9J:
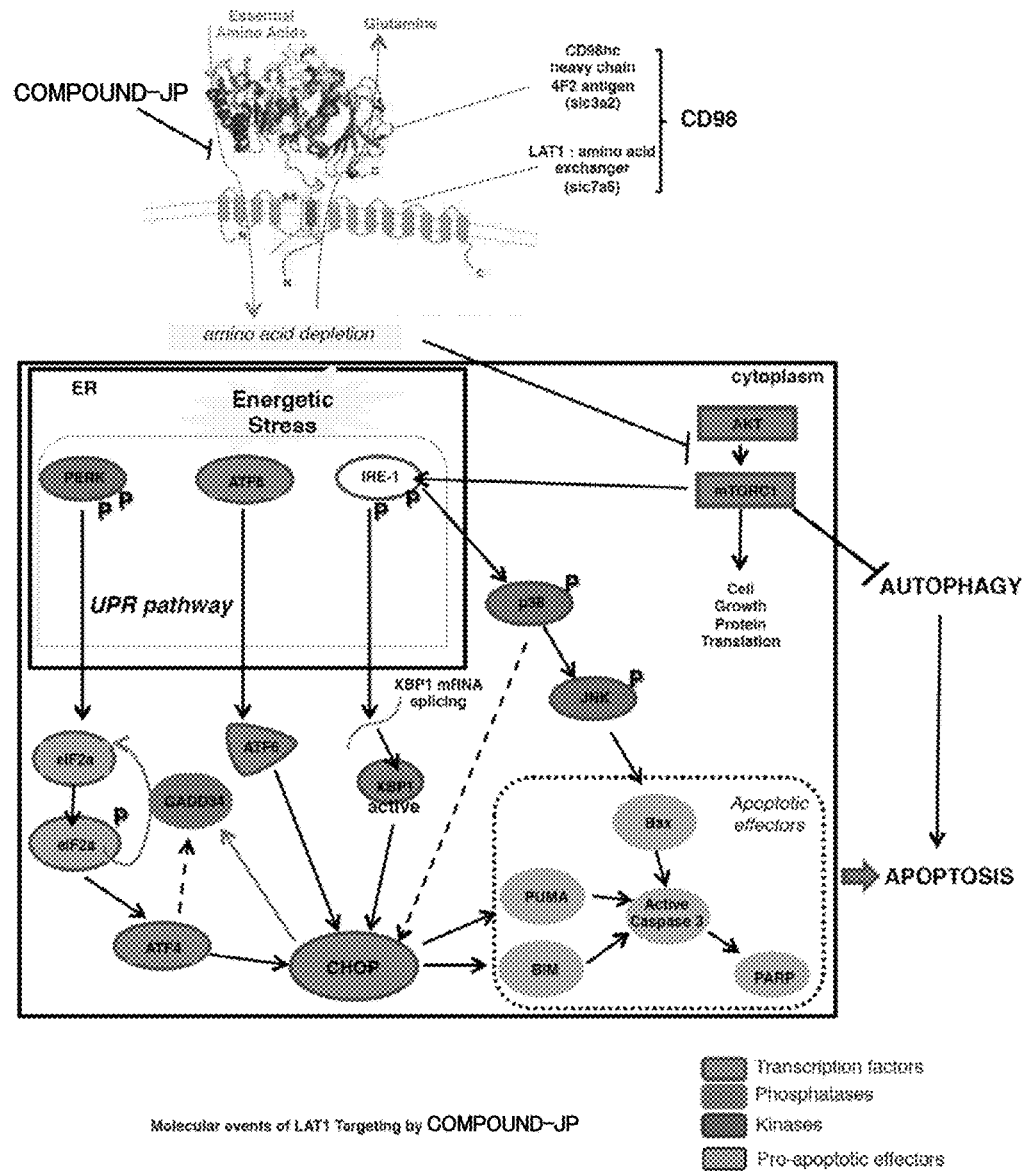
FIG. 9J shows the molecular events of LAT1 Targeting by COMPOUND-JP.

Another interesting aspect of the current studies was the development of a COMPOUND-JP resistant cell line, denoted as KO99-RJ. Not only COMPOUND-JP failed to induce cell death in KO99-RJ but no CHOP induction could be observed either, demonstrating the importance of CHOP in COMPOUND-JP-induced cell death. A tentative model of COMPOUND-JP's mode of action is shown in supplemental FIG. 9J.

While COMPOUND-JP did not affect global protein synthesis it altered the expression of c-myc which has a very short half-life (15 min) that makes it highly sensitive to a decrease in EAA availability preventing its continuous resynthesis. This decrease in c-myc is likely to have dramatic consequences on proliferation and survival of lymphoma cells. Indeed, in normal T cells, LAT1/SLC7A5 is under the control of the T cell antigen receptor (TCR) and its induction is crucial for the proper mounting of an immune response and its reprogrammation of T cell metabolism (Reference 28). T cells with defect in SLC7A5 could not stimulate mTORC1 upon TCR triggering and display a defective c-myc expression. The combination of the two events results in a failure to activate and reprogram metabolism and in a differentiation defect of CD4+ and CD8+ effector cells, crippling the immune response. Interestingly, LAT1 inhibition via COMPOUND-JP was shown to interfere with T cell activation (Reference 49).

LAT1 and 4F2/CD98hc are respectively the light and heavy chains of the heterodimeric CD98 complex. While LAT1 transports large EAA, CD98hc interacts with β integrins (Non-Patent Literature 19). It is still not clear if the two properties are functionally linked. Disruption of CD98hc in ES cells interfered with integrin function, disrupting cell spreading and migration but not adhesion (Non-Patent Literature 19). Reconstitution of null cells with a CD98hc mutant that interacts with β integrins but not with light chain restored integrin signaling but surprisingly was dispensable for Akt activation and protection from apoptosis (Non-Patent Literature 19). By contrast, in CD98hc overexpressing renal epithelial cells, LAT1-dependent amino acid transport and integrin interactions are both important for proliferation (Reference 50). Also, in murine epidermis deletion of CD98hc affected skin homeostasis and wound healing and impaired AA uptake was shown to take part to negatively impinge on src and RhoA activation (Reference 51). Depending on the cell context and dependency, either integrin-interacting functions or AA transport can play the dominant role. In the present inventors' model, although the present inventors did not investigate the role of β integrins, EAA influx through LAT1 appears fundamental for leukemic survival.

Lastly, the present inventors also performed COMPOUND-JP in vitro experiments in combination with various chemotherapeutic drugs or signaling inhibitors and Combination Index (CI) values were computed. Synergistic or additive effects were observed with all compounds tested. In particular COMPOUND-JP showed the highest synergy with rapamycin. If the two drugs are both able to inhibit S6RP phosphorylation and fail to affect phosphorylation of 4EBP1, they have however different modes of action as COMPOUND-JP can induce proliferation arrest and apoptosis while rapamycin is only cytostatic in tPTEN−/− cells (Reference 52). This could be due to the fact that COMPOUND-JP is a stronger inducer of CHOP and can inhibit Akt activation, compared to rapamycin. COMPOUND-JP could also potentiate the anti-leukemic effects of dexamethasone, doxorubicine and L-asparaginase. It has been reported that the toxic effects of the proteasome inhibitor velcade on cancer cells were due to the depletion of intracellular AA pools (Reference 27). This is likely to be amplified by COMPOUND-JP and could account for the observed additive effects of the two molecules on cell viability. The present inventors show that COMPOUND-JP also slightly increased the effect of two inhibitors acting on the PI3K/Akt/mTOR pathway, KU0063794 and PI-103.

Altogether, the present inventors' results show that the overexpression of LAT1 on T-ALL/T-LL cancer cells reflects a cancer cell's addiction towards increased nutrients uptake and activation of mTORC1 and Akt that support their reprogrammed metabolism. Furthermore, the present inventors' study demonstrates in vitro that pharmacological interfering with EAA uptake through LAT1 could represent an interesting global adjuvant therapeutic strategy to treat these deadly hematopoietic malignancies.

At the end, application to other cancers will be demonstrated below. RNA is extracted from each cell, and each mRNA was measured by a quantitative PCR method using a primer specific to LAT1 and LAT2. The results are shown in FIG. 10. Cancer classification name was described in a table with a vertical axis as an amount of mRNA per an RNA unit and with a horizontal axis as name of cancer cell used. LAT1 was described in the upper section and LAT2 was described in the lower section. As can be seen from the diagram, the LAT1 mRNA was expressed in all of the 46 kinds of cells, and it can be said to be a cancer-type transporter. On the other hand, the expression of the LAT2 in a cancer cell is zero or extremely low level, and it can be understand to be a normal type. Therefore, the above results can be applied to other cancers.

In addition, actually, the discussion of the results of the experiments applied to other cancers is shown below.

Firstly, as shown in FIG. 11, although the difference is recognized depending on the type of cancer cell, dose-dependent decrease of the proliferation activity of COM-JP was apparently recognized in both cells of a 44As3-1 cell derived from human scirrhous stomach cancer and a Panc-1 cell derived from human pancreatic cancer. As is apparent from the results in FIG. 10, an inhibitory effect on the proliferation of COM-JP depending on the LAT1 expression level can be expected also in many other LAT1-expressing cancer cells.

Figure 13:
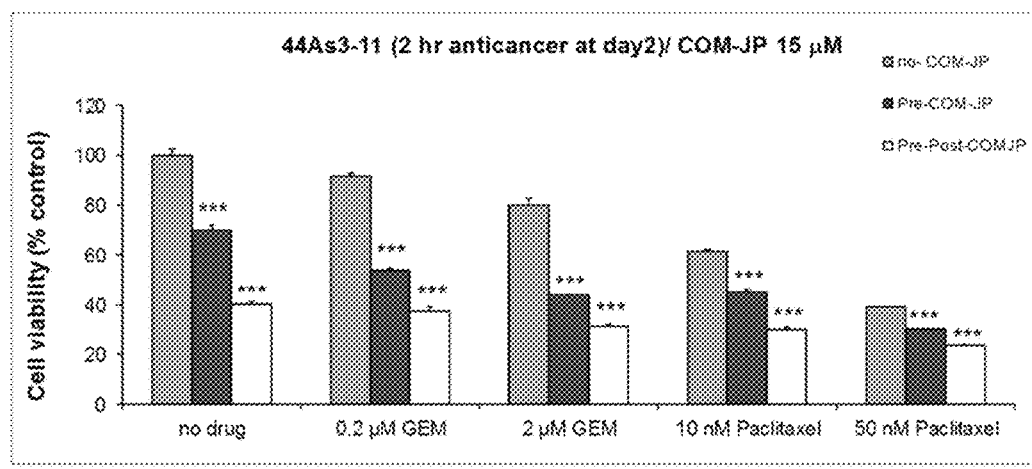
FIG. 13 is a diagram showing an effect on the proliferation of a 44As3-11 cell derived from human scirrhous stomach cancer when COM-JP and other agents were used in combination. The effect on the proliferation of a 44As3-11 cell derived from human scirrhous stomach cancer when each of gemstabine and paclitaxel was used alone for 2 hours represents the difference value of a left bar graph of each group column. In each experiment, three cases of the group under the same conditions were measured, and the average value and the standard error, and the p-value of significance test were shown in the diagram.

Next, as shown in FIG. 13, the proliferation activity in a cell was decreased in a dose-dependent manner in both of gemstabine and paclitaxel. The inhibitory effect of paclitaxel was stronger than that of gemstabine. As to the effect on the proliferation of a 44As3-11 cell derived from human scirrhous stomach cancer when COM-JP and other agents were used in combination, the combined effect resulted from treating COM-JP (15 μM) for past 2 days (a bar graph in the middle of each group) was stronger as compared with that resulted from treating the COM-JP (15 μM) for the whole period (a bar graph in the right of each group). The inhibitory effect due to the combination was resulted from the addition of each single effect, and showed a so-called additive effect.

Figure 14:
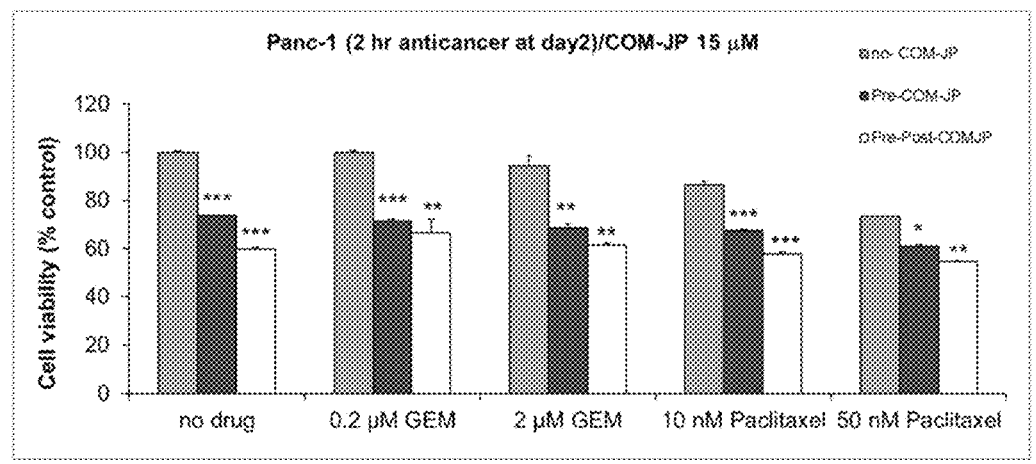
FIG. 14 is a diagram showing an effect on the proliferation of a Panc-1 cell derived from human pancreatic cancer when COM-JP and other agents were used in combination. The effect on the proliferation of a Panc-1 cell derived from human pancreatic cancer when each of gemstabine and paclitaxel was used alone for 2 hours represents the difference value of a left bar graph of each group column. In each experiment, three cases of the group under the same conditions were measured, and the average value and the standard error, and the p-value of significance test were shown in the diagram.

Subsequently, as shown in FIG. 14, the proliferation activity in a cell was decreased in a dose-dependent manner in both of gemstabine and paclitaxel. The inhibitory effect of paclitaxel was stronger than that of gemstabine. However, the single effect of gemstabine was extremely small, and was an effect being clearly weaker than the effect on the proliferation of a 44As3-11 cell derived from human scirrhous stomach cancer. As to the effect on the proliferation of a Panc-1 cell derived from human pancreatic cancer when COM-JP and other agents were used in combination, although the inhibition of the combined effect resulted from treating with COM-JP (15 μM) for the whole period (a bar graph in the right of each group) was slightly observed as compared with that resulted from treating with the COM-JP (15 μM) for past 2 days (a bar graph in the middle of each group), the degree of the inhibition was clearly lower as compared with that of the proliferation of a 44As3-11 cell derived from human scirrhous stomach cancer. The inhibitory effect due to each combination in a Panc-1 cell was resulted from the addition of each single effect, and showed a so-called additive effect as in the case of 44As3-11 cell.

Figure 15:
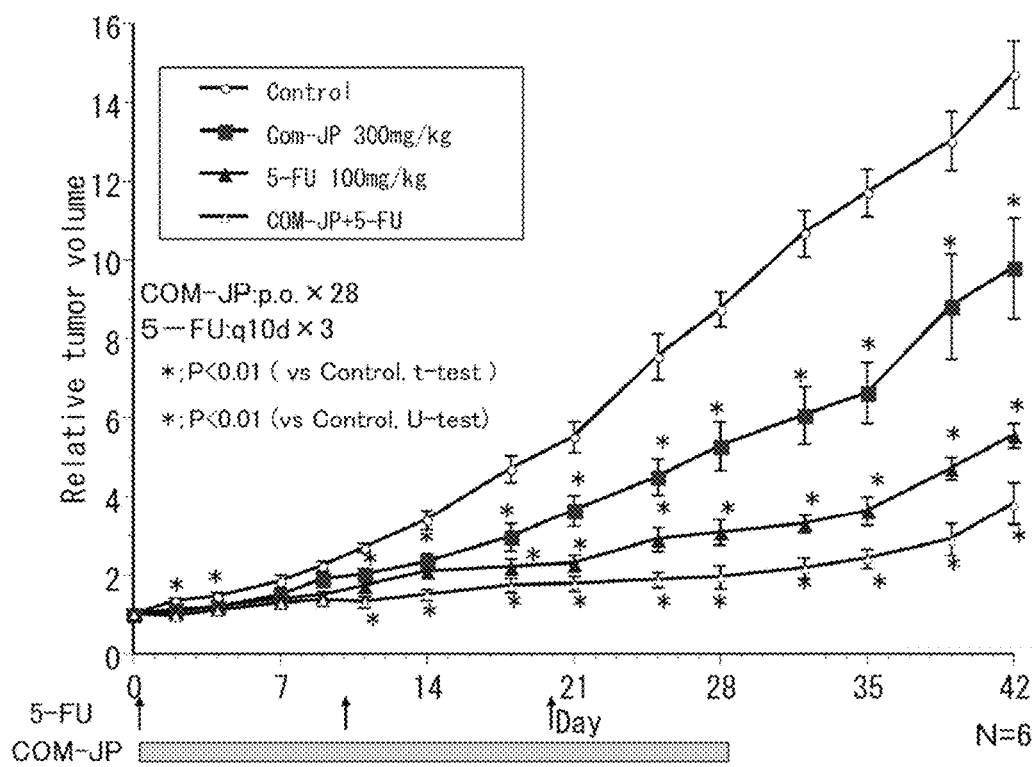
FIG. 15 is a diagram showing an effect on the tumor growth in a nude mouse model inoculated with a HT-29 cell derived from human large intestine cancer when COM-JP and 5-EU were used in combination.

Further, as shown in FIG. 15, in the single administration of each of both pharmaceuticals, the increase of the tumor showed more significant decrease, respectively as compared with that in the untreated control group. As to the effect on the tumor growth in a nude mouse model inoculated with a HT-29 cell derived from human large intestine cancer when COM-JP and 5-FU were used in combination, with the combination of both, the increase of the residual tumor in each single group was further decreased. It was revealed that this combined effect is additive, and due to the difference of the action mechanism of both pharmaceuticals. The efficacy that can further increase the therapeutic effect of each single administration due to such the combination can sufficiently be expected also in a large intestine cancer treatment in clinical.

At the end, as to the synergistic effect on the tumor growth in a nude mouse model (SOI model) inoculated in the same site with a HT-29 cell derived from human large intestine cancer when COM-JP and CDDP were used in combination, as shown in FIG. 16, in Groups 8 and 9 of FIG. 16, the increase of the tumor is more significantly decreased as compared with that in the untreated control group. From this Result, each efficacy that was not recognized in the single administration of each of COM-JP and CDDP was apparently recognized in the combination of COM-JP and CDDP. It was concluded that the efficacy due to this combination was a synergistic effect.

As described above, the additive effect and synergistic effect due to the combination of a LAT1 inhibitor and other agents are revealed, and an anticancer agent composition containing a LAT1 inhibitor according to the present invention, and one or more agents selected from the group consisting of an alkylating agent, a platinating agent, an antimetabolite, a topoisomerase inhibitor, a microtubule inhibitor, an endocrine therapy agent, a microtubule depolymerizing inhibitor, an antitumor antibiotic, and a molecular-targeted agent, as an active component, is effective also for other cancers.

REFERENCES (Reference 21) H. Uchino et al., Transport of amino acid-related compounds mediated by L-type amino acid transporter 1 (LAT1): insights into the mechanisms of substrate recognition. *Molecular pharmacology* 6 1, 729 (April, 2002).

(Reference 22) E. Morimoto et al., Establishment and characterization of mammalian cell lines stably expressing human L-type amino acid transporters. *Journal of pharmacological sciences* 108, 505 (December, 2008).

(Reference 23) L. Galluzzi, N. Larochette, N. Zamzami, G. Kroemer, Mitochondria as therapeutic targets for cancer chemotherapy. *Oncogene* 2 5, 4812 (Aug. 7, 2006).

(Reference 24) A. Puissant, G. Robert, P. Auberger, Targeting autophagy to fight hematopoietic malignancies. *Cell Cycle* 9, 3470 (Sep. 1, 2010).

(Reference 25) M. R. Janes et al., Effective and selective targeting of leukemia cells using a TORC1/2 kinase inhibitor. *Nat Ned* 16, 205 (February, 2010).

(Reference 26) P. Nicklin et al., Bidirectional transport of amino acids regulates mTOR and autophagy. *Cell* 136, 521 (Feb. 6, 2009).

(Reference 27) A. Suraweera, C. Munch, A. Hanssum, A. Bertolotti, Failure of amino acid homeostasis causes cell death following proteasome inhibition. *Molecular cell* 48, 242 (Oct. 26, 2012).

(Reference 28) L. V. Sinclair et al., Control of amino-acid transport by antigen receptors coordinates the metabolic reprogramming essential for T cell differentiation. *Nature immunology* 14, 500 (May, 2013).

(Reference 29) I. Tabas, D. Ron, Integrating the mechanisms of apoptos is induced by endoplasmic reticulum stress. *Nat Cell Biol* 13, 184 (March, 2011).

(Reference 30) S. Oyadomari, M. Mori, Roles of CHOP/GADD153 in endoplasmic reticulum stress. *Cell death and differentiation* 11, 381 (April, 2004).

(Reference 31) H. Zinszner et al., CHOP is implicated in programmed cell death in response to impaired function of the endoplasmic reticulum. *Genes & development* 12, 982 (Apr. 1, 1998).

(Reference 32) M. Boyce et al., A selective inhibitor of eIF2alpha dephosphorylation protects cells from ER stress. *Science* 307, 935 (Feb. 11, 2005).

(Reference 33) P. Walter, D. Ron, The unfolded protein response: from stress pathway to homeostatic regulation. *Science* 334, 1081 (Nov. 25, 2011).

(Reference 34) H. P. Harding et al., An integrated stress response regulates amino acid metabolism and resistance to oxidative stress. *Molecular cell* 11, 619 (March, 2003).

(Reference 35) J. Ye et al., ER stress induces cleavage of membrane-bound ATF6 by the same proteases that process SREBPs. *Molecular cell* 6, 1355 (December, 2000).

(Reference 36) C. H. Pui, W. E. Evans, Treatment of acute lymphoblastic leukemia. *N Engl J Med* 354, 166 (Jan. 12, 2006).

(Reference 37) N. Yanagisawa et al., High expression of L-type amino acid transporter 1 (LAT1) predicts poor prognosis in pancreatic ductal adenocarcinomas. *J Clin Pathol* 65, 1019 (November, 2012).

(Reference 38) H. Nawashiro et al., L-type amino acid transporter 1 as a potential molecular target in human astrocytic tumors. *Int J Cancer* 119, 484 (2006).

(Reference 39) M. Furuya, J. Horiguchi, H. Nakajima, Y. Kanai, T. Oyama, Correlation of L-type amino acid transporter 1 and CD98 expression with triple negative breast cancer prognosis. *Cancer Sci* 103, 382 (February, 2012).

(Reference 40) M. Ichinoe et al., High expression of L-type amino-acid transporter 1 (LAT1) in gastric carcinomas: comparison with non-cancerous lesions. *Pathol Int* 61, 281 (May, 2011).

(Reference 41) K. Kaira et al., 1-type amino acid transporter 1 and CD98 expression in primary and metastatic sites of human neoplasms. *Cancer Sci* 99, 2380 (December, 2008).

(Reference 42) K. Yamauchi et al., System L amino acid transporter inhibitor enhances anti-tumor activity of cisplatin in a head and neck squamous cell carcinoma cell line. *Cancer Lett* 276, 95 (Apr. 8, 2009).

(Reference 43) K. Oda et al., L-type amino acid transporter 1 inhibitors inhibit tumor cell growth. *Cancer Sci* 101, (2010).

(Reference 44) Y. P. Vandewynckel et al., The paradox of the unfolded protein response in cancer. *Anticancer Res* 33, 4683 (November, 2013).

(Reference 45) C. Reimertz, D. Kogel, A. Rami, T. Chittenden, J. H. Prehn, Gene expression during ER stress-induced apoptosis in neurons: induction of the BH3-only protein Bbc3/PUMA and activation of the mitochondrial apoptosis pathway. *The Journal of cell biology* 162, 587 (Aug. 18, 2003).

(Reference 46) S. C. Cazanave et al., CHOP and AP-1 cooperatively mediate PUMA expression during lipoapoptosis. *American journal of physiology. Gastrointestinal and liver physiology* 299, G236 (July, 2010).

(Reference 47) H. Puthalakath et al., ER stress triggers apoptosis by activating BH3-only protein Bim. *Cell* 129, 1337 (Jun. 29, 2007).

(Reference 48) C. Hetz et al., Proapoptotic BAX and BAK modulate the unfolded protein response by a direct interaction with IRE1alpha. *Science* 312, 572 (Apr. 28, 2006).

(Reference 49) K. Hayashi, P. Jutabha, H. Endou, H. Sagara, N. Anzai, LAT1 is a critical transporter of essential amino acids for immune reactions in activated human T cells. *J Immunol* 191, 4080 (Oct. 15, 2013).

(Reference 50) N. Bulus, C. Feral, A. Pozzi, R. Zent, CD98 increases renal epithelial cell proliferation by activating MAPKs. *PLoS One* 7, e40026 (2012).

(Reference 51) E. Boulter et al., CD98hc (SLC3A2) regulation of skin homeostasis wanes with age. *J Exp Med* 210, 173 (Jan. 14, 2013).

(Reference 52) C. Rosilio et al., The metabolic perturbators metformin, phenformin and AICAR interfere with the growth and survival of murine PTEN-deficient T cell lymphomas and human T-ALL/T-LL cancer cells. *Cancer Lett* 336, 114 (Aug. 9, 2013).

(Reference 53) T. Hagenbeek et al., The loss of PTEN allows TCR alphabeta lineage thymocytes to bypass IL-7 and Pre-TCR-mediated signaling. *J Exp Med* 200, 883 (2004).

(Reference 54) N. Lounnas et al., Pharmacological inhibition of carbonic anhydrase XII interferes with cell proliferation and induces cell apoptosis in T-cell lymphomas. *Cancer Lett* 333, 76 (Jun. 1, 2013).

The invention claimed is:
1. A method for treating cancer, comprising:
administering an anticancer agent composition to a subject in need thereof,
wherein the subject has T-cell acute lymphoblastic leukemia/lymphomas,
wherein the anticancer agent composition comprises:
a L-type amino add transporter 1 (LAT1) inhibitor in combination with a synergistic amount of one or more agents selected from the group consisting of rapamycin, KU0063794, PI103, dexamethasone, doxorubicin, and velcade (bortezomib), wherein the LAT1 inhibitor is O-(5-amino-2-phenylbenzoxazole-7-yl)methyl-3,5-dichloro-L-tyrosine, or pharmaceutical acceptable salt thereof.

* * * * *